(12) United States Patent
Nonaka et al.

(10) Patent No.: US 6,746,731 B1
(45) Date of Patent: Jun. 8, 2004

(54) FERROELECTRIC ACTIVE MATRIX DISPLAYS WITH WIDE OPERATING TEMPERATURE RANGE

(75) Inventors: Toshiaki Nonaka, Kakegawa (JP); Hans-Rolf Dübal, Eltville (DE); Rainer Wingen, Hattersheim (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/857,652

(22) PCT Filed: Dec. 13, 1999

(86) PCT No.: PCT/EP99/09863

§ 371 (c)(1),
(2), (4) Date: Sep. 24, 2001

(87) PCT Pub. No.: WO00/36054

PCT Pub. Date: Jun. 22, 2000

(30) Foreign Application Priority Data

Dec. 11, 1998 (DE) .......................................... 198 57 352

(51) Int. Cl.$^7$ ........................ C09K 19/30; C09K 19/34; C07D 239/02; C07D 409/02; C07D 285/12; C07D 213/02

(52) U.S. Cl. .............. 428/1.3; 252/299.61; 252/299.62; 252/299.63; 252/299.67; 544/298; 544/303; 544/333; 546/1; 548/136

(58) Field of Search ................................. 544/298, 303, 544/333; 546/1; 548/136; 428/1.1, 1.3; 349/172; 252/299.61, 299.62, 299.63, 299.67

(56) References Cited

U.S. PATENT DOCUMENTS

| 4,367,924 A | | 1/1983 | Clark |
|---|---|---|---|
| 5,413,735 A | * | 5/1995 | Yamashita et al. ...... 252/299.61 |
| 6,368,679 B1 | * | 4/2002 | Schimidt et al. ............. 428/1.1 |
| 6,482,479 B1 | * | 11/2002 | Dubal et al. ................. 428/1.1 |

FOREIGN PATENT DOCUMENTS

| DE | 198 25 484 | 12/1999 |
|---|---|---|
| EP | 0 032 362 | 7/1981 |
| EP | 0 308 794 | 3/1989 |
| EP | 0 459 406 | 12/1991 |
| WO | WO 92/11241 | 7/1992 |
| WO | WO 97/04039 | 2/1997 |

OTHER PUBLICATIONS

Chemical Abstracts, vol. 124, No. 24, 1996, also referred to as XP002137247.

* cited by examiner

Primary Examiner—Shean C. Wu
(74) Attorney, Agent, or Firm—Frommer Lawrence & Haug LLP

(57) ABSTRACT

The active-matrix display contains a chiral smectic liquid-crystal mixture comprising at least one compound of the formula (I)

$$R^1-(A^1-M^1)_a-(A^2-M^2)_b-A^3-X-B^1-(B^2)_c-R^2 \quad (I).$$

where the symbols are as defined in the description.

12 Claims, No Drawings

FERROELECTRIC ACTIVE MATRIX DISPLAYS WITH WIDE OPERATING TEMPERATURE RANGE

Replacement of the cathode ray tube with a flat panel screen requires a display technology which simultaneously makes it possible to achieve a high resolution, i.e. more than 1 000 lines, a high brightness (>200 $Cd/m^2$), a high contrast (>100:1), a high frame rate (>60 Hz), an adequate color representation (>16 million), a large image format (>40 cm), a low power consumption and a wide viewing angle, at low production costs. At present, there is no technology which fully satisfies all these features simultaneously.

Many manufacturers have developed screens which are based on nematic liquid crystals and have been used in recent years in the field of notebook PCs, personal digital assistants, desktop monitors etc. Use is made here of the technologies STN (supertwisted nematics), AM-TN (active matrix—twisted nematics), AM-IPS (active matrix—in-plane switching) and AM-MVA (active matrix—multidomain vertically aligned), which are described in detail in the relevant literature (see, for example, T. Tsukuda, TFT/LCD: Liquid Crystal Displays Addressed by Thin-Film Transistors, Gordon and Breach 1996, ISBN 2-919875-01-9 and the references cited therein; SID Symposium 1997, ISSN-0097-966X and the references cited therein). Furthermore, mention should be made of the technologies PDP (plasma display panel), PALC (plasma addressed liquid crystal), ELD (electro-luminescent display), FED (field emission display) etc., which are also explained in the above-cited SID report.

Clark and Lagerwall (U.S. Pat. No. 4,376,924) were able to show that the use of ferroelectric liquid crystals (FLC) in very thin cells results in opto-electrical switching or display elements which have response times which are faster by a factor of up to 1 000 compared with conventional TN (twisted nematic) cells (see, for example, EP-A 0 032 362). Owing to this and other favorable properties, for example the possibility of bistable switching and the fact that the contrast is virtually independent of the viewing angle, FLCs are basically suitable for areas of application such as computer displays and TV sets, as shown by a monitor marketed in Japan by Canon since May 1995.

The use of FLCs in electro-optical or fully optical components requires either compounds which form tilted or orthogonal smectic phases and are themselves optically active, or the induction of ferroelectric smectic phases by doping compounds which, although forming such smectic phases, are not themselves optically active, with optically active compounds. The desired phase should be stable over the broadest possible temperature range to ensure that the display has a broad operating range.

The individual pixels of an LC display are usually arranged in an x,y matrix formed by the arrangement of a series of electrodes (conductor tracks) along the rows and a series of electrodes along the columns on the upper or lower side of the display. The points of interception of the horizontal (row) electrodes and the vertical (column) electrodes form, addressable pixels.

This pixel arrangement is usually referred to as a passive matrix. For addressing, various multiplex schemes have been developed, as described, for example, in Displays 1993, vol. 14, No. 2, pp. 86–93, and Kontakte 1993 (2), pp. 3–14. Passive matrix addressing has the advantage of simpler display production and consequently lower production costs, but the disadvantage that passive addressing can only be carried out line by line, which results in the addressing time for the entire screen with N lines being N times the line addressing time. For usual line addressing times of about 50 microseconds, this means a screen addressing time of about 60 milliseconds in, for example, the HDTV (high definition TV, 1152 lines) standard, i.e. a maximum frame rate of about 16 Hz, too slow for displaying moving images. In addition, display of gray shades is often difficult. At the FLC conference in Brest, France (Jul. 20–24, 1997, see Abstract Book 6th International Conference on Ferroelectric Liquid Crystals, Brest/France), a passive FLC display with digital gray shades was shown by Mizutani et al., in which each of the RGB pixels (RGB=red, green, blue) was divided into sub-pixels, allowing the display of gray shades in digital form through partial switching. Using three basic colors (red, green, blue), N gray shades result in $3^N$ colors. The disadvantage of this method is the considerable increase in the number of screen drivers necessary and thus in the costs (in the case of the display shown in Brest, three times as many drivers were necessary as in a standard FLC display without digital gray shades).

In so-called active-matrix technology (AMLCD), a non-structured substrate is usually combined with an active-matrix substrate. An electrically non-linear element, for example a thin-film transistor, is integrated into each pixel of the active-matrix substrate. The non-linear elements can also be diodes, metal-insulator-metal and similar elements, which are advantageously produced by thin-film processes and are described in the relevant literature (see, for example, T. Tsukuda, TFT/LCD: Liquid Crystal Displays Addressed by Thin-Film Transistors, Gordon and Breach 1996, ISBN 2-919875-01-9, and the references cited therein).

Active-matrix LCDs are usually operated with nematic liquid crystals in TN (twisted nematics), ECB (electrically controlled birefringence), VA (vertically aligned) or IPS (in-plane switching) mode. In each case, the active matrix generates an electric field of individual strength on each pixel, producing a change in alignment and thus a change in birefringence, which is in turn visible in polarized light. A severe disadvantage of these processes is the poor video capability, i.e. the excessively slow response times of nematic liquid crystals.

For this and other reasons, liquid-crystal displays based on a combination of ferroelectric liquid-crystal materials and active-matrix elements have been proposed, for example in WO 97/12355 or Ferroelectric 1996, 179, 141–152, W. J. A. M. Hartmann (IEEE Trans. Electron. Devices 1989, 36 (9; Pt. 1), 1895–9, and Dissertation, Eindhoven, The Netherlands, 1990).

Hartmann used a combination of the so-called "quasi-bookshelf geometry" (QBG) of an FLC and a TFT (thin-film transistor) active matrix to simultaneously achieve high response speed, gray shades and high transmission. However, the QBG is not stable over a broad temperature range, since the temperature dependence of the smectic layer thickness disrupts or rotates the field-induced layer structure. Moreover, Hartmann utilizes an FLC material having a spontaneous polarization of more than 20 $nC/cm^2$, which, for pixels having realistic dimensions of, for example, 0.01 $mm^2$, leads to high electrical charges (at saturation, Q=2 AP, A=pixel area, P=spontaneous polarization). With low-cost amorphous silicon TFTs, for example, these high charges cannot reach the pixel in the course of the opening time of the TFT. For these reasons, this technology has not been pursued any further to date.

While Hartmann utilizes the charge-controlled bistability to display a virtually continuous gray scale, Nito et al. have suggested a monostable FLC geometry (Journal of the SID, 1/2, 1993, pp. 163–169) in which the FLC material is aligned by means of relatively high voltages such that only a single stable position results from which a number of intermediate states are generated by application of an electric field via a thin-film transistor. These intermediate states correspond to a number of different brightness values (gray shades) when the cell geometry is matched between crossed polarizers.

The disadvantage of the paper by Nito et al. is the occurrence of a streaky texture which limits the contrast and brightness of this cell (see FIG. 8 of the abovementioned citation). While it is possible to correct the disadvantageous streaky texture by treatment with a high electric voltage (20–50 V) in the nematic or cholesteric phase (see page 168 of the abovementioned citation), such a field treatment is unsuitable for mass production of screens and usually does not result in temperature-stable textures either. Furthermore, this method produces switching only in an angle range of up to a maximum of once the tint angle, which is about 22° in the case of the material used by Nito et al. (cf. p. 165, FIG. 6) and thus produces a maximum transmission of only 50% of the transmission of two parallel polarizers.

The object of the present invention is to provide a preferably chiral smectic active-matrix liquid-crystal display, containing a preferably chiral smectic liquid-crystal mixture, where the liquid-crystal mixture makes it possible to achieve a very high maximum transmission and a very high contrast and a constant threshold voltage over a broad temperature range.

In particular, a ferroelectric active-matrix liquid-crystal display containing a ferroelectric liquid-crystal mixture is to be provided where the liquid-crystal mixture assumes a monostable position, but without forming any streaky texture, is temperature-stable and makes it possible to achieve a very high maximum transmission and a very high contrast and a constant threshold voltage over a broad temperature range.

This object is achieved according to the invention by a chiral smectic active-matrix display containing a liquid-crystal layer having a tilt angle which is virtually constant over a broad temperature range and a virtually constant layer leaning angle, where the liquid-crystal layer comprises at least one compound of the formula (I) below.

Expressly included is the advantageous use of the novel materials and mixtures for active-matrix displays, antiferroelectric displays and twisted smectic displays.

In particular, the object is achieved by a chiral smectic active-matrix display containing a liquid-crystal layer in the form of a monostable monodomain having a tilt angle which is virtually constant over a broad temperature range, and a virtually constant layer leaning angle, where the liquid-crystal layer comprises at least one compound of the formula (I) below.

The active-matrix display contains a chiral smectic liquid-crystal mixture comprising at least one compound of the general formula (I)

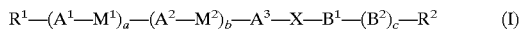

$$R^1-(A^1-M^1)_a-(A^2-M^2)_b-A^3-X-B^1-(B^2)_c-R^2 \quad (I)$$

where the symbols are as defined below:
  $R^1$, $R^2$ are, independently of one another, identical or different and are each
    a) hydrogen, fluorine or CN
    a straight-chain or branched alkenyl, alkenyloxy, alkyl or alkyloxy radical (with or without asymmetric carbon atoms) having 2 to 16 carbon atoms, where
      b1) one or two nonterminal —CH$_2$— groups may be replaced by —O—, —OC(=O)—,
—(C=O), —C(=O)O—, —Si(CH$_3$)$_2$—, —CH(Cl)— and/or one or two —CH$_2$— groups may be replaced by —CH=CH— or —C≡C—
    and one or more H atoms may be replaced by F and/or
      b2) one or more —CH$_2$— groups may be replaced by phenylene-1,4-diyl (unsubstituted, monosubstituted or disubstituted by F), phenylene-1,3-diyl (unsubstituted, monosubstituted or disubstituted by F), cyclohexane-1, 4-diyl (unsubstituted or monosubstituted by F or CN) or cyclopropane-1,2-diyl
    and one or more H atoms may be replaced by F
    with the provisos that only one of the radicals $R^1$, $R^2$ can be hydrogen, F or CN and that two adjacent —CH$_2$— groups cannot be replaced by —O—
  $M^1$, $M^2$ are, independently of one another, identical or different and are each —C(=O)O—, —OC(=O)—, —CH$_2$O—, —OCH$_2$—, —CF$_2$O—, —OCF$_2$—, —CH$_2$CH$_2$—, —CF$_2$CF$_2$—, —CH=CH—, —CH=CF—, —CF=CF—, —C≡C—, —CH$_2$CH$_2$C(=O)O—, —OC(=O)CH$_2$CH$_2$—, —(CH$_2$)$_4$—, —OCH$_2$CH$_2$CH$_2$—, —CH$_2$CH$_2$CH$_2$O—, —OCH$_2$CF$_2$CH$_2$—, —CH$_2$CF$_2$CH$_2$O— or a single bond
  $A^1$, $A^2$, $A^3$ are, independently of one another, identical or different and are each cyclohexane-1,4-diyl (unsubstituted or monosubstituted by F, CH$_3$, CN), cyclohex-1-ene-1,4-diyl, cyclohex-2-ene-1,4-diyl, 2-oxocyclohexane-1,4-diyl, 2-cyclohexen-1-one-3,6-diyl, 1-alkyl-1-silacyclohexane-1,4-diyl, bicyclo[2.2.2]octane-1,4-diyl, spiro[4.5]-decane-2,8-diyl, spiro[5.5]undecane-3,9-diyl, phenylene-1,4-diyl (unsubstituted, monosubstituted or disubstituted by ON, CH$_3$, CF$_3$, OCH$_3$, unsubstituted, monosubstituted, disubstituted, trisubstituted or tetrasubstituted by F), phenylene-1,3-diyl (unsubstituted, monosubstituted or disubstituted by CN, CH$_3$, CF$_3$, OCF$_3$, unsubstituted, monosubstituted, disubstituted, trisubstituted or tetrasubstituted by F), thiophene-2,5-diyl, thiophene-2,4-diyl, (1,3,4)-oxadiazole-2,5-diyl, (1,3,4)-thiadiazole-2,5-diyl, 1,3-thiazole-2,5-diyl, 1,3-thiazole-2,4-diyl, (1,3)-oxazole-2,5-diyl, isoxazole-2,5-diyl, indane-2,6-diyl, naphthalene-2,6-diyl (unsubstituted, monosubstituted or disubstituted by F or CN), 1,2,3,4-tetrahydronaphthalene-2,6-diyl, decaline-2,6-diyl, pyrimidine-2,5-diyl (unsubstituted or monosubstituted by F), pyridine-2,5-diyl (unsubstituted, monosubstituted or disubstituted by F), pyrazine-2,5-diyl (unsubstituted or monosubstituted by F), pyridazine-3, 6-diyl, quinoline-2,6-diyl, quinoline-3,7-diyl, isoquinoline-3,7-diyl, quinazoline-2,6-diyl, 5,6,7,8-tetrahydroquinazoline-2,6-diyl, quinoxaline-2,6-diyl, 1,3-dioxane-2,5-diyl (unsubstituted or monosubstituted by CN), benzothiazole-2,6-diyl, piperidine-2,4-diyl, piperazine-1,4-diyl
  $B^1$ is cyclohexane-1,4-diyl (unsubstituted, monosubstituted or disubstituted by F, CH$_3$, CN), perfluorocyclohexane-1,4-diyl, cyclohex-1-ene-1,4-diyl, cyclohex-2-ene-1,4-diyl, 1-alkyl-1-silacyclohexane-1,4-diyl, bicyclo[2.2.2]octane-1,4-diyl, cyclopentane-1,3-diyl, cycloheptane-1,4-diyl, tetrahydrofuran-2,5-diyl, tetrahydrofuran-2,4-diyl, phenylene-1,4-diyl (unsubstituted, monosubstituted or disubstituted by CN, CH$_3$, CF$_3$, OCF$_3$, unsubstituted, monosubstituted, disubstituted, trisubstituted or tetrasubstituted by F), phenylene-1,3-diyl (unsubstituted, monosubstituted or disubstituted by CN, CH$_3$, CF$_3$, OCF$_3$, unsubstituted, monosubstituted, disubstituted or trisubstituted by F), thiophene-2,5-diyl (unsubstituted or monosubstituted by F), thiophene-2,4-diyl (unsubstituted or monosubstituted by F), 1,3-thiazol-2,5-diyl (unsubstituted or monosubstituted by F), 1,3-thiazol-2,4-diyl (unsubstituted or monosubstituted by F), (1,3,4)-thiadiazol-2,5-diyl, 1,3-dioxane-2,5-diyl (unsubstituted or monosubstituted by CN), tetrahydropyran-2,5-diyl, 6,6-difluorotetrahydropyran-2,5-diyl, 6,6-difluoro-2,3-dihydro-6H-pyran-2,5-diyl, 6-fluoro-3,4-dihydro-2H-pyran-2,5-diyl, piperidine-1,4-diyl, piperazine-1,4-diyl, pyrimidine-2,5-diyl (unsubstituted or monosubstituted by F), pyridine-2,5-diyl (unsubstituted or monosubstituted by F), 1,2,3,4-tetrahydronaphthalene-2,6-diyl, decaline-2,6-diyl B$^2$ is cyclohexane-1,4-diyl (unsubstituted, monosubstituted or disubstituted by F, CH$_3$, CN), cyclohex-1-ene-1,4-diyl (unsubstituted or monosubstituted by F), cyclohex-2-ene-1,4-diyl, 1-alkyl-1-silacyclohexane-1,4-diyl, bicyclo[2.2.2]octane-1,4-diyl, phenylene-1,4-diyl (unsubstituted, monosubstituted or disubstituted by CN, CH$_3$, CF$_3$, OCF$_3$, unsubstituted, monosubstituted, disubstituted, trisubstituted or tetrasubstituted by F), phenylene-1,3-diyl (unsubstituted, monosubstituted or disubstituted by CN, CH$_3$, CF$_3$, OCF$_3$, unsubstituted, monosubstituted, disubstituted or trisubstituted by F), thiophene-2,5-diyl, thiophene-2,4-diyl, 1,3-thiazole-2,5-diyl, 1,3-thiazol-2,4-diyl, (1,3,4)-thiadiazole-2,5-diyl, 1,3-dioxane-2,5-diyl (unsubstituted or monosubstituted by CN), tetrahydrofuran-2,5-diyl, tetrahydropyran-2,5-diyl, 6,6-difluorotetrahydropyran-2,5-diyl, 6,6-difluoro-2,3-dihydro-6H-pyran-2,5-diyl, 6-fluoro-3,4-dihydro-2H-pyran-2,5-diyl, pyrimidine-2,5-diyl (unsubstituted or monosubstituted F), pyridine-2,5-diyl (unsubstituted or monosubstituted F), indane-2,6-diyl, piperidine-1,4-diyl, piperazine-1,4-diyl, pyrimidine-2,5-diyl (unsubstituted or monosubstituted by F)

X is —(CH$_2$)$_n$—, where
a) one or two —CH$_2$— groups may be replaced by —O— or —C(=O)— and/or
b) one —CH$_2$CH$_2$— group may be replaced by —CH=CH— and one or more H of the —CH$_2$— groups may be replaced by F with the provisos that
1) n is 2, 3 or 4
2) two adjacent —CH$_2$— groups cannot be replaced by —O— a, b, c are each zero, 1 or 2, with the provisos that
1) a must be 1 when R$^1$ is hydrogen, F or CN
2) the sum of a+b+c is at least 1
3) the radicals A and M, respectively, in the brackets may be identical or different when the corresponding index is 2.

Here and hereinbelow, it will be understood that bivalent radicals were designated in the "free state". This designation is essential for the characterization of the compounds, although strictly in accordance with IUPAC rules, other designations of the bivalent radicals forming part of the entire Markush formula—meaning incorporation both as image and as mirror image—would be possible.

According to one embodiment, R$^1$ and R$^2$ are no alkenyl or alkenyloxy radicals.

The active-matrix display is preferably a monostable ferroelectric active-matrix display containing a liquid-crystal layer in the form of a monodomain having an unambiguously defined direction of the layer normal z of the SmC phase, where the layer normal z and the preferential direction n in the nematic or cholesteric phase (N* phase) form an angle of more than 5° and the liquid-crystal layer is composed of a ferroelectric (chiral smectic) liquid-crystal mixture comprising at least one compound of the formula (I).

The spontaneous polarization of the liquid-crystal mixture is preferably <200 nC/cm$^2$, particularly preferably <25 nC/cm$^2$, especially <15 nC/cm$^2$, the value DT (15,1), which is defined below, being >20.

The processes for producing the materials which are suitable for the mixtures of the invention are known in principle, as is the production of liquid-crystal mixtures from the individual components.

For example, the following materials have been described:

thiadiazole derivatives: EP-A-0 309 514; EP-A-0 335 348; U.S. Pat. No. 5,076,961; U.S. Pat. No. 5,200,109 thiazole derivatives: EP-A-0 309 514; EP-A-0 439 170 pyrimidine derivatives: EP-A-0 220 296; 220 297; 227 717; 224 579; 293 910; U.S. Pat. No. 4,891,151; EP-B 0 308 794; U.S. Pat. No. 5,200,521; U.S. Pat. No. 5,370,823; DE-A 43 00 435

4-fluoropyrimidine derivatives: U.S. Pat. No. 5,344,585; EP-A-0 158 137 pyridine derivatives: WO 86/06401; EP-A-0 206 228; EP-A-0 239 403; U.S. Pat. No. 4,795,587; JP-A 07309858; JP-A 62207257; JP-A 05331143; JP-A 05213875; JP-A 04356464; JP-A 01031765; JP-A 08062560; DE-A 40 26 233 fluorinated pyridine derivatives: JP-B 2079059; U.S. Pat. No. 5,389,291; U.S. Pat. No. 5,630,962; U.S. Pat. No. 5,445,763; DE-A 44 27 199; U.S. Pat. No. 5,445,763

2-fluoropyrazine derivatives: U.S. Pat. No. 5,562,859

1,2,3,4-tetrahydroquinazoline derivatives: U.S. Pat. No. 4,402,849; JP-A 08062559; JP-A 08059629; JP-A 07207267 quinoline derivatives: DE-A 195.38 404 dioxane derivatives: Flüssige Kristalle in Tabellen II (liquid crystals in tables II), pp. 349–352; DD 249 277; DD 249 278; DD 249 279 isoxazole derivatives: Mol. Cryst. Liq. Cryst. 1993, 225, 175–182 pyrane derivatives: JP-A 10168076; JP-A 10176168 naphthalene derivatives: Flüssige Kristalle in Tabellen II (liquid crystals in tables II) pp. 313–322; DE-A 195 17 056; DE-A 195 17 038; DE-A 195 70 60; DE-A 195 22 167; DE-A 196 52 247; WO 92/16500; EP-A-0 302 875 indane derivatives: EP-A-0 546 338 fluorophenyl derivatives: EP-A-0 210 215; GB-A 2,198, 743 difluorophenyl derivatives: EP-A-0 210 215; EP-A-0 332 024, 332 025 trifluorophenyl derivatives: EP-A-0 602 596 tetrafluorophenyl derivatives: EP-A-0 110 002; EP-A-0 113 293; EP-A-0 422 996; JP 58188840; JP 59010553; JP 02180869; Mol. Cryst. Liq. Cryst. 127, 413 (1985)

biphenyl and terphenyl derivatives: Flüssige Kristalle in Tabellen II (liquid crystals in table II) pp. 269–304; EP-A-0 213 841; EP-A-0 263 843; GB-B 2,198,743; GB-B 2,200,912; EP-B-0 395 666; EP-B-0 332 006; EP-A-0 360 042 bicyclo[2.2.2]octane derivatives: Flüssige Kristalle in Tabellen II (liquid crystals in table II) pp. 85–95 cyclohexane derivatives: Flüssige Kristalle in Tabellen II (liquid crystals in table II) pp. 32–72; Landolt-Börnstein Vol. IV/7a, pp. 160–176; DE-A 23 44 732; 24 50 088; 24 29 093; 26 36 684; 27 01 591; 27 52 975; DE-A-32 31 707; EP-A 0 233 267; EP-A 0 238 576 cyclohexene derivatives: Flüssige Kristalle in Tabellen II (liquid crystals in table II) pp. 79–82; U.S. Pat. No. 5,271,864; DE-A 39 30 119

1-alkylsilacyclohexane derivatives: EP-A-0 761 674; 742 222; 732 335; 727 428 meta-substituted mesogens: U.S. Pat. No. 5,447,656 thiophene derivatives: Flüssige Kristalle in Tabellen II (liquid crystals in tables II) pp. 353–356; EP-A-0 458 347; EP-A-0 364 923; EP-A-0 392 510; EP-A-0 459 406 benzothiazole derivatives: JP-A 09059266 phenanthrene derivatives: U.S. Pat. No. 5,648,021; EP-B 0 743 971; DE-A 195 24 230; DE-A 197 48 819; DE-A 196 53 010; DE-A 196 53 009; DE-A 196 53 008 fluorene derivatives: Landolt-Börnstein Vol. IV/7a, pp. 36–41; DE-A 197 20 289 ethyne derivatives: U.S. Pat. No. 5,626,792; 5,178,791; 5,457,235; JP 10195025; WO 98 23637; JP 10130188; JP 10120600; EP-A-0 799 878 ethane derivatives: WO 98 23583; WO 98 23563; JP 10147544; JP 09235550; JP 0914660; JP 09087210; JP 06056703; DE-A 42 38 377; JP 06025030; DE-A 32 01 721 and compounds containing the structural elements silylalkyl: EP-B-0 366 561 cyclopropylalkyl: EP-B-0 318 423/398 155 perfluoroalkyl: Ferroelectrics 1988, 85, 375–384 or U.S. Pat. Nos. 4,886,619, 5,082,587, 5,254,747, 5,262,082, 5,437,812 or 5,482,650 perfluorocyclohexyl: DE-A 197 48 818

(x-fluorocarbonyloxy: Liquid Crystals 1997, vol. 23, no. 5, pp. 659–666

2,3-difluoroalkyloxy: U.S. Pat. No. 5,051,506

2-fluoroalkyloxy: U.S. Pat. No. 4,798,680

(x-chlorocarbonyloxy: U.S. Pat. No. 4,855,429 methyl-branched alkyl chains: EP-B-0 201 578, 211 030; DE-A 196 27 899 containing only one Pendant group: EP-A-0 541 081; EP-A-0 606 090 propionyloxy: DD 284 894; EP-A-0 552 658; GB-B 2,235,192 tetrahydrofuranoyloxy: EP-A-0 355 561 cyanoalkyl: EP-A-0 310 620; EP-A-0 333 760; WO 89/05792 containing an oxirane group: EP-B-0 263 437; EP-B-0 292 954; EP-B-0 365 820; DE-A 4133710; JP-B 2089393; JP-B 3-512741 containing a 1,3-dioxolane group: EP-B-0 288 813; EP-B-0 361 272; EP-B-0 462 156; EP-B-0 351 746

It has been found in accordance with the invention that active-matrix displays in which the ferroelectric smectic phase is stable over a broad temperature range are obtainable by using the compounds of the formula (I). Furthermore, the acute angle is very stable over a broad temperature range, i.e. it is only subject to very small changes. The same applies to the layer leaning angle.

In formula (I), X is preferably —OC(=O)—, —OCH$_2$— or —OC(=O)CH$_2$CH$_2$—, particularly preferably —OC(=O).

B$^1$ is preferably cyclohexane-1,4-diyl, cyclohex-1-ene-1,4-diyl, phenylene-1,4-diyl, unsubstituted, monosubstituted or disubstituted by F, or thiophene-2,5-diyl, particularly preferably cyclohexane-1,4-diyl or thiophene-2,5-diyl.

A$^1$ is preferably pyrimidine-2,5-diyl (unsubstituted or monosubstituted by F), pyridine-2,5-diyl (unsubstituted or monosubstituted by F), phenylene-1,4-diyl (unsubstituted, monosubstituted or disubstituted by F) or (1,3,4)-thiadiazole-2,5-diyl.

Preferred compounds of the formula (I) correspond to the formulae

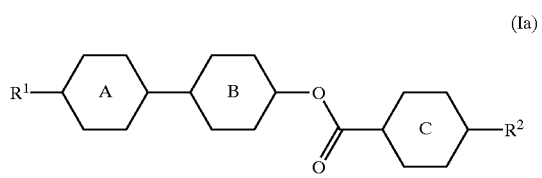

(Ia)

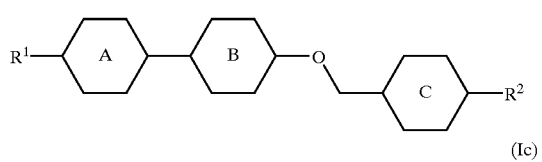

(Ib)

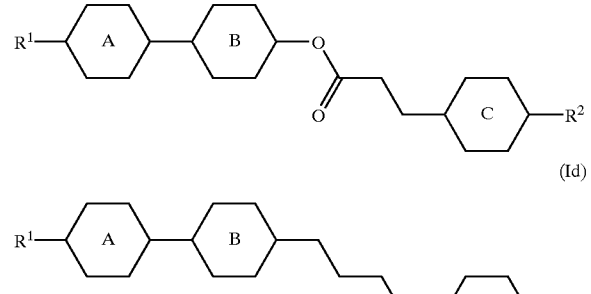

(Ic)

(Id)

where R$^1$, R$^2$ are as defined above and

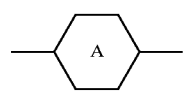

is a bivalent radical selected from the group consisting of phenylene-1,4-diyl, unsubstituted, monosubstituted or disubstituted by F, pyrimidine-2,5-diyl, unsubstituted or monosubstituted by F, pyridine-2,5-diyl, unsubstituted or monosubstituted by F, (1,3,4)-thiadiazole-2,5-diyl, indane-2,5-diyl, cyclohexane-1,4-diyl, unsubstituted or monosubstituted by F or CN, cyclohex-1-ene-1,4-diyl, 1,2,3,4-tetrahydroquinazoline-2,6-diyl

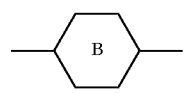

is a bivalent radical selected from the group consisting of phenylene-1,4-diyl, unsubstituted, monosubstituted or disubstituted by F, pyrimidine-2,5-diyl, unsubstituted or monosubstituted by F, pyridine-2,5-diyl, unsubstituted or monosubstituted by F, indane-2,5-diyl

is a bivalent radical selected from the group consisting of cyclohexane-1,4-diyl, unsubstituted or monosubstituted by F or CN, cyclohex-1-ene-1,4-diyl, (1,3)-dioxane-2,5-diyl, unsubstituted or monosubstituted by CN, thiophene-2,5-diyl, thiophene-2,4-diyl, phenylene-1,4-diyl, unsubstituted, monosubstituted or disubstituted by F, phenylene-1,3-diyl, unsubstituted, monosubstituted or disubstituted by F.

Particularly preferred compounds of the formula (I) correspond to the formulae

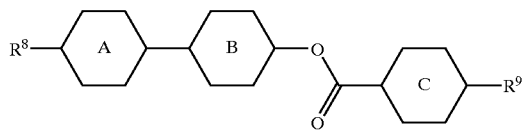
(Ia1)

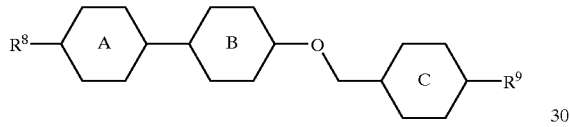
(Ib1)

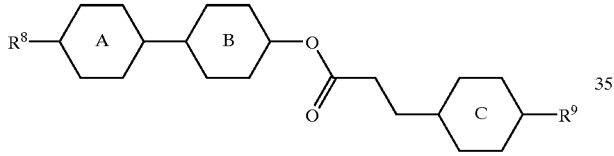
(Ic1)

where:

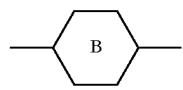

is a bivalent radical selected from the group consisting of phenylene-1,4-diyl, unsubstituted, monosubstituted or disubstituted by F, (1,3,4)-thiadiazol-2,5-diyl, pyrimidine-2,5-diyl, unsubstituted or substituted by F, pyridine-2,5-diyl, unsubstituted or substituted by F ortho to the nitrogen atom, 1,2,3,4-tetrahydroquinazoline-2,6-diyl

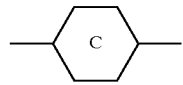

is a bivalent radical selected from the group consisting of phenylene-1,4-diyl, unsubstituted, monosubstituted or disubstituted by F, pyrimidine-2,5-diyl, unsubstituted or monosubstituted by F, pyridine-2,5-diyl, unsubstituted or monosubstituted by F

is a bivalent radical selected from the group consisting of cyclohexane-1,4-diyl, thiophene-2,5-diyl, phenylene-1,4-diyl and $R^8$, $R^9$ are each, independently of one another, hydrogen or a straight-chain or branched alkyl or alkoxy radical having 1 to 16 carbon atoms, where one or two nonterminal —CH$_2$— groups maybe replaced by —O— or —C(=O)— or —CH=CH— with the provisos that $R^8$ and $R^9$ cannot both be hydrogen and that two adjacent —CH$_2$— groups cannot be replaced by —O—.

Very particularly preferred compounds correspond to the formulae

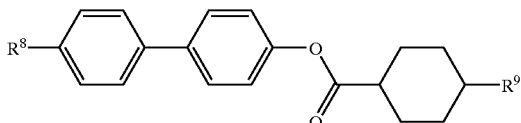
(Ia1a)

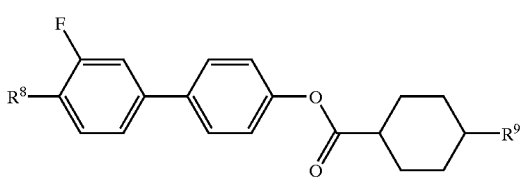
(Ia1b)

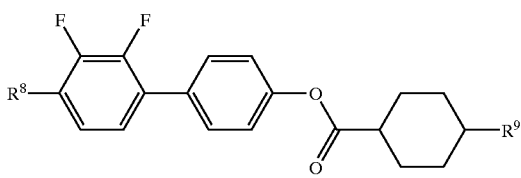
(Ia1c)

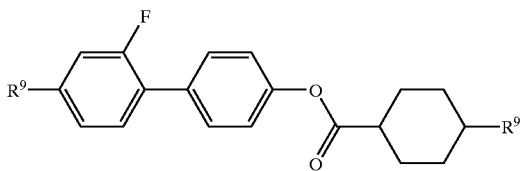
(Ia1d)

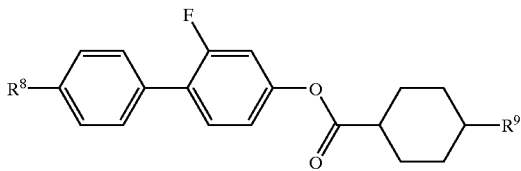
(Ia1e)

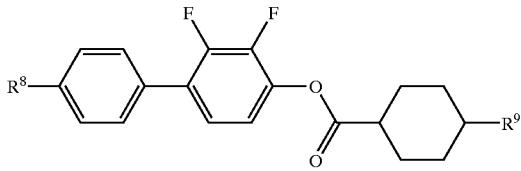
(Ia1f)

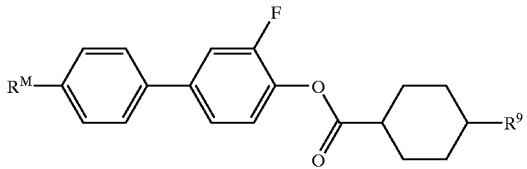
(Ia1g)

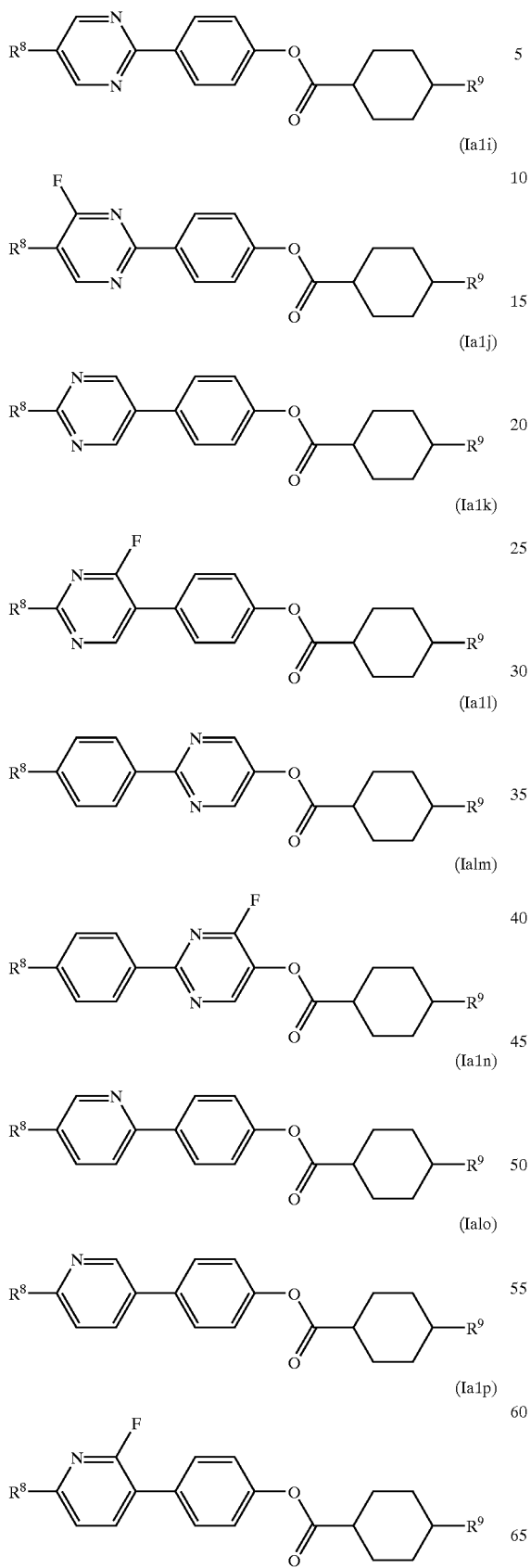
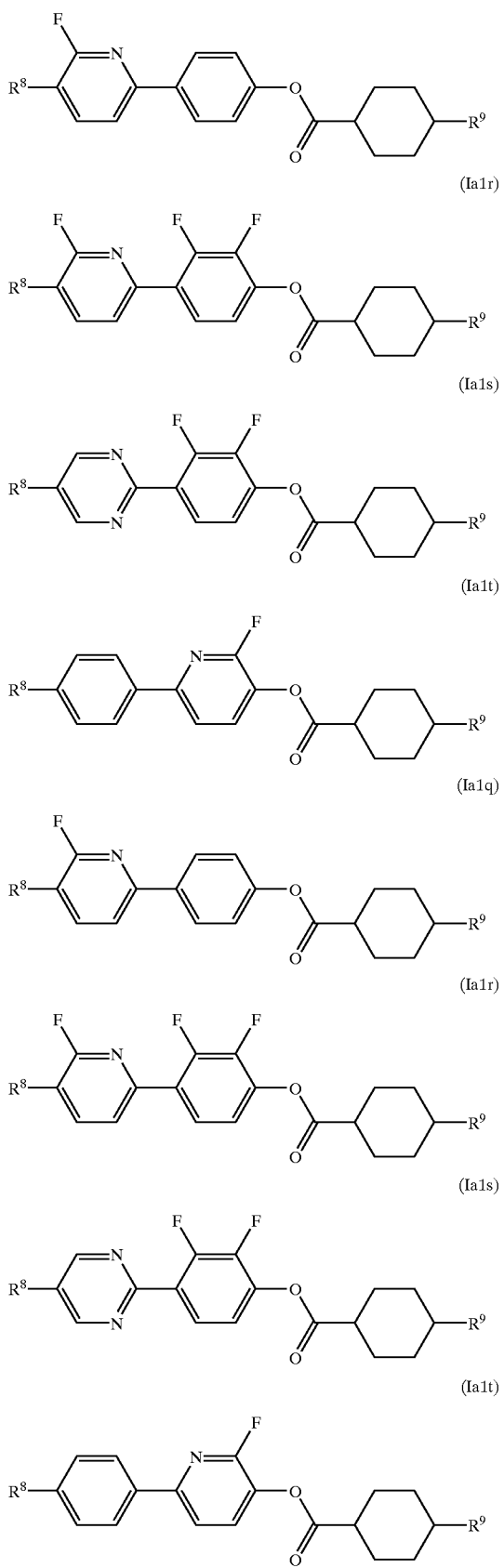

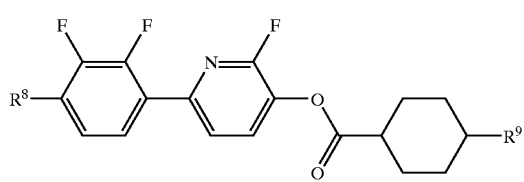
(Ia1u)
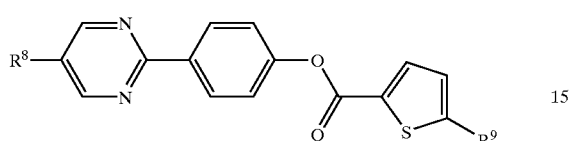
(Ia1v)
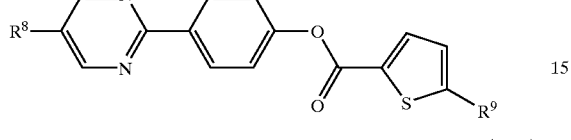
(Ia1w)
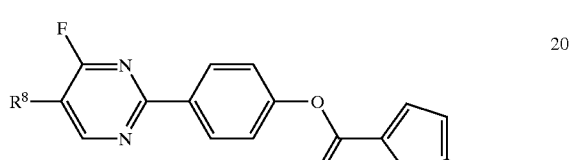
(Ia1x)
(Ia1y)
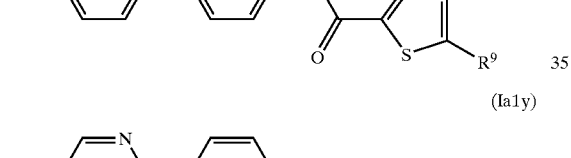
(Ia1z)
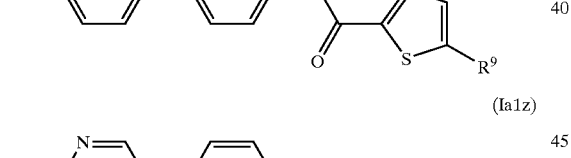
(Ia1aa)
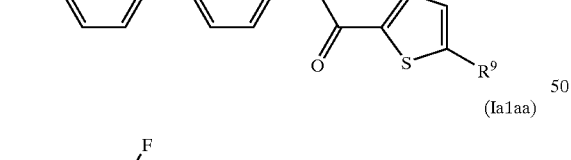
(Ia1ab)
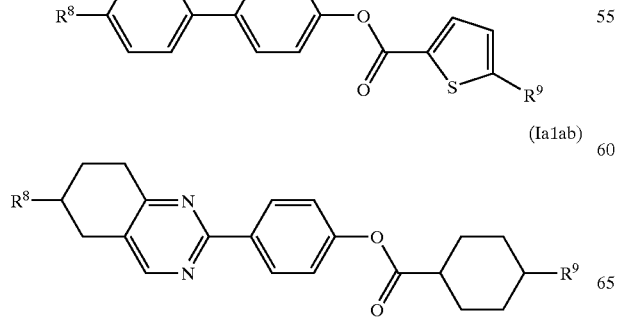
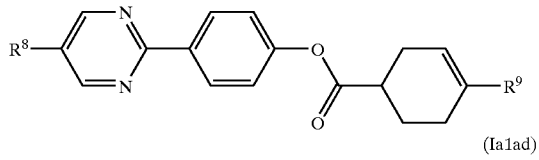
(Ia1ac)
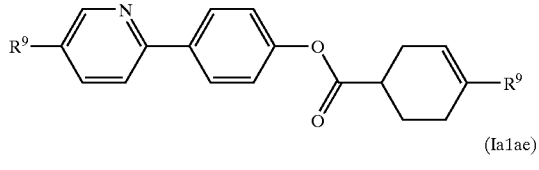
(Ia1ad)
(Ia1ae)
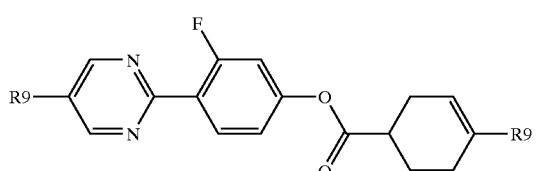
(Ia1af)
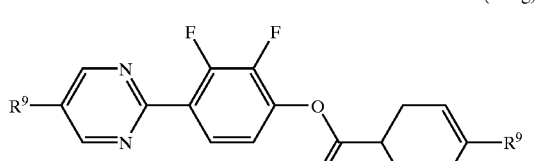
(Ia1ag)
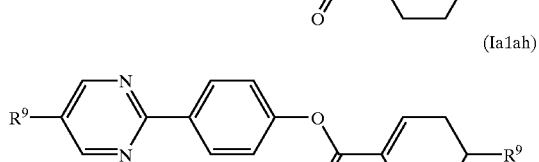
(Ia1ah)
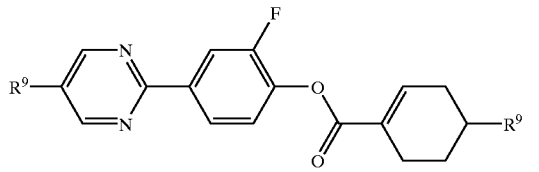
(Ia1ai)
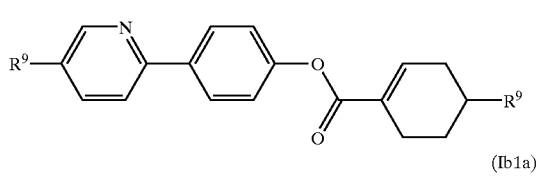
(Ia1ak)
(Ib1a)

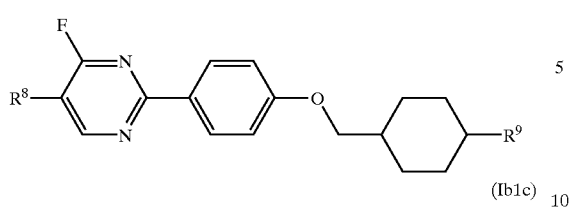
(Ib1b)
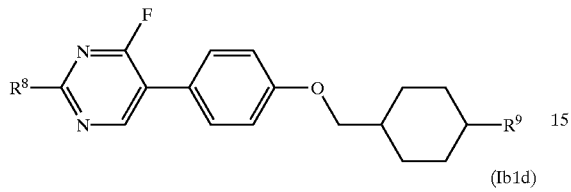
(Ib1c)
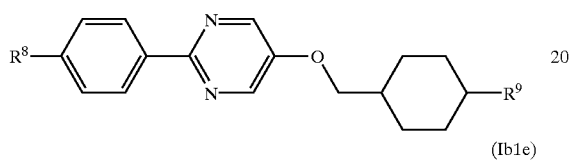
(Ib1d)
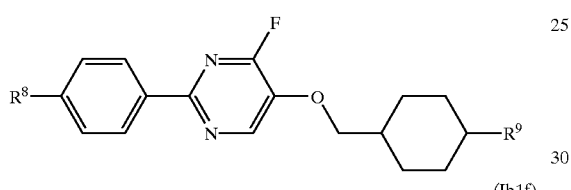
(Ib1e)
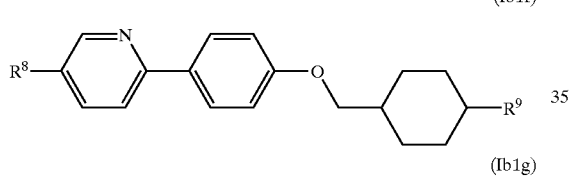
(Ib1f)
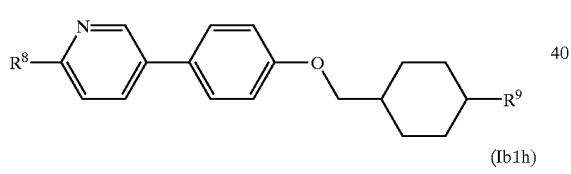
(Ib1g)
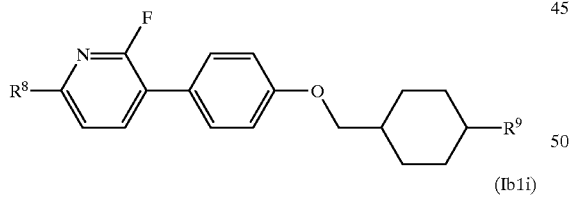
(Ib1h)
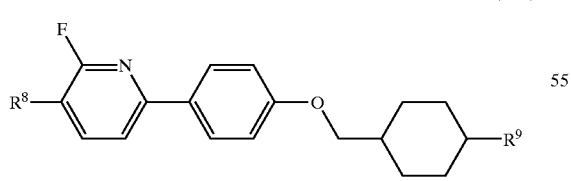
(Ib1i)
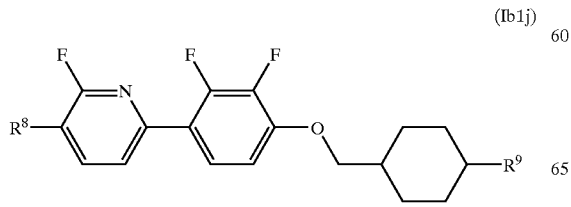
(Ib1j)
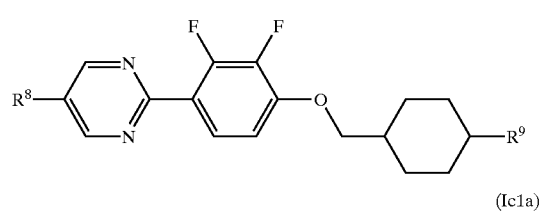
(Ib1k)
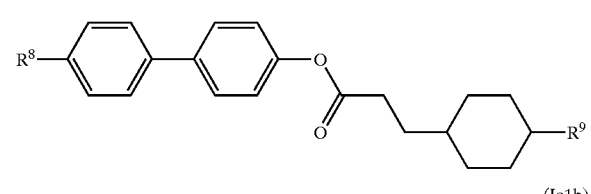
(Ic1a)
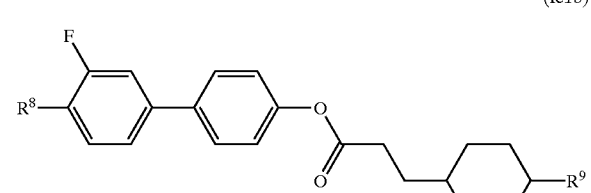
(Ic1b)
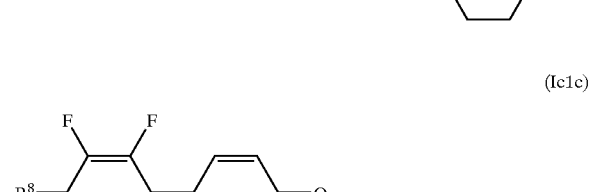
(Ic1c)
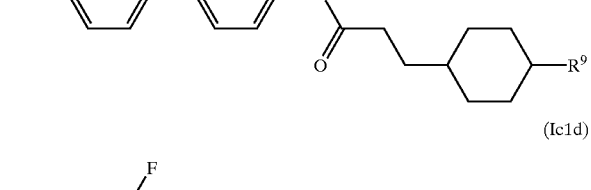
(Ic1d)
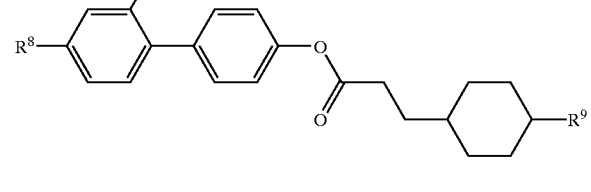
(Ic1e)
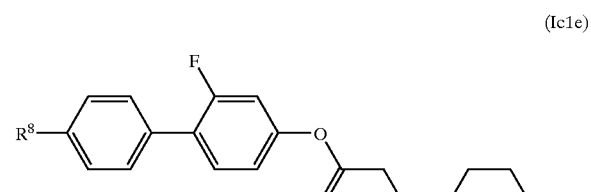
(Ic1f)
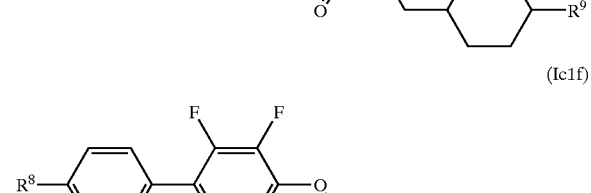
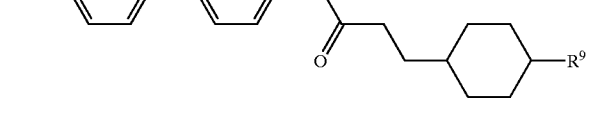

(Ic1g)
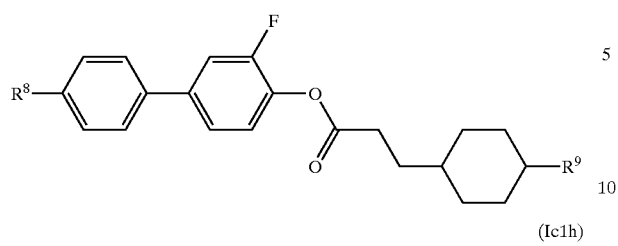

(Ic1h)
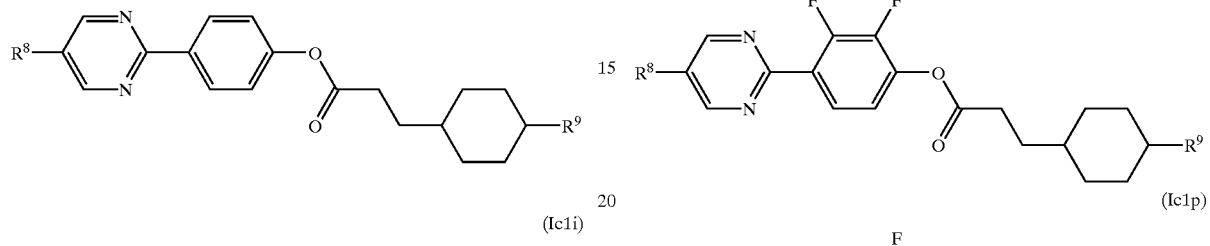

(Ic1i)
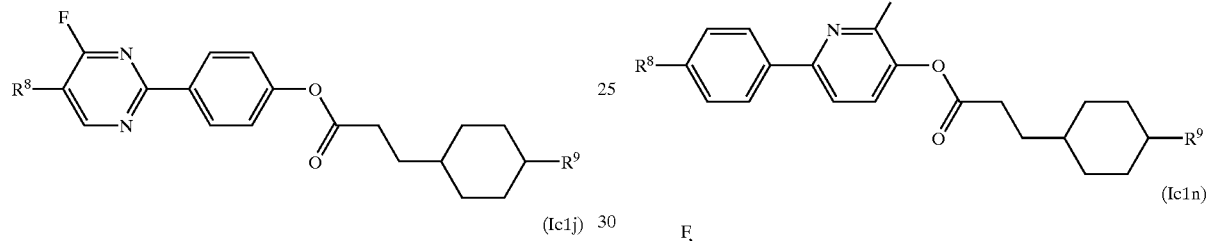

(Ic1j)
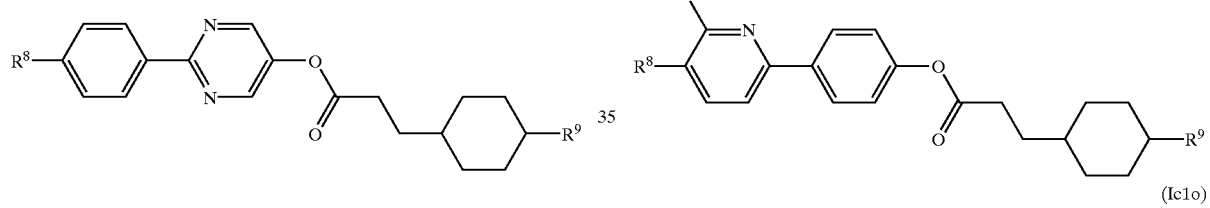

(Ic1k)
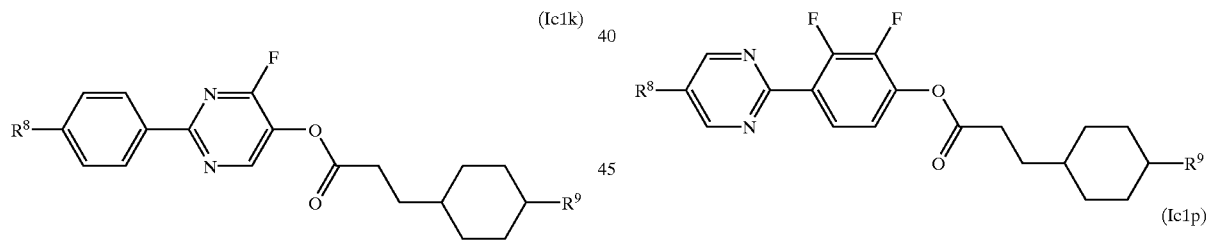

(Ic1l)
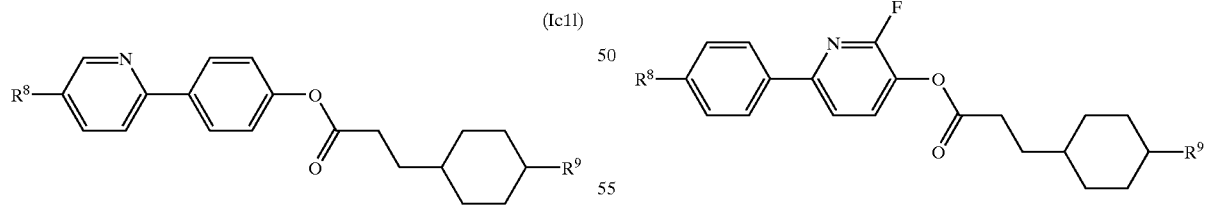

(Ic1m)
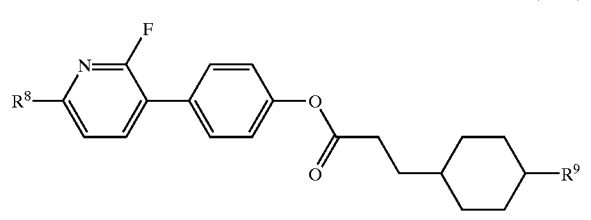

(Ic1n)
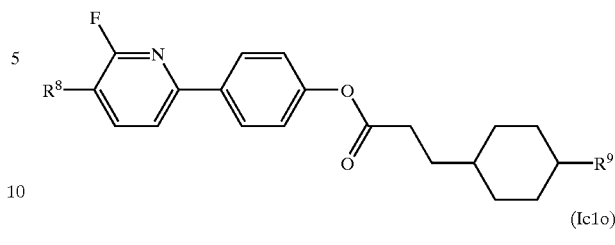

(Ic1o)
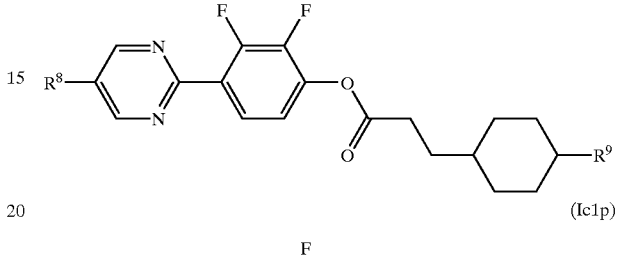

(Ic1n)
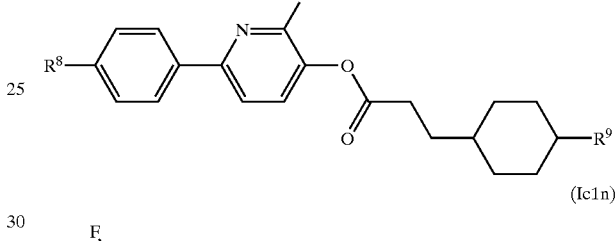

(Ic1o)
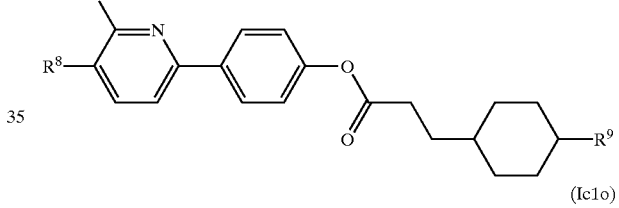

(Ic1p)
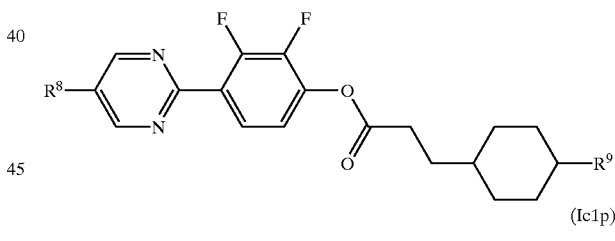

(Ic1p)
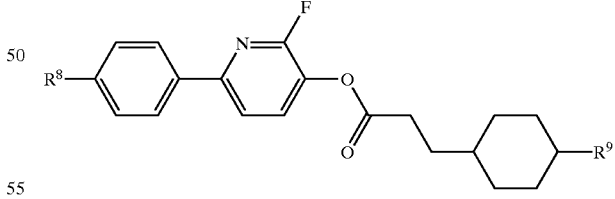

If desired, the formulae (Ia1ac) to (Ia1ak) above can also be excluded.

The liquid-crystal mixture of the display according to the invention preferably comprises, in addition to one or more compounds of the formula (I), 2 to 30 additional compounds selected as one or more representatives form the substance classes of the groups (II) to (XVII)

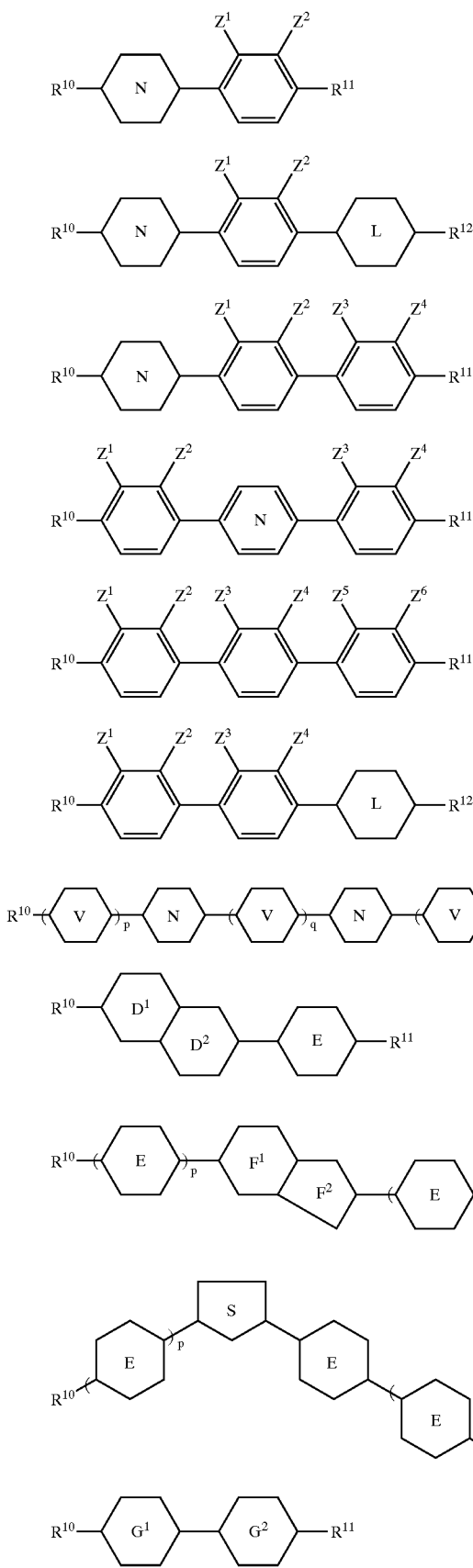
-continued
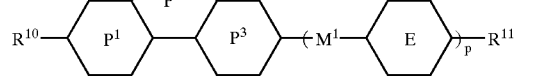
(XIII)
(XIV)
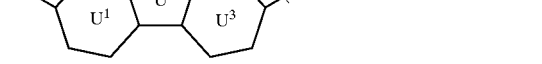
(XV)
(XVI)
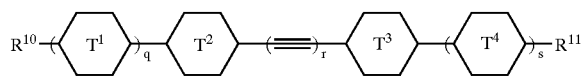
(XVII)
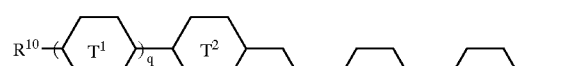
where:
$R^{10}$, $R^{11}$ are as defined for $R^1$, $R^2$ where additionally the terminal —CH$_3$— group may in each case be replaced by one of the chiral groups (optically active or racemic) below:
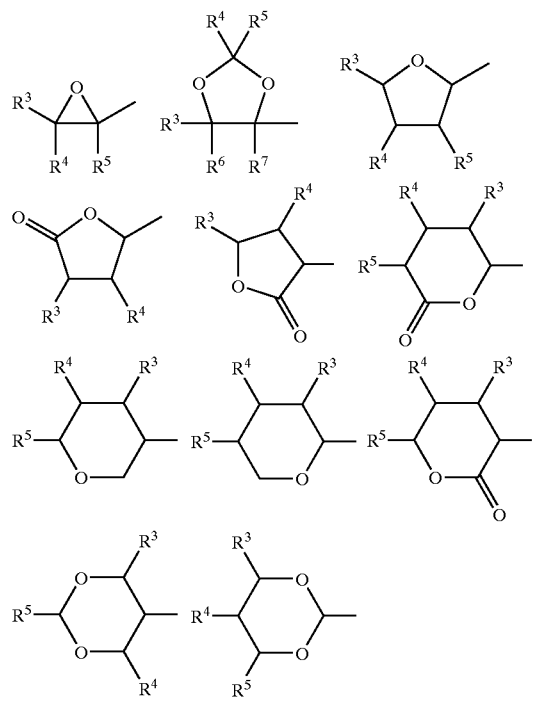

-continued

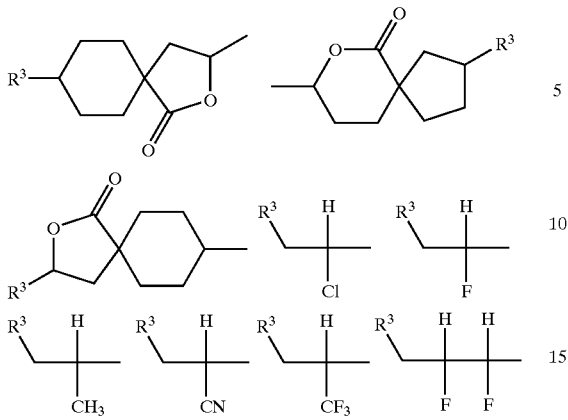

R³, R⁴, R⁵, R⁶, R⁷ are identical or different and are each
a) hydrogen
b) a straight-chain or branched alkyl radical (with or without asymmetric carbon atoms) having 1 to 16 carbon atoms, where
  b1) one or more nonadjacent and nonterminal $CH_2$ groups may be replaced by —O— and/or
  b2) one or two $CH_2$ groups may be replaced by —CH=CH—,
c) R⁴ and R⁵ together may alternatively be —(CH₂)₄— or —(CH₂)₅— if they are attached to an oxirane, dioxolane, tetrahydrofuran, tetrahydropyran, butyrolactone or valerolactone system;
$R^{12}$ is hydrogen or a straight-chain or branched alkyl radical (with or without asymmetric carbon atoms) having 1 to 16 carbon atoms, where one or more H may be replaced by F and one or two nonadjacent nonterminal —CH₂— groups may be replaced by —O—
$Z^1$, $Z^2$, $Z^3$, $Z^4$, $Z^5$, $Z^6$ are each, independently of one another, H or F

is a bivalent radical selected from the group consisting of pyridine-2,5-diyl, unsubstituted or monosubstituted by F, pyrimidine-2,5-diyl, unsubstituted or monosubstituted by F, pyrazine-2,5-diyl, unsubstituted or monosubstituted by F,

is a bivalent radical selected from the group consisting of naphthalene-2,6-diyl, in which one or two ring carbon atoms may be replaced by N and which can be monosubstituted or disubstituted by F or CN and in which $D^1$ or $D^2$ may also be a (saturated) alicycle

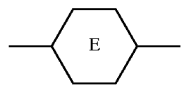

is a bivalent radical selected from the group consisting of phenylene-1,4-diyl, unsubstituted, monosubstituted or disubstituted by CN, or unsubstituted, monosubstituted, disubstituted, trisubstituted or tetra-substituted by F, pyridine-2,5-diyl, unsubstituted or monosubstituted by F, pyrimidine-2,5-diyl, unsubstituted or monosubstituted by F, cyclohexane-1,4-diyl

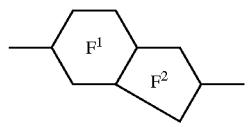

is a bivalent radical selected from the group consisting of indane-2,5-diyl, unsubstituted, monosubstituted or disubstituted by F in the aromatic ring, indan-1-one-2,6-diyl, unsubstituted, monosubstituted or disubstituted by F in the aromatic ring, benzothiazole-2,6-diyl, benzothiazole-2,5-diyl, benzo[b]thiophene-2,5-diyl, benzo[b]thiophene-2,6-diyl

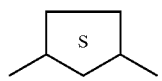

is a bivalent radical selected from the group consisting of (1,3,4)-thiadiazole-2,5-diyl, (1,3)-thiazole-2,5-diyl, thiophene-2,5-diyl, (1,3,4)-oxadiazole-2,5-diyl, (1,3)-oxazole-2,5-diyl, isoxazole-2,5-diyl

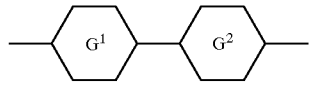

is a bivalent radical selected from the group consisting of 1,1'-biphenyl-4,4'-diyl, unsubstituted, monosubstituted or disubstituted by CN, or unsubstituted, monosubstituted, disubstituted, trisubstituted or tetra-substituted by F, 1,1'-phenylcyclohexyl-4,4'-diyl, 5,5'-pyridylpyrimidine-2,2'-diyl, unsubstituted or monosubstituted by F in one or both of the heterocycles, 5,2'-pyridylpyrimidine-2,5'-diyl, unsubstituted or monosubstituted by F in one or both of the heterocycles, 1,2'-phenyldioxane-4,5'-diyl, 1,2'-(2-fluorophenyl)dioxane-4,5'-diyl, 1,2'-(3-fluorophenyl)dioxane-4,5'-diyl, 1,2'-(2,3-difluorophenyl)dioxane-4,5'-diyl

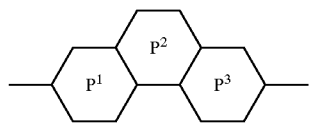

is a bivalent phenanthrene-2,7-diyl radical in which one or two ring carbon atoms may be replaced by N and which may be monosubstituted, disubstituted, trisubstituted or tetrasubstituted by F and in which P and/or P may be a (saturated) alicycle

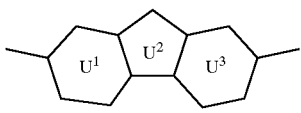

is a bivalent fluorene-2,7-diyl radical in which the —CH$_2$— group in U$^2$ may be replaced by —C(=O)—, —CHF— or —CF$_2$—

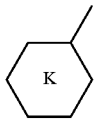

is a bivalent radical selected from the group consisting of phenylene-1,3-diyl, unsubstituted, monosubstituted or disubstituted by F, cyclohexane-1,3-diyl, unsubstituted or monosubstituted by F or CN, pyridine-2,6-diyl, pyridine-2,4-diyl, pyridine-3,5-diyl, pyridine-4,6-diyl, pyrimidine-4,6-diyl,

is a bivalent radical selected from the group consisting of cyclohexane-1,4-diyl, unsubstituted or monosubstituted by CN, CH$_3$, or disubstituted by F, cyclohex-1-ene-1,4-diyl, perfluorocyclohexane-1,4-diyl, cyclohex-2-ene-1,4-diyl, 1-alkyl-1-silacyclohexane-1,4-diyl, bicyclo[2.2.2]-octane-1,4-diyl.

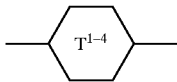

is a bivalent radical selected from the group consisting of phenylene-1,4-diyl, unsubstituted, monosubstituted or disubstituted by CN or F, naphthalene-2,6-diyl, in which one or two ring carbon atoms may be replaced by N and which may be monosubstituted or disubstituted by CN or F, cyclohexane-1,4-diyl, cyclohex-1-ene-1, 4-diyl, bicyclo[2.2.2]octane-1,4-diyl, (1,3)-dioxane-2, 5-diyl, pyridine-2,5-diyl, unsubstituted or monosubstituted by F, pyrimidine-2,5-diyl, unsubstituted or monosubstituted by F, (1,3,4)-thiadiazole-2,5-diyl, indane-2,5-diyl, unsubstituted, monosubstituted or disubstituted by F in the aromatic ring, thiophene-2,5-diyl

is a bivalent radical selected from the group consisting of phenylene-1,4-diyl, unsubstituted, monosubstituted or disubstituted by CN or F, naphthalene-2,6-diyl, in which one or two ring carbon atoms may be replaced by N and which may be monosubstituted or disubstituted by CN or F, cyclohexane-1,4-diyl, cyclohex-1-ene-1, 4-diyl, bicyclo[2.2.2]octane-1,4-diyl, (1,3)-dioxane-2, 5-diyl, indane-2,5-diyl, unsubstituted, monosubstituted or disubstituted by F in the aromatic ring, thiophene-2,5-diyl p, q, s are each zero or 1 r is 1 or 2.

The following meanings are preferred:

in (II),

is a bivalent radical selected from the group of pyridine-2, 5-diyl, unsubstituted or monosubstituted by F, pyrimidine-2,5-diyl, unsubstituted or monosubstituted by F Z$^1$, Z$^2$ are both H or both F R$^{10}$, R$^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals R$^{10}$, R$^{11}$ can be hydrogen in (III),

is a bivalent radical selected from the group consisting of pyridine-2,5-diyl, unsubstituted or monosubstituted by F, pyrimidine-2,5-diyl, unsubstituted or monosubstituted by F

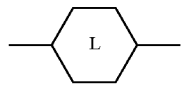

is a bivalent radical selected from the group consisting of cyclohexane-1,4-diyl, unsubstituted or monosubstituted by CN, cyclohex-1-ene-1,4-diyl, cyclohex-2-ene-1,4-diyl, Z$^1$, Z$^2$ are both H or both F, in (IV),

is a bivalent radical selected from the group consisting of pyridine-2,5-diyl, unsubstituted or monosubstituted by F, pyrimidine-2,5-diyl, unsubstituted or monosubstituted by F Z$^1$, Z$^2$ are both H or both F, Z$^3$, Z$^4$ are both H or both F in (V),

is a bivalent radical selected from the group consisting of pyridine-2,5-diyl, unsubstituted or monosubstituted by F, pyrimidine-2,5-diyl, unsubstituted or monosubstituted by F Z$^1$, Z$^2$ are both H or both F, Z$^3$, Z$^4$ are both H or F, with the proviso that Z$^1$, Z$^2$ and Z$^3$, Z$^4$ are not simultaneously F in (VI)

Z¹, Z², Z³, Z⁴, Z⁵, Z⁶ one element of this group is F or (Z¹ and Z²) or (Z³ and Z⁴) are both F in (VII), Z¹ and Z² are both H or both F; Z³ and Z⁴ are both H in (VIII)

is a bivalent radical selected from the group consisting of pyridine-2,5-diyl, unsubstituted or monosubstituted by F, pyrimidine-2,5-diyl, unsubstituted or monosubstituted by F

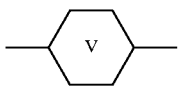

is a bivalent radical selected from the group consisting of phenylene-1,4-diyl, unsubstituted, monosubstituted or disubstituted by F, naphthalene-2,6-diyl, unsubstituted, monosubstituted or disubstituted by F, cyclohexane-1,4-diyl p, q, s are each zero or 1; their sum is zero or 1 in (IX),

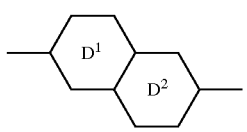

is naphthalene-2,6-diyl which can be monosubstituted or disubstituted by F

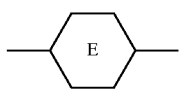

is a bivalent radical selected from the group consisting of phenylene-1,4-diyl, unsubstituted, monosubstituted or disubstituted by F, pyridine-2,5-diyl, unsubstituted or monosubstituted by F, pyrimidine-2,5-diyl, unsubstituted or monosubstituted by F in (X),

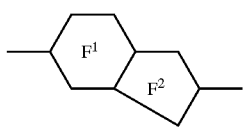

is a bivalent radical selected from the group consisting of indane-2,5-diyl, unsubstituted, monosubstituted or disubstituted by F in the aromatic ring, indan-1-one-2,6-diyl, and possibly benzothiazole-2,6-diyl

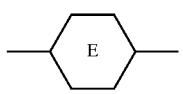

is a bivalent radical selected from the group consisting of phenylene-1,4-diyl, unsubstituted, monosubstituted or disubstituted by F, pyridine-2,5-diyl, unsubstituted or monosubstituted by F, pyrimidine-2,5-diyl, unsubstituted or monosubstituted by F p is 1 q is zero in (IX),

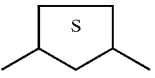

is (1,3,4)-thiadiazole-2,5-diyl

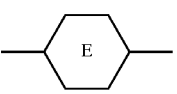

is a bivalent radical selected from the group consisting of phenylene-1,4-diyl, unsubstituted, monosubstituted or disubstituted by F, pyridine-2,5-diyl, unsubstituted or monosubstituted by F, pyrimidine-2,5-diyl, unsubstituted or monosubstituted by F, cyclohexane-1,4-diyl p is zero or 1 q is zero or 1, with the proviso that q is zero when p is 1 in (XII),

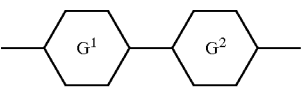

is a bivalent radical selected from the group consisting of 1,1'-biphenyl-4,4'-diyl, unsubstituted, monosubstituted or disubstituted by F, 1,1'-phenylcyclohexyl-4,4'-diyl, 5,5'-pyridylpyrimidine-2,2'-diyl, unsubstituted or monosubstituted by F in one or both of the heterocycles, 5,2'-pyridylpyrimidine-2,5'-diyl, unsubstituted or monosubstituted by F in one or both of the heterocycles in (XIII),

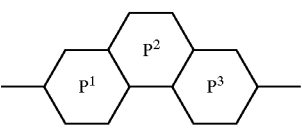

is a bivalent phenanthrene-2,7-diyl radical in which one or two ring carbon atoms may also be replaced by N and which may be monosubstituted or disubstituted by F and in which P² can be a (saturated) alicycle p is zero in (XIV),

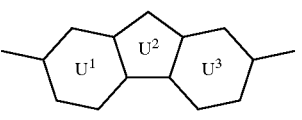

is a bivalent fluorene-2,7-diyl radical

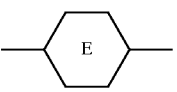

is a phenylene-2,4-diyl radical is zero or 1 in (XV),

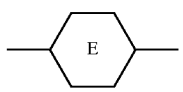

is a bivalent radical selected from the group consisting of phenylene-1,4-diyl, unsubstituted, monosubstituted or disubstituted by F, pyridine-2,5-diyl, unsubstituted or monosubstituted by F, pyrimidine-2,5-diyl, unsubstituted or monosubstituted by F

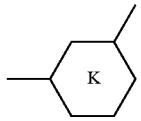

is a bivalent radical selected from the group consisting of phenylene-1,3-diyl, unsubstituted, monosubstituted or disubstituted by F p is zero or 1 in (XVI),

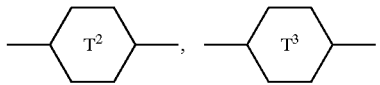

is a bivalent radical selected from the group consisting of phenylene-1,4-diyl, unsubstituted, monosubstituted or disubstituted by F, naphthalene-2,6-diyl, unsubstituted, monosubstituted or disubstituted by F

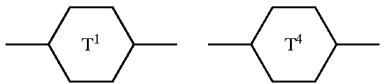

is a bivalent radical selected from the group consisting of phenylene-1,4-diyl, unsubstituted, monosubstituted or disubstituted by F, naphthalene-2,6-diyl, unsubstituted, monosubstituted or disubstituted by F, cyclohexane-1,4-diyl, pyridine-2,5-diyl, unsubstituted or monosubstituted by F, pyrimidine-2,5-diyl, unsubstituted or monosubstituted by F r is 1 q, s are each zero or 1, their sum being 1 in (XVII),

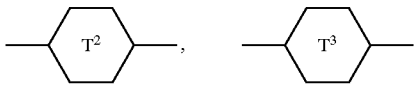

is a bivalent radical selected from the group consisting of phenylene-1,4-diyl, unsubstituted, monosubstituted or disubstituted by F, naphthalene-2,6-diyl, unsubstituted, monosubstituted or disubstituted by F, cyclohexane-1,4-diyl, pyridine-2,5-diyl, unsubstituted or monosubstituted by F, pyrimidine-2,5-diyl, unsubstituted or monosubstituted by F, (1,3,4)-thiadiazole-2,5-diyl, indane-2,5-diyl

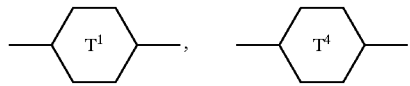

is a bivalent radical selected from the group consisting of phenylene-1,4-diyl, unsubstituted, monosubstituted or disubstituted by F, naphthalene-2,6-diyl, unsubstituted, monosubstituted or disubstituted by F, cyclohexane-1,4-diyl, cyclohex-1-ene-1,4-diyl, bicyclo-[2.2.2]octane-1,4-diyl, (1,3)-dioxane-2,5-diyl, pyridine-2,5-diyl, unsubstituted or monosubstituted by F, pyrimidine-2,5-diyl, unsubstituted or monosubstituted by F, (1,3,4)-thiadiazol-2,5-diyl, indane-2,5-diyl, unsubstituted, monosubstituted or disubstituted by F in the aromatic ring, thiophene-2,5-diyl q, s are each zero or 1; their sum being 0 or 1.

Particular preference is given to the following meanings:

in (II),

is pyridine-2,5-diyl, 2-fluoropyridine-3,6-diyl or pyrimidine-2,5-diyl $Z^1$, $Z^2$ are both H or both F $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen In (III),

is a bivalent radical selected from the group consisting of pyridine-2,5-diyl, 2-fluoropyridine-3,6-diyl, pyrimidine-2,5-diyl,

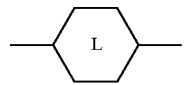

is cyclohexane-1,4-diyl, $Z^1$, $Z^2$ are both H or both F, $R^{10}$, $R^{11}$ are, independently of one another, identical of different and are each hydrogen or a straight-chain or branched alkyl or alkyloxy radical (with or without asymmetric carbon atoms) having 2–16 carbon atoms, where one or two nonterminal —CH$_2$— groups maybe replaced by —CH=CH—, —OC(=O)—, —C(=O)O— and one or more H atoms may be replaced by F with the proviso that only one of the radicals $R^{10}$, $R^{11}$ can be hydrogen.

In (IV),

is pyridine-2,5-diyl, 2-fluoropyridine-3,6-diyl, pyrimidine-2,5-diyl, $Z^1$, $Z^2$, $Z^3$, $Z^4$ are each H $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (V),

is pyridine-2,5-diyl, 2-fluoropyridine-3,6-diyl, pyrimidine-2,5-diyl, $Z^1$, $Z^2$, $Z^3$, $Z^4$ are each H $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (VI)

$Z^1$, $Z^2$, $Z^3$, $Z^4$, $Z^5$, $Z^6$ one element of this group is F or $Z^1$ and $Z^2$=F, $Z^3$, $Z^4$, $Z^5$, $Z^6$=H $Z^3$ and $Z^4$=F, $Z^1$, $Z^2$, $Z^5$, $Z^6$=H $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (VII), $Z^1$ and $Z^2$ are both F; $Z^3$ and $Z^4$ are both H $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (VIII),

is pyridine-2,5-diyl, pyrimidine-2,5-diyl

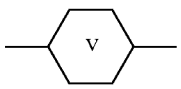

is phenylene-1,4-diyl, unsubstituted, monosubstituted or disubstituted by F, p, q, s are each zero or 1; their sum being zero or 1

$R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (IX),

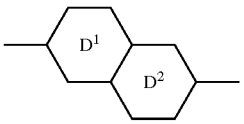

is naphthalene-2,6-diyl or 1-fluoronaphthalene-2,6-diyl

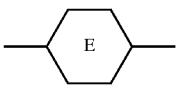

is phenylene-1,4-diyl, unsubstituted, monosubstituted or disubstituted by F, pyridine-2,5-diyl, 2-fluoropyridine-3,6-diyl, pyrimidine-2,5-diyl $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (X),

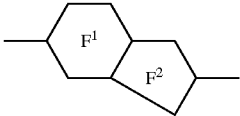

is benzothiazole-2,6-diyl, possibly also indane-2,5-diyl

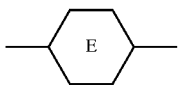

is phenylene-1,4-diyl, pyridine-2,5-diyl, pyrimidine-2,5-diyl p is 1 q is zero $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (IX),

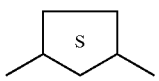

is (1,3,4)-thiadiazole-2,5-diyl

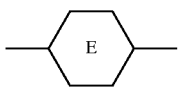

is phenylene-1,4-diyl, pyridine-2,5-diyl, cyclohexane-1,4-diyl p is zero or 1 q is zero or 1, with the proviso that q is zero when p is 1

$R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (XII),

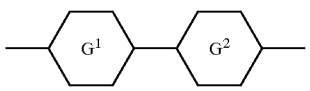

is a bivalent radical selected from the group consisting of 1,1'-biphenyl-4,4'-diyl, unsubstituted, monosubstituted or disubstituted by F, 1,1'-phenylcyclohexyl-4,4'-diyl, $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (XIII),

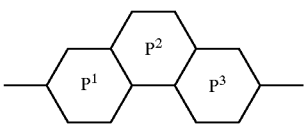

is phenanthrene-2,7-diyl, 1-fluorophenanthrene-2,7-diyl or 1,8-difluorophenanthrene-2,7-diyl, in which $P^2$ may alternatively be a (saturated) alicycle $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen p is zero.

In (XIV),

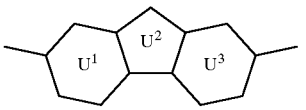

is a bivalent fluorene-2,7-diyl radical

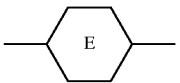

is a phenylene-2,4-diyl radical p is zero or 1

$R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH=CH—, —OC(=O)—, —C(=O)O— and one or more H atoms may be replaced by F with the proviso that only one of the radicals $R^{10}$, $R^{11}$ can be hydrogen.

In (XV),

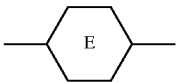

is phenylene-1,4-diyl, pyridine-2,5-diyl, pyrimidine-2,5-diyl,

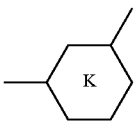

is phenylene-1,3-diyl p is 1

$R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH═CH—, —OC(═O)—, —C(═O)O— and one or more H atoms may be replaced by F with the proviso that only one of the radicals $R^{10}$, $R^{11}$ can be hydrogen.

In (XVI),

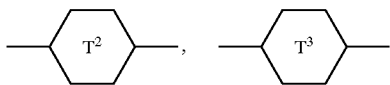

is phenylene-1,4-diyl, unsubstituted, monosubstituted or disubstituted by F, naphthalene-2,6-diyl, unsubstituted, monosubstituted or disubstituted by F

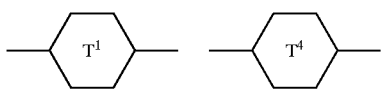

is phenylene-1,4-diyl, unsubstituted, monosubstituted or disubstituted by F, cyclohexane-1,4-diyl, pyridine-2,5-diyl, 2-fluoropyridine-3,6-diyl, pyrimidine-2,5-diyl r is 1 q, s are each zero or 1, their sum being 1

$R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH═CH—, —OC(═O)—, —C(═O)O— and one or more H atoms may be replaced by F with the proviso that only one of the radicals $R^{10}$, $R^{11}$ can be hydrogen.

In (XVII),

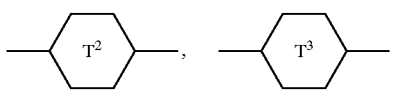

is phenylene-1,4-diyl, unsubstituted, monosubstituted or disubstituted by F, cyclohexane-1,4-diyl, pyridine-2,5-diyl, pyrimidine-2,5-diyl, (1,3,4)-thiadiazole-2,5-diyl

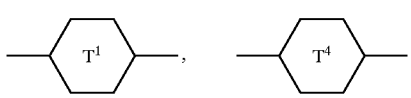

is phenylene-1,4-diyl, unsubstituted, monosubstituted or disubstituted by F, cyclohexane-1,4-diyl, pyridine-2,5-diyl, 2-fluoropyridine-3,6-diyl, pyrimidine-2,5-diyl, (1,3,4)-thiadiazole-2,5-diyl q, s are each zero or 1; their sum being 0 or 1

$R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH═CH—, —OC(═O)—, —C(═O)O— and one or more H atoms may be replaced by F with the proviso that only one of the radicals $R^{10}$, $R^{11}$ can be hydrogen.

The liquid-crystal mixture preferably consists of 3–30 compounds and comprises at least one compound of the formula (I) and at least one compound of the formula (II) and, if desired, at least one compound of the formula (III).

Preferably, the liquid-crystal mixture additionally comprises at least one compound selected from the groups (IV), (V), (VI), (VII).

Particularly preferably, the liquid-crystal mixture additionally comprises at least one compound selected from the groups (VIII), (IX), (XII), (XVI), (XVII). Likewise particularly preferably, the liquid-crystal mixture additionally comprises at least one compound selected from the groups (X), (XI), (XIV), (XV).

The liquid-crystal mixture may also comprise at least one compound of the formula (XIII).

Preferably, the mixture additionally comprises at least one compound selected from the group (I) to (XVII), where $R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —CH$_2$— groups may be replaced by —CH═CH—, —OC(═O)—, —C(═O)O— and one or more H atoms may be replaced by F with the proviso that only one of the radicals $R^{10}$, $R^{11}$ can be hydrogen and where, in addition, the terminal —CH$_3$— group in at least one of $R^{10}$, $R^{11}$ is replaced by one of the following chiral groups (optically active):

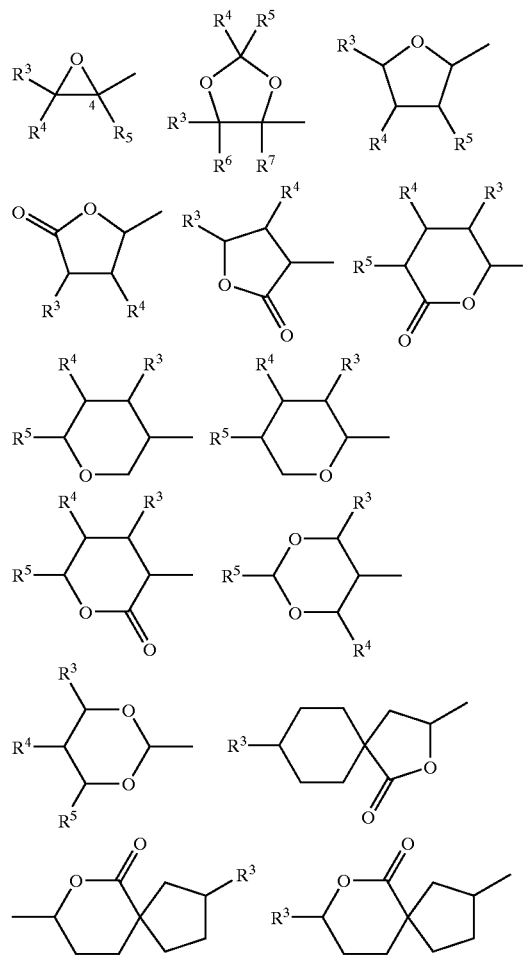

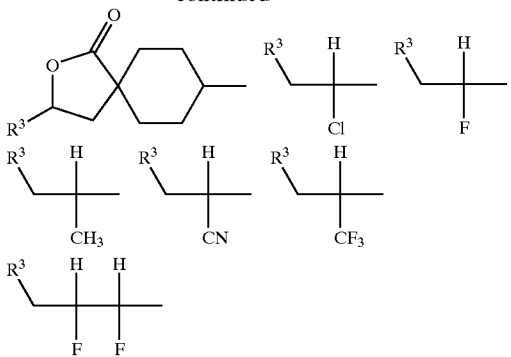

$R^3$, $R^4$, $R^5$, $R^6$, $R^7$ are identical or different and are each
a) hydrogen
b) a straight-chain or branched alkyl radical (with or without asymmetric carbon atoms) having 1 to 16 carbon atoms, where
   b1) one or more nonadjacent and nonterminal $CH_2$ groups may be replaced by —O— and/or
   b2) one or two $CH_2$ groups may be replaced by —CH=CH—,
c) $R^4$ and $R^5$ together may alternatively be —$(CH_2)_4$— or —$(CH_2)_5$— if they are attached to an oxirane, dioxolane, tetrahydrofuran, tetrahydropyran, butyrolactone or valerolactone system.

Particularly preferably, the mixture comprises 1 to 5 compounds selected from the group (I) to (XVII), where
$R^{10}$, $R^{11}$ are, independently of one another, identical or different and are each hydrogen or a straight-chain or branched alkyl or alkyloxy radical (with or without asymmetric carbon atoms) having 2–16 carbon atoms, where one or two nonterminal —$CH_2$— groups may be replaced by —CH=CH—, —OC(=O)—, —C(=O)O— and one or more H atoms may be replaced by F with the proviso that only one of the radicals $R^{10}$, $R^{11}$ can be hydrogen and where, in addition, the terminal —$CH_3$— group in at least one of $R^{10}$, $R^{11}$ is replaced by one of the following chiral groups (optically active):

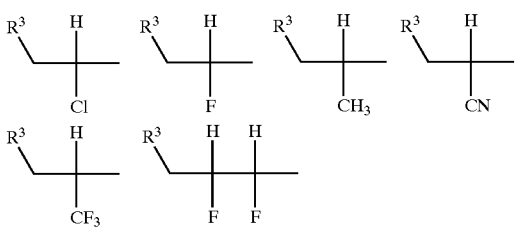

$R^3$ is hydrogen or a straight-chain or branched alkyl radical (with or without asymmetric carbon atoms) having 1 to 16 carbon atoms.

Preference is given to liquid-crystal mixtures of the invention which comprise 3 to 25 components, including
  1 to 15 compounds of the formula (I)
  1 to 15 compounds of the formula (II)
  1 to 7 compounds of the formula (III).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (III)
  1 to 7 compounds of the formula (IV).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (III)
  1 to 7 compounds of the formula (IV)
  1 to 7 compounds of the formula (V).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (III)
  1 to 7 compounds of the formula (IV)
  1 to 7 compounds of the formula (V)
  1 to 7 compounds of the formula (VI).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (III)
  1 to 7 compounds of the formula (IV)
  1 to 7 compounds of the formula (VI)
  1 to 7 compounds of the formula (VII).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (III)
  1 to 7 compounds of the formula (IV)
  1 to 7 compounds of the formula (VI).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (III)
  1 to 7 compounds of the formula (IV)
  1 to 7 compounds of the formula (VI)
  1 to 7 compounds of the formula (XII).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (III)
  1 to 7 compounds of the formula (IV)
  1 to 7 compounds of the formula (V)
  1 to 7 compounds of the formula (VI)
  1 to 7 compounds of the formula (VII).

Preference is furthermore given to liquid-crystal mixtures of the invention which comprise 3 to 25 components, including
  1 to 15 compounds of the formula (I)
  1 to 15 compounds of the formula (II)
  1 to 7 compounds of the formula (IV).

Preference is furthermore given to liquid-crystal mixtures of the invention which comprise 3 to 25 components, including 1 to 15 compounds of the formula (I)
1 to 15 compounds of the formula (II)
1 to 7 compounds of the formula (IV)
1 to 7 compounds of the formula (VI).

Preference is furthermore given to liquid-crystal mixtures of the invention which comprise 3 to 25 components, including 1 to 15 compounds of the formula (I)
1 to 15 compounds of the formula (II)
1 to 7 compounds of the formula (IV)
1 to 7 compounds of the formula (XII).

Preference is furthermore given to liquid-crystal mixtures of the invention which comprise 3 to 25 components, including 1 to 15 compounds of the formula (I)
1 to 15 compounds of the formula (II)
1 to 7 compounds of the formula (IV)
1 to 7 compounds of the formula (IX).

Particular preference is given to liquid-crystal mixtures of the invention which comprise 3 to 25 components, including 1 to 12 compounds of the formula (I)
2 to 12 compounds of the formula (II)
1 to 5 compounds of the formula (III).

Particular preference is given to liquid-crystal mixtures of the invention which comprise 3 to 25 components, including 1 to 12 compounds of the formula (I)
2 to 12 compounds of the formula (II)
1 to 5 compounds of the formula (III)
1 to 5 compounds of the formula (IV)
1 to 5 compounds of the formula (VI)
1 to 5 compounds of the formula (VII).

Particular preference is given to liquid-crystal mixtures of the invention which comprise 3 to 25 components, including 1 to 12 compounds of the formula (I)
2 to 12 compounds of the formula (II)
1 to 5 compounds of the formula (III)
1 to 5 compounds of the formula (IV)
1 to 5 compounds of the formula (VI).

Particular preference is given to liquid-crystal mixtures of the invention which comprise 3 to 25 components, including 1 to 12 compounds of the formula (I)
2 to 12 compounds of the formula (II)
1 to 5 compounds of the formula (III)
1 to 5 compounds of the formula (IV)
1 to 5 compounds of the formula (VI)
1 to 5 compounds of the formula (XII).

Particular preference is given to liquid-crystal mixtures of the invention which comprise 3 to 25 components, including 1 to 12 compounds of the formula (I)
2 to 12 compounds of the formula (II)
1 to 5 compounds of the formula (IV).

Particular preference is given to liquid-crystal mixtures of the invention which comprise 3 to 25 components, including 1 to 12 compounds of the formula (I)
2 to 12 compounds of the formula (II)
1 to 5 compounds of the formula (IV)
1 to 5 compounds of the formula (VI).

Particular preference is given to liquid-crystal mixtures of the invention which comprise 3 to 25 components, including 1 to 12 compounds of the formula (I)
2 to 12 compounds of the formula (II)
1 to 5 compounds of the formula (IV)
1 to 5 compounds of the formula (VI)
1 to 5 compounds of the formula (VII).

Very particular preference is given to liquid-crystal mixtures of the invention which comprise 3 to 23 components, including 1 to 8 compounds of the formula (I)
2 to 10 compounds of the formula (II)
1 to 3 compounds of the formula (III).

Very particular preference is furthermore given to liquid-crystal mixtures of the invention which comprise 3 to 23 components, including 1 to 8 compounds of the formula (I)
2 to 10 compounds of the formula (II), in which, in at least one compound, a —CH$_2$-group is replaced by —OC(=O)—
1 to 3 compounds of the formula (III).

According to one embodiment of the invention, very particular preference is furthermore given to mixtures of the invention which comprise 3 to 30 components, including 4 to 8 compounds of the formula (I)
1 to 10 compounds of the formula (II)
1 to 4 compounds of the formula (VI)
1 to 4 compounds of the formula (X)
1 to 4 compounds of the formula (XI).

In a particular embodiment of this very particularly preferred mixture, the mixture comprises at least one compound of the formula (Ia), at least one compound of the formula (Ib), at least 3 compounds of the formula (II) and at least one compound of each of the formulae (VI), (X) and (XI).

In a most preferred embodiment, said at least one compound of the formula (Ia) and at least one compound of the formula (Ib) include at least one compound of the formula (IaIh) and at least one compound of the formula (IaIv) and at least one compound of the formula (IbIa), where in (II)

is pyrimidine-2,5-diyl, in (VI), Z$^1$ and Z$^2$ are each F, in (X),

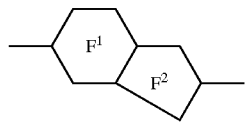

in benzothiazole-2,6-diyl, and in (XI),

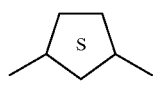

is thiazole-2,5-diyl.

According to one embodiment of the invention, very particular preference is furthermore given to mixtures of the invention which comprise 3 to 30 components, including 4 to 8 compounds of the formula (I)
1 to 10 compounds of the formula (II)
1 to 4 compounds of the formula (IV)
1 to 4 compounds of the formula (VI)
1 to 4 compounds of the formula (X)
1 to 4 compounds of the formula (XI).

In a special embodiment of this very particularly preferred mixture, the mixture comprises at least one compound of the formula (Ia), at least one compound of the formula (Ib), at least three compounds of the formula (II) and at least one compound of each of the formulae (IV), (VI), (X) and (XI).

In a most preferred embodiment, said at least one compound of the formula (Ia) and one compound of the formula (Ib) include at least 1 compound of the formula (IaIh) and at least 1 compound of the formula (IaIv) and, if desired, at least one compound of the formula (IaIn) and at least 1 compound of the formula (IbIa), where, in (II),

is pyrimidine-2,5-diyl, in (IV)

is pyrimidine-2,5-diyl, pyridine-2,5-diyl or 2-fluoropyridine-3,6-diyl, in (VI), $Z^1$ and $Z^2$ are each F, in (X),

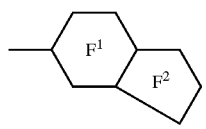

is benzothiazole-2,6-diyl, and, in (XI),

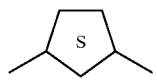

is thiazole-2,5-diyl.

In a particular embodiment of the very particularly preferred liquid-crystal mixture, in (II)

is pyrimidine-2,5-diyl,
$Z^1$, $Z^2$ are both H or both F,
$R^{10}$ is a straight-chain or branched alkyl or alkyloxy radical having 6 to 14 carbon atoms, where one or two —CH$_2$-groups may be replaced by —O— and/or —C(=O)—,
$R^{11}$ is a straight-chain or branched alkyl or alkyloxy radical having 6 to 14 carbon atoms, where one or two —CH$_2$-groups may be replaced by —O— and/or —C(=O)—, (III)

is 2-fluoro-pyridine-3,6-diyl

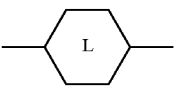

is cyclohexane-1,4-dily
$R^{10}$ is a straight-chain or branched alkyl or alkyloxy radical having 6 to 14 carbon atoms, where one or two —CH$_2$-groups may be replaced by —O— and/or —C(=O)— and one H atom may be replaced by F
$R^{12}$ is hydrogen or a straight-chain or branched alkyl or alkyloxy radical having 6 to 14 carbon atoms, where one or two —CH$_2$— groups may be replaced by —O— and/or —C(=O)—.

In a very particular embodiment of the very particularly preferred liquid-crystal mixture, (II) is 5-alkyl-2-(4-alkyloxyphenyl)pyrimidine, 5-alkyl-2-(4-alkylcarbonyloxyphenyl)pyrimidine, 5-alkylcarbonyloxy-2-(4-alkyloxyphenyl)pyrimidine or 5-alkyl-2-(4-alkyloxy-2,3-difluorophenyl)pyrimidine and, (III) $R^{10}$ is a straight-chain alkyloxy radical having 6 to 14 carbon atoms, where one H atom is replaced by F
$R^{12}$ is hydrogen.

The chiralsmectic liquid-crystalline mixture preferably comprises 10–60% of one or more compounds of the formula (I). The mixture particularly preferably comprises 10–60% of 1–15 compounds of the formula (I). The mixture particularly preferably comprises 10–60% of 1–15 compounds of the formula (I) and 40–90% of 2–15 compounds of the formula (II). In particular, the mixture comprises 10–60% of 1–15 compounds of the formula (I), 40–90% of 2–15 compounds of the formula (II) and 1–40% of 1–15 compounds from the group (III), (IV), (V), (VI) and (VII), the total amount being 100%. The percentages are by weight.

The invention furthermore provides compounds of the general formula (I), selected from the compounds of the formula (XX), where

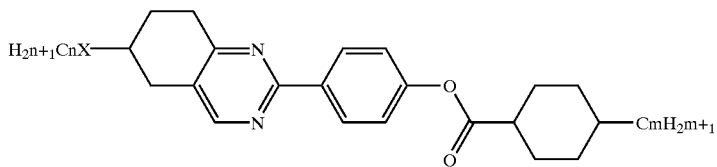

| n | 2 | 2 | 2 | 2 | 2 | 2 | 2 | 2 | 3 | 3 | 3 | 3 | 3 | 3 | 3 | 3 | 4 | 4 | 4 | 4 | 4 | 4 | 4 | 4 |
|---|---|---|---|---|---|---|---|---|---|---|---|---|---|---|---|---|---|---|---|---|---|---|---|---|
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | — | — | — | — | — | — | — | — | — | — | — | — | — | — | — | — | — | — | — | — | — | — | — | — |
| n | 5 | 5 | 5 | 5 | 5 | 5 | 5 | 6 | 6 | 6 | 6 | 6 | 6 | 6 | 6 | 7 | 7 | 7 | 7 | 7 | 7 | 7 | 7 | 8 |
| m | 3 | 5 | 6 | 7 | 8 | 9 | 10 | 3 | 4 | 5 | 6 | 7 | 8 | 9 | 10 | 3 | 4 | 5 | 6 | 7 | 8 | 9 | 10 | 3 |
| X | — | — | — | — | — | — | — | — | — | — | — | — | — | — | — | — | — | — | — | — | — | — | — | — |
| n | 8 | 8 | 8 | 8 | 8 | 8 | 8 | 9 | 9 | 9 | 9 | 9 | 9 | 9 | 9 | 10 | 10 | 10 | 10 | 10 | 10 | 10 | | |
| m | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 | |
| X | — | — | — | — | — | — | — | — | — | — | — | — | — | — | — | — | — | — | — | — | — | — | | |
| n | 2 | 2 | 2 | 2 | 2 | 2 | 2 | 2 | 3 | 3 | 3 | 3 | 3 | 3 | 3 | 3 | 4 | 4 | 4 | 4 | 4 | 4 | 4 | 4 |
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | O | O | O | O | O | O | O | O | O | O | O | O | O | O | O | O | O | O | O | O | O | O | O | O |
| n | 5 | 5 | 5 | 5 | 5 | 5 | 5 | 5 | 6 | 6 | 6 | 6 | 6 | 6 | 6 | 6 | 7 | 7 | 7 | 7 | 7 | 7 | 7 | 7 |
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | O | O | O | O | O | O | O | O | O | O | O | O | O | O | O | O | O | O | O | O | O | O | O | O |
| n | 8 | 8 | 8 | 8 | 8 | 8 | 8 | 8 | 9 | 9 | 9 | 9 | 9 | 9 | 9 | 9 | 10 | 10 | 10 | 10 | 10 | 10 | 10 | 10 |
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | O | O | O | O | O | O | O | O | O | O | O | O | O | O | O | O | O | O | O | O | O | O | O | O |

Compounds of the formula (XXI), where:

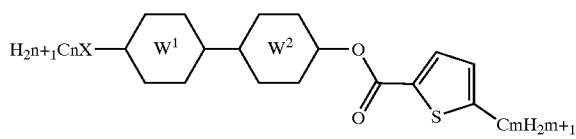

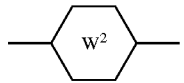

is 2-fluoropyridine-3,6-diyl, 4-fluoropyrimidine-2,5-diyl or phenylene-1,4-diyl or possibly pyridine-2,5-diyl, unsubstituted, monosubstituted or disubstituted by F with the provisos that a) one of the rings $W^1/W^2$ must be one of the nitrogen-containing heterocycles and n and m are preferably from 1 to 14 and X is —O— or a single bond. n can alternatively be an integer from 2 to 10 and m can be an integer from 3 to 10 or preferably b) the grasping $W^1$—$W^2$ is undirected and is 3-fluorobiphenyl-4,4'-diyl or 2-fluorobiphenyl-4,4'-diyl, where n, m and X are as defined below c) the grasping $W^1$—$W^2$ is undirected and is 2,3-difluorobiphenyl-4,4'-diyl, where n and m are from 1 to 14 and X is —O— or a single bond.

is 2-fluoropyridine-3,6-diyl, 4-fluoropyrimidine-2,5-diyl or phenylene-1,4-diyl or possibly pyridine-2,5-diyl, unsubstituted, monosubstituted or disubstituted by F

| n | 2 | 2 | 2 | 2 | 2 | 2 | 2 | 2 | 3 | 3 | 3 | 3 | 3 | 3 | 3 | 3 | 4 | 4 | 4 | 4 | 4 | 4 | 4 | 4 |
|---|---|---|---|---|---|---|---|---|---|---|---|---|---|---|---|---|---|---|---|---|---|---|---|---|
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | — | — | — | — | — | — | — | — | — | — | — | — | — | — | — | — | — | — | — | — | — | — | — | — |
| n | 5 | 5 | 5 | 5 | 5 | 5 | 5 | 5 | 6 | 6 | 6 | 6 | 6 | 6 | 6 | 6 | 7 | 7 | 7 | 7 | 7 | 7 | 7 | 7 |
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | — | — | — | — | — | — | — | — | — | — | — | — | — | — | — | — | — | — | — | — | — | — | — | — |
| n | 8 | 8 | 8 | 8 | 8 | 8 | 8 | 8 | 10 | 10 | 10 | 10 | 10 | 10 | 10 | 10 | | | | | | | | |
| m | 3 | 4 | 5 | 6 | 7 | 8 | 9 | 10 | 3 | 4 | 5 | 6 | 7 | 8 | 9 | 10 | | | | | | | | |
| X | — | — | — | — | — | — | — | — | — | — | — | — | — | — | — | — | | | | | | | | |
| n | 2 | 2 | 2 | 2 | 2 | 2 | 2 | 2 | 3 | 3 | 3 | 3 | 3 | 3 | 3 | 3 | 4 | 4 | 4 | 4 | 4 | 4 | 4 | 4 |
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | O | O | O | O | O | O | O | O | O | O | O | O | O | O | O | O | O | O | O | O | O | O | O | O |
| n | 5 | 5 | 5 | 5 | 5 | 5 | 5 | 5 | 6 | 6 | 6 | 6 | 6 | 6 | 6 | 6 | 7 | 7 | 7 | 7 | 7 | 7 | 7 | 7 |
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | O | O | O | O | O | O | O | O | O | O | O | O | O | O | O | O | O | O | O | O | O | O | O | O |

-continued
| n | 9 | 9 | 9 | 9 | 9 | 9 | 9 | 9 | 10 | 10 | 10 | 10 | 10 | 10 | 10 | 10 |
|---|---|---|---|---|---|---|---|---|----|----|----|----|----|----|----|----|
| m | 3 | 4 | 5 | 6 | 7 | 8 | 9 | 10 | 3 | 4 | 5 | 6 | 7 | 8 | 9 | 10 |
| X | O | O | O | O | O | O | O | O | O | O | O | O | O | O | O | O |
Further possible combinations are n=9, m=3–10, X=—
and n=8, m=3–10, X=0.
Compounds of the formula (XXII), where:
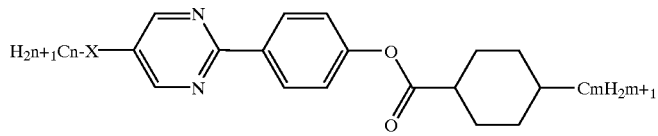
| n | 8 | 8 | 8 | 8 | 8 | 8 | 9 | 9 | 9 | 9 | 9 | 9 | 9 | 9 | 9 | 10 | 10 | 11 | 12 | 13 | 13 | 13 | 13 | 13 |
|---|---|---|---|---|---|---|---|---|---|---|---|---|---|---|---|----|----|----|----|----|----|----|----|----|
| m | 6 | 7 | 8 | 9 | 10 | 11 | 3 | 4 | 5 | 6 | 7 | 8 | 9 | 10 | 11 | 6 | 11 | 6 | 6 | 4 | 5 | 6 | 7 | 8 |
| X | — | — | — | — | — | — | — | — | — | — | — | — | — | — | — | — | — | — | — | — | — | — | — | — |
| n | 13 | 13 | 13 | 14 | 14 | 14 | 14 | 14 | 14 | 7 | 7 | 7 | 7 | 7 | 7 | 7 | 7 | 7 | 8 | 8 | 8 | 8 | | |
| m | 9 | 10 | 11 | 5 | 6 | 7 | 9 | 10 | 11 | 3 | 4 | 5 | 6 | 7 | 8 | 9 | 10 | 11 | 4 | 7 | 8 | 9 | | |
| X | — | — | — | — | — | — | — | — | — | O | O | O | O | O | O | O | O | O | O | O | O | O | | |
| n | 8 | 8 | 9 | 9 | 9 | 9 | 9 | 9 | 9 | 9 | 9 | 10 | 10 | 10 | 10 | 10 | 10 | 10 | 11 | 11 | 11 | | | |
| m | 10 | 11 | 11 | 3 | 4 | 6 | 7 | 8 | 9 | 10 | 11 | 3 | 6 | 7 | 8 | 9 | 10 | 11 | 3 | 4 | 6 | | | |
| X | O | O | O | O | O | O | O | O | O | O | O | O | O | O | O | O | O | O | O | O | O | | | |
| n | 11 | 11 | 11 | 11 | 11 | 12 | 12 | 12 | 12 | 12 | 12 | 12 | 12 | 13 | 13 | 13 | 13 | 13 | 13 | 13 | 13 | 13 | 14 | 14 |
| m | 7 | 8 | 9 | 10 | 11 | 3 | 4 | 6 | 7 | 8 | 9 | 10 | 11 | 3 | 4 | 5 | 6 | 7 | 8 | 9 | 10 | 11 | 3 | 4 |
| X | O | O | O | O | O | O | O | O | O | O | O | O | O | O | O | O | O | O | O | O | O | O | O | O |
| n | 14 | 14 | 14 | 14 | 14 | 14 | 14 | | | | | | | | | | | | | | | | | |
| m | 5 | 6 | 7 | 8 | 9 | 10 | 11 | | | | | | | | | | | | | | | | | |
| X | O | O | O | O | O | O | O | | | | | | | | | | | | | | | | | |
Compounds of the formula (XXIII), where:
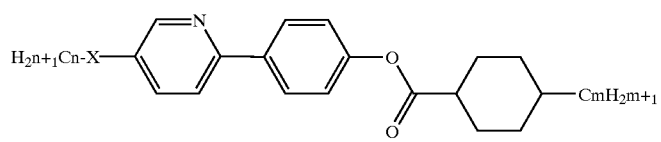
| n | 9 | 9 | 9 | 9 | 9 | 9 | 9 | 9 | 9 | 10 | 10 | 10 | 10 | 10 | 10 | 10 | 10 | 10 | 11 | 11 | 11 | 11 | 11 | 11 | 11 |
|---|---|---|---|---|---|---|---|---|---|----|----|----|----|----|----|----|----|----|----|----|----|----|----|----|----|
| m | 3 | 4 | 5 | 6 | 7 | 8 | 9 | 10 | 11 | 3 | 4 | 6 | 7 | 8 | 9 | 10 | 11 | 12 | 5 | 6 | 7 | 8 | 9 | 10 | 11 |
| X | — | — | — | — | — | — | — | — | — | — | — | — | — | — | — | — | — | — | — | — | — | — | — | — | — |
| n | 12 | 12 | 12 | 12 | 12 | 12 | 12 | 13 | 13 | 13 | 13 | 13 | 13 | 13 | 13 | 13 | 14 | 14 | 14 | 14 | 14 | 14 | | | |
| m | 4 | 6 | 7 | 8 | 9 | 10 | 11 | 3 | 4 | 5 | 6 | 7 | 8 | 9 | 10 | 11 | 3 | 4 | 5 | 6 | 7 | 8 | | | |
| X | — | — | — | — | — | — | — | — | — | — | — | — | — | — | — | — | — | — | — | — | — | — | | | |
| n | 14 | 14 | 14 | 14 | 6 | 6 | 6 | 6 | 6 | 6 | 6 | 6 | 6 | 7 | 7 | 7 | 7 | 7 | 7 | 7 | 7 | 7 | 8 | 8 | |
| m | 9 | 10 | 11 | 12 | 3 | 4 | 5 | 6 | 7 | 8 | 9 | 10 | 11 | 12 | 3 | 4 | 5 | 6 | 7 | 8 | 9 | 10 | 11 | 12 | 3 | 4 |
| X | — | — | — | — | O | O | O | O | O | O | O | O | O | O | O | O | O | O | O | O | O | O | O | O |
| n | 8 | 8 | 8 | 8 | 8 | 8 | 8 | 9 | 9 | 9 | 9 | 9 | 9 | 9 | 9 | 9 | 10 | 10 | 10 | 10 | 10 | 10 | 10 | 10 | |
| m | 5 | 7 | 8 | 9 | 10 | 11 | 12 | 3 | 4 | 5 | 6 | 7 | 8 | 9 | 10 | 11 | 12 | 3 | 4 | 5 | 6 | 7 | 8 | 9 | 10 | 11 |
| X | O | O | O | O | O | O | O | O | O | O | O | O | O | O | O | O | O | O | O | O | O | O | O | O |
| n | 11 | 11 | 11 | 11 | 11 | 11 | 11 | 11 | 11 | 12 | 12 | 12 | 12 | 12 | 12 | 12 | 12 | 12 | 13 | 13 | 13 | 13 | 13 | 13 | |
| m | 3 | 4 | 5 | 6 | 7 | 8 | 9 | 10 | 11 | 12 | 3 | 4 | 5 | 6 | 7 | 8 | 9 | 10 | 11 | 12 | 3 | 4 | 5 | 6 | 7 | 8 |
| x | O | O | O | O | O | O | O | O | O | O | O | O | O | O | O | O | O | O | O | O | O | O | O | O |

Compounds of the formula (XXIV), where:
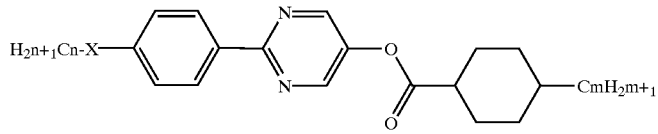
| n | 8 | 8 | 8 | 8 | 8 | 8 | 8 | 8 | 8 | 9 | 9 | 9 | 9 | 9 | 9 | 9 | 9 | 9 | 10 | 10 | 10 | 10 | 10 | 10 |
|---|---|---|---|---|---|---|---|---|---|---|---|---|---|---|---|---|---|---|---|---|---|---|---|---|
| m | 3 | 4 | 5 | 6 | 7 | 8 | 9 | 10 | 11 | 3 | 4 | 5 | 6 | 7 | 8 | 9 | 10 | 11 | 3 | 4 | 5 | 6 | 7 | 8 |
| X | — | — | — | — | — | — | — | — | — | — | — | — | — | — | — | — | — | — | — | — | — | — | — | — |
| n | 10 | 10 | 10 | 11 | 11 | 11 | 11 | 11 | 11 | 11 | 12 | 12 | 12 | 12 | 12 | 12 | 12 | 12 | 12 | 13 | 13 | 13 | 13 | 13 |
| m | 9 | 10 | 11 | 4 | 6 | 7 | 8 | 9 | 10 | 11 | 3 | 4 | 5 | 6 | 7 | 8 | 9 | 10 | 11 | 3 | 4 | 5 | 6 | 7 |
| X | — | — | — | — | — | — | — | — | — | — | — | — | — | — | — | — | — | — | — | — | — | — | — | — |
| n | 13 | 13 | 13 | 13 | 14 | 14 | 14 | 14 | 14 | 14 | 14 | 14 | 14 | | | | | | | | | | | |
| m | 8 | 9 | 10 | 11 | 3 | 4 | 5 | 6 | 7 | 8 | 9 | 10 | 11 | | | | | | | | | | | |
| X | — | — | — | — | — | — | — | — | — | — | — | — | — | | | | | | | | | | | |
Compounds of the formula (XXV), where:
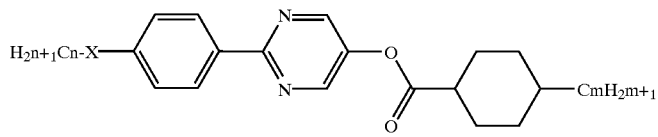
| n | 2 | 2 | 2 | 2 | 2 | 2 | 2 | 2 | 3 | 3 | 3 | 3 | 3 | 3 | 3 | 3 | 4 | 4 | 4 | 4 | 4 | 4 | 4 | 4 |
|---|---|---|---|---|---|---|---|---|---|---|---|---|---|---|---|---|---|---|---|---|---|---|---|---|
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | O | O | O | O | O | O | O | O | O | O | O | O | O | O | O | O | O | O | O | O | O | O | O | O |
| n | 4 | 3 | 3 | 3 | 3 | 3 | 3 | 3 | 3 | 4 | 4 | 4 | 4 | 4 | 4 | 4 | 4 | 5 | 5 | 5 | 5 | 5 | 5 | 5 |
| m | 11 | 3 | 4 | 5 | 6 | 7 | 8 | 9 | 10 | 11 | 3 | 4 | 5 | 6 | 7 | 8 | 9 | 10 | 11 | 3 | 4 | 6 | 7 | 8 |
| X | O | O | O | O | O | O | O | O | O | O | O | O | O | O | O | O | O | O | O | O | O | O | O | O |
| n | 5 | 5 | 5 | 6 | 6 | 6 | 6 | 6 | 6 | 6 | 6 | 6 | 7 | 7 | 7 | 7 | 7 | 7 | 7 | 7 | 7 | 8 | 8 | 8 |
| m | 9 | 10 | 11 | 3 | 4 | 5 | 6 | 7 | 8 | 9 | 10 | 11 | 3 | 4 | 5 | 6 | 7 | 8 | 9 | 10 | 11 | 3 | 4 | 5 |
| X | O | O | O | O | O | O | O | O | O | O | O | O | O | O | O | O | O | O | O | O | O | O | O | O |
| n | 8 | 8 | 8 | 8 | 8 | 8 | 9 | 9 | 9 | 9 | 9 | 9 | 9 | 9 | 10 | 10 | 10 | 10 | 10 | 10 | 10 | 10 | 10 | 10 |
| m | 6 | 7 | 8 | 9 | 10 | 11 | 3 | 4 | 5 | 6 | 7 | 8 | 9 | 10 | 11 | 3 | 4 | 5 | 6 | 7 | 8 | 9 | 10 | 11 |
| X | O | O | O | O | O | O | O | O | O | O | O | O | O | O | O | O | O | O | O | O | O | O | O | O |
| n | 11 | 11 | 11 | 11 | 11 | 11 | 11 | 11 | 11 | 12 | 12 | 12 | 12 | 12 | 12 | 12 | 12 | 12 | 12 | 13 | 13 | 13 | 13 | 13 |
| m | 3 | 4 | 5 | 6 | 7 | 8 | 9 | 10 | 11 | 6 | 3 | 4 | 5 | 6 | 7 | 8 | 9 | 10 | 11 | 3 | 4 | 5 | 6 | 7 |
| X | O | O | O | O | O | O | O | O | O | O | O | O | O | O | O | O | O | O | O | O | O | O | O | O |
| n | 13 | 13 | 13 | 13 | | | | | | | | | | | | | | | | | | | | |
| m | 8 | 9 | 10 | 11 | | | | | | | | | | | | | | | | | | | | |
| X | O | O | O | O | | | | | | | | | | | | | | | | | | | | |
or possibly
| n | 2 | 2 | 2 | 2 | 2 | 2 | 2 | 2 | 3 | 3 | 3 | 3 | 3 | 3 | 3 | 3 | 4 | 4 | 4 | 4 | 4 | 4 | 4 | 4 |
|---|---|---|---|---|---|---|---|---|---|---|---|---|---|---|---|---|---|---|---|---|---|---|---|---|
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| X | — | — | — | — | — | — | — | — | — | — | — | — | — | — | — | — | — | — | — | — | — | — | — | — |
| n | 4 | 3 | 3 | 3 | 3 | 3 | 3 | 3 | 3 | 4 | 4 | 4 | 4 | 4 | 4 | 4 | 4 | 5 | 5 | 5 | 5 | 5 | 5 | 5 |
| m | 11 | 3 | 4 | 5 | 6 | 7 | 8 | 9 | 10 | 11 | 3 | 4 | 5 | 6 | 7 | 8 | 9 | 10 | 11 | 3 | 4 | 6 | 7 | 8 |
| X | — | — | — | — | — | — | — | — | — | — | — | — | — | — | — | — | — | — | — | — | — | — | — | — |
| n | 5 | 5 | 5 | 6 | 6 | 6 | 6 | 6 | 6 | 6 | 6 | 6 | 7 | 7 | 7 | 7 | 7 | 7 | 7 | 7 | 7 | 8 | 8 | 8 |
| m | 9 | 10 | 11 | 3 | 4 | 5 | 6 | 7 | 8 | 9 | 10 | 11 | 3 | 4 | 5 | 6 | 7 | 8 | 9 | 10 | 11 | 3 | 4 | 5 |
| X | — | — | — | — | — | — | — | — | — | — | — | — | — | — | — | — | — | — | — | — | — | — | — | — |
| n | 8 | 8 | 8 | 8 | 8 | 8 | 9 | 9 | 9 | 9 | 9 | 9 | 9 | 9 | 10 | 10 | 10 | 10 | 10 | 10 | 10 | 10 | 10 | 10 |
| m | 6 | 7 | 8 | 9 | 10 | 11 | 3 | 4 | 5 | 6 | 7 | 8 | 9 | 10 | 11 | 3 | 4 | 5 | 6 | 7 | 8 | 9 | 10 | 11 |
| X | — | — | — | — | — | — | — | — | — | — | — | — | — | — | — | — | — | — | — | — | — | — | — | — |
| n | 11 | 11 | 11 | 11 | 11 | 11 | 11 | 11 | 11 | 12 | 12 | 12 | 12 | 12 | 12 | 12 | 12 | 12 | 12 | 13 | 13 | 13 | 13 | 13 |
| m | 3 | 4 | 5 | 6 | 7 | 8 | 9 | 10 | 11 | 6 | 3 | 4 | 5 | 6 | 7 | 8 | 9 | 10 | 11 | 3 | 4 | 5 | 6 | 7 |
| X | — | — | — | — | — | — | — | — | — | — | — | — | — | — | — | — | — | — | — | — | — | — | — | — |
| n | 13 | 13 | 13 | 13 | | | | | | | | | | | | | | | | | | | | |
| m | 8 | 9 | 10 | 11 | | | | | | | | | | | | | | | | | | | | |
| X | — | — | — | — | | | | | | | | | | | | | | | | | | | | |

Compounds of the formula (XXVI), where:
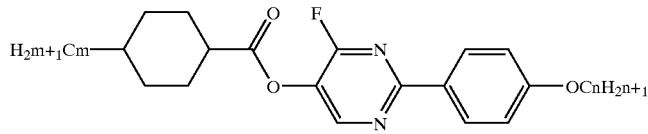
| n | 5 | 5 | 5 | 5 | 5 | 5 | 5 | 6 | 6 | 6 | 6 | 6 | 6 | 6 | 6 | 7 | 7 | 7 | 7 | 7 | 7 | 7 | 7 |
|---|---|---|---|---|---|---|---|---|---|---|---|---|---|---|---|---|---|---|---|---|---|---|---|
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 |
| n | 8 | 8 | 8 | 8 | 8 | 8 | 8 | 9 | 9 | 9 | 9 | 9 | 9 | 9 | 9 | 10 | 10 | 10 | 10 | 10 | 10 | 10 | 10 |
| m | 3 | 4 | 6 | 7 | 8 | 9 | 10 | 3 | 4 | 5 | 6 | 7 | 8 | 9 | 10 | 3 | 4 | 5 | 6 | 7 | 8 | 9 | 10 |
| n | 11 | 11 | 11 | 11 | 11 | 11 | 11 | 12 | 12 | 12 | 12 | 12 | 12 | 12 | 12 | 13 | 13 | 13 | 13 | 13 | 13 | 13 | |
| m | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
Note: last columns of first pair: n=7, m=10; n=7, m=11.
Compounds of the formula (XXVII), where:
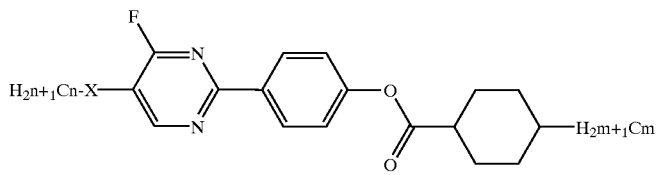
| n | 8 | 8 | 8 | 8 | 8 | 8 | 8 | 9 | 9 | 9 | 9 | 9 | 9 | 9 | 9 | 9 | 10 | 10 | 10 | 10 | 10 | 10 | 10 | 10 |
|---|---|---|---|---|---|---|---|---|---|---|---|---|---|---|---|---|---|---|---|---|---|---|---|---|
| m | 3 | 4 | 6 | 7 | 8 | 9 | 10 | 3 | 4 | 5 | 6 | 7 | 8 | 9 | 10 | 11 | 3 | 4 | 5 | 6 | 7 | 8 | 9 | 10 |
| X | — | — | — | — | — | — | — | — | — | — | — | — | — | — | — | — | — | — | — | — | — | — | — | — |
| n | 11 | 11 | 11 | 11 | 11 | 11 | 11 | 11 | 11 | 12 | 12 | 12 | 12 | 12 | 12 | 12 | 12 | 12 | 13 | 13 | 13 | 13 | 13 | 13 |
| m | 3 | 4 | 5 | 6 | 7 | 7 | 8 | 9 | 10 | 3 | 4 | 5 | 6 | 7 | 8 | 9 | 10 | 11 | 3 | 4 | 5 | 6 | 7 | 8 |
| X | — | — | — | — | — | — | — | — | — | — | — | — | — | — | — | — | — | — | — | — | — | — | — | — |
| n | 13 | 13 | 13 | 14 | 14 | 14 | 14 | 14 | 14 | 14 | 14 | 7 | 7 | 7 | 7 | 7 | 7 | 7 | 7 | 7 | 8 | 8 | 8 | 8 |
| m | 9 | 10 | 11 | 3 | 4 | 5 | 6 | 7 | 8 | 9 | 10 | 3 | 4 | 5 | 6 | 7 | 8 | 9 | 10 | 11 | 3 | 4 | 6 | 7 |
| X | — | — | — | — | — | — | — | — | — | — | — | O | O | O | O | O | O | O | O | O | O | O | O | O |
| n | 8 | 8 | 8 | 8 | 9 | 9 | 9 | 9 | 9 | 9 | 9 | 9 | 9 | 10 | 10 | 10 | 10 | 10 | 10 | 10 | 11 | 11 | 11 | |
| m | 8 | 9 | 10 | 11 | 3 | 4 | 5 | 6 | 7 | 8 | 9 | 10 | 11 | 3 | 4 | 5 | 6 | 7 | 8 | 9 | 10 | 3 | 4 | 5 |
| X | O | O | O | O | O | O | O | O | O | O | O | O | O | O | O | O | O | O | O | O | O | O | O | O |
| n | 11 | 11 | 11 | 11 | 11 | 11 | 11 | 12 | 12 | 12 | 12 | 12 | 12 | 12 | 12 | 13 | 13 | 13 | 13 | 13 | 13 | 13 | 13 | |
| m | 6 | 7 | 8 | 9 | 10 | 11 | 12 | 3 | 4 | 5 | 6 | 7 | 8 | 9 | 10 | 3 | 4 | 5 | 6 | 7 | 8 | 9 | 10 | 11 |
| X | O | O | O | O | O | O | O | O | O | O | O | O | O | O | O | O | O | O | O | O | O | O | O | O |
Compounds of the formula (XXIX), where
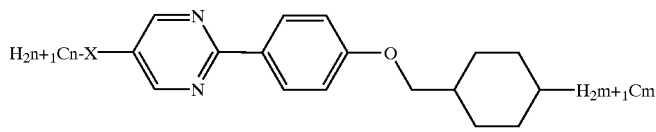
| n | 6 | 6 | 6 | 7 | 7 | 7 | 7 | 7 |
|---|---|---|---|---|---|---|---|---|
| m | 7 | 8 | 9 | 4 | 6 | 8 | 9 | 10 |
| X | — | — | — | — | — | — | — | — |
| n | 8 | 8 | 9 | 9 | 9 | 9 | 9 | 9 | 9 | 10 | 10 | 10 |
|---|---|---|---|---|---|---|---|---|---|---|---|---|
| m | 8 | 10 | 3 | 4 | 6 | 7 | 8 | 9 | 10 | 8 | 9 | 19 |
| X | — | — | — | — | — | — | — | — | — | — | — | — |
| n | 6 | 6 | 6 | 6 | 6 | 6 | 6 | 7 | 7 | 7 | 7 | 7 | 7 | 7 | 7 |
|---|---|---|---|---|---|---|---|---|---|---|---|---|---|---|---|
| m | 3 | 4 | 6 | 7 | 8 | 9 | 10 | 3 | 4 | 5 | 6 | 7 | 8 | 9 | 10 |
| X | O | O | O | O | O | O | O | O | O | O | O | O | O | O | O |
| n | 8 | 8 | 8 | 8 | 8 | 8 | 8 | 8 | 9 | 9 | 9 | 9 | 9 | 9 | 10 | 10 | 10 | 10 | 10 | 10 |
|---|---|---|---|---|---|---|---|---|---|---|---|---|---|---|---|---|---|---|---|---|
| m | 3 | 4 | 5 | 6 | 7 | 8 | 9 | 10 | 5 | 6 | 7 | 8 | 9 | 10 | 4 | 5 | 6 | 7 | 8 | 9 | 10 |
| X | O | O | O | O | O | O | O | O | O | O | O | O | O | O | O | O | O | O | O | O |

Compounds of the formula (XXX), where:

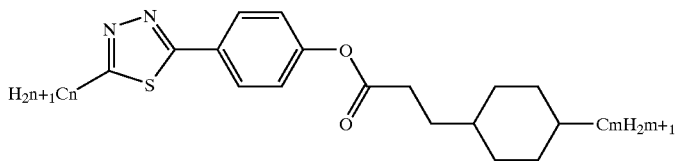

| n | 5 | 5 | 5 | 5 | 5 | 5 | 5 | 5 | 6 | 6 | 6 | 6 | 6 | 6 | 6 | 6 | 7 | 7 | 7 | 7 | 7 | 7 | 7 | 7 |
|---|---|---|---|---|---|---|---|---|---|---|---|---|---|---|---|---|---|---|---|---|---|---|---|---|
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |
| n | 8 | 8 | 8 | 8 | 8 | 8 | 8 | 9 | 9 | 9 | 9 | 9 | 9 | 9 | 10 | 10 | 10 | 10 | 10 | 10 | 10 | 10 | | |
| m | 3 | 5 | 6 | 7 | 8 | 9 | 10 | 4 | 5 | 6 | 7 | 8 | 9 | 10 | 3 | 4 | 5 | 6 | 7 | 8 | 9 | 10 | | |
| n | 11 | 11 | 11 | 11 | 11 | 11 | 11 | 11 | 12 | 12 | 12 | 12 | 12 | 12 | 12 | 12 | 13 | 13 | 13 | 13 | 13 | 13 | 13 | 13 |
| m | 3 | 4 | 5 | 6 | 7 | 8 | 9 | 10 | 3 | 4 | 5 | 6 | 7 | 8 | 9 | 10 | 3 | 4 | 5 | 6 | 7 | 8 | 9 | 10 |

The invention furthermore provides compounds of the general formula (II), selected from compounds of the formula (XXXI), where:

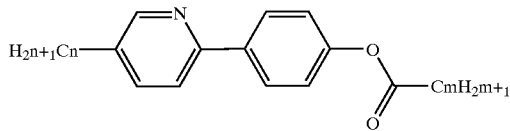

| n | 10 | 10 | 10 | 10 | 10 | 10 | 10 | 10 | 10 | 10 | 11 | 11 | 11 | 11 | 11 | 11 | 11 | 11 | 11 | 11 | 12 | 12 | 12 | 12 |
| m | 3 | 4 | 5 | 6 | 7 | 8 | 9 | 10 | 11 | 12 | 3 | 4 | 5 | 6 | 7 | 8 | 9 | 10 | 11 | 12 | 3 | 4 | 5 | 6 |
| X | — | — | — | — | — | — | — | — | — | — | — | — | — | — | — | — | — | — | — | — | — | — | — | — |
| n | 12 | 12 | 12 | 12 | 12 | 12 | 13 | 14 | 14 | 14 | 14 | 14 | 14 | 14 | 14 | 14 | 6 | 6 | 6 | 6 | 6 | 6 | 6 | 6 |
| m | 7 | 8 | 9 | 10 | 11 | 12 | 3 | 4 | 5 | 6 | 7 | 8 | 9 | 10 | 11 | 12 | 3 | 4 | 5 | 6 | 7 | 8 | 9 | 10 |
| X | — | — | — | — | — | — | — | — | — | — | — | — | — | — | — | — | O | O | O | O | O | O | O | O |
| n | 6 | 6 | 7 | 7 | 7 | 7 | 7 | 7 | 7 | 7 | 7 | 7 | 8 | 8 | 8 | 8 | 8 | 8 | 8 | 8 | 9 | 9 | 9 | 9 |
| m | 11 | 12 | 35 | 4 | 5 | 6 | 7 | 8 | 9 | 10 | 11 | 12 | 3 | 4 | 5 | 6 | 8 | 9 | 10 | 11 | 12 | 3 | 4 | 5 |
| X | O | O | O | O | O | O | O | O | O | O | O | O | O | O | O | O | O | O | O | O | O | O | O | O |
| n | 9 | 9 | 9 | 9 | 9 | 9 | 9 | 10 | 10 | 10 | 10 | 10 | 10 | 10 | 10 | 10 | 10 | 11 | 11 | 11 | 11 | 11 | 11 | 11 |
| m | 6 | 7 | 8 | 9 | 10 | 11 | 12 | 3 | 4 | 5 | 6 | 7 | 8 | 9 | 10 | 11 | 12 | 3 | 4 | 5 | 6 | 7 | 8 | 9 |
| X | O | O | O | O | O | O | O | O | O | O | O | O | O | O | O | O | O | O | O | O | O | O | O | O |
| n | 11 | 11 | 11 | 12 | 12 | 12 | 12 | 12 | 12 | 12 | 12 | 12 | 12 | 13 | 13 | 13 | 13 | 13 | 13 | 13 | 13 | 13 | 13 | 14 |
| m | 10 | 11 | 12 | 3 | 4 | 5 | 6 | 7 | 8 | 9 | 10 | 11 | 12 | 3 | 4 | 5 | 6 | 7 | 8 | 9 | 10 | 11 | 12 | 3 |
| X | O | O | O | O | O | O | O | O | O | O | O | O | O | O | O | O | O | O | O | O | O | O | O | O |
| n | 14 | 14 | 14 | 14 | 14 | 14 | 14 | 14 | | | | | | | | | | | | | | | | |
| m | 4 | 5 | 6 | 7 | 8 | 9 | 10 | 11 | 12 | | | | | | | | | | | | | | | |
| X | O | O | O | O | O | O | O | O | O | | | | | | | | | | | | | | | |

Compounds of the formula (XXVIII), where:

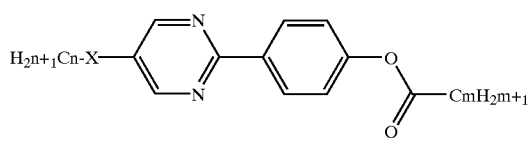

| n | 11 | 12 | 13 | 14 | 13 | 14 | 12 | 13 | 14 | 13 | 14 | 10 | 11 | 12 | 13 | 14 | 13 | 14 | 9 | 10 | 11 | 12 | 13 | 10 |
| m | 5 | 5 | 5 | 5 | 6 | 6 | 7 | 7 | 7 | 8 | 8 | 9 | 9 | 9 | 9 | 9 | 10 | 10 | 11 | 11 | 11 | 11 | 11 | 12 |
| X | — | — | — | — | — | — | — | — | — | — | — | — | — | — | — | — | — | — | — | — | — | — | — | — |
| n | 11 | 12 | 13 | 14 | 6 | 6 | 6 | 6 | 6 | 6 | 6 | 6 | 6 | 7 | 7 | 7 | 7 | 7 | 7 | 7 | 7 | 7 | 8 | 8 |
| m | 12 | 12 | 12 | 12 | 4 | 5 | 6 | 7 | 8 | 9 | 10 | 11 | 12 | 4 | 5 | 6 | 7 | 8 | 9 | 10 | 11 | 12 | 4 | 6 |
| X | — | — | — | — | O | O | O | O | O | O | O | O | O | O | O | O | O | O | O | O | O | O | O | O |
| n | 8 | 8 | 8 | 8 | 9 | 9 | 9 | 9 | 9 | 9 | 9 | 9 | 10 | 10 | 10 | 10 | 10 | 10 | 10 | 10 | 11 | 11 | 11 | 11 |
| m | 8 | 10 | 11 | 12 | 4 | 5 | 6 | 8 | 9 | 10 | 11 | 12 | 4 | 5 | 7 | 8 | 9 | 10 | 11 | 12 | 4 | 5 | 6 | 7 |
| X | O | O | O | O | O | O | O | O | O | O | O | O | O | O | O | O | O | O | O | O | O | O | O | O |

-continued

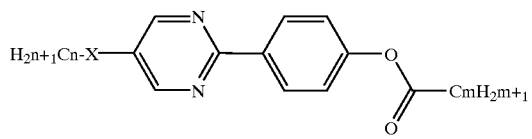

| n | 11 | 11 | 11 | 11 | 11 | 12 | 12 | 12 | 12 | 12 | 12 | 12 | 12 |
|---|----|----|----|----|----|----|----|----|----|----|----|----|----|
| m | 8  | 9  | 10 | 11 | 12 | 5  | 6  | 7  | 8  | 9  | 10 | 11 | 12 |
| X | O  | O  | O  | O  | O  | O  | O  | O  | O  | O  | O  | O  | O  |

Compounds of the general formula (XXXII), where:

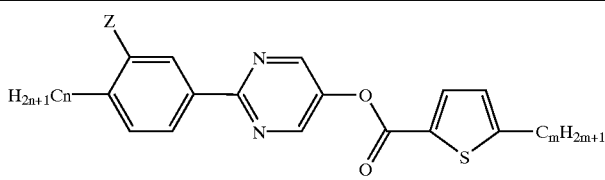

| n | 5 | 5 | 5 | 5 | 5 | 5 | 5 | 5 | 6 | 6 | 6 | 6 | 6 | 6 | 6 | 6 | 7 | 7 | 7 | 7 |    |    |    |    |    |
|---|---|---|---|---|---|---|---|---|---|---|---|---|---|---|---|---|---|---|---|---|----|----|----|----|----|
| m | 2 | 3 | 4 | 5 | 6 | 7 | 8 | 9 | 2 | 3 | 4 | 5 | 6 | 7 | 8 | 9 | 2 | 3 | 4 | 5 |    |    |    |    |    |
| n | 7 | 7 | 7 | 7 | 8 | 8 | 8 | 8 | 8 | 8 | 8 | 8 | 9 | 9 | 9 | 9 | 9 | 9 | 9 | 9 | 10 | 10 | 10 | 10 | 10 |
| m | 6 | 7 | 8 | 9 | 2 | 3 | 4 | 5 | 6 | 7 | 8 | 9 | 2 | 3 | 4 | 5 | 6 | 7 | 8 | 9 | 2  | 3  | 4  | 5  | 6  |
| n | 10| 10| 10| 11| 11| 11| 11| 11| 11| 11| 11| 12| 12| 12| 12| 12| 12| 12| 12| 13| 13 | 13 |    |    |    |
| m | 7 | 8 | 9 | 2 | 3 | 4 | 5 | 6 | 7 | 8 | 9 | 2 | 3 | 4 | 5 | 6 | 7 | 8 | 9 | 2 | 3  | 4  |    |    |    |
| n | 13| 13| 13| 13| 14| 14| 14| 14| 14| 14| 14| 14|   |   |   |   |   |   |   |   |    |    |    |    |    |
| m | 5 | 6 | 7 | 8 | 9 | 2 | 3 | 4 | 5 | 6 | 7 | 8 | 9 |   |   |   |   |   |   |   |    |    |    |    |    | and where Z is H or F in all cases.

Thiophenecarboxylic esters in which the heterocycle may not be fluorinated are generally described in EP-A-0 364 923. EP-A-0 459 406 describes thiophenecarboxylic esters in which the phenyl group has to be substituted by fluorine. In EP-A-0 392 510, the phenylene group has to be 2,3-cyano-substituted.

Tetrahydroquinazolines are generally described in U.S. Pat. No. 4,402,849. An example of compounds of this type can be found in JP-A-08059629, and in JP-A-08062559 and JP-A-07207267.

The examples which follow illustrate the invention. Mixtures according to the invention are given in Examples 1–15.

EXAMPLE 1

An LCD test cell is prepared from two commercially available glass plates which are transparently and conductively coated with indium-tin oxide. The plates are spin-coated (2 500 rpm, 10 s) with the alignment layer LQT-120 (from Hitachi Chemicals KK) which was diluted to 8.3% of its original solids content using N-methylpyrrolidone, cured by heating (230° C., 1 hour) and then aligned by subjecting them to a rubbing process (rubbing material: rayon type YA-20-R*, clearance 0.2 mm, once, roller speed 700 rpm, substrate speed 10 cm/s, roller diameter 10 cm).

The rubbed glass plates are arranged such that the rubbing direction is parallel, adhesively bonded to produce test cells and set 1.3 μm apart by means of a spacer.

A mixture consisting of

| Compound | Content | Structure |
|----------|---------|-----------|
| 1 | 24.1% | $C_9H_{19}$–pyrimidine–phenyl–$OC_6H_{13}$ |
| 2 | 24.1% | $C_8H_{17}$–pyrimidine–phenyl–$OC_6H_{13}$ |

-continued

| Compound | Content | Structure |
|---|---|---|
| 3 | 19.2% | 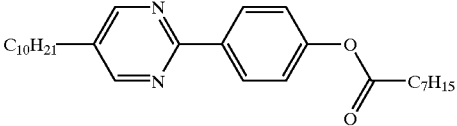 |
| 4 | 28.9% | 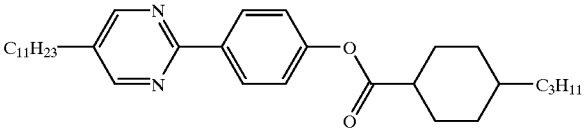 |
| 5 | 3.8% | 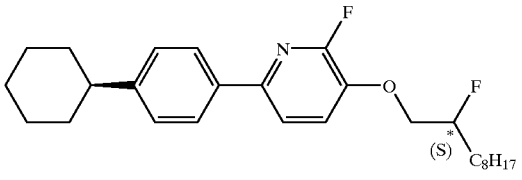 | having the phase transitions I/N* 81.6–85.9 and N*/Sc* 59.3° C. is introduced into the cell and initially aligned in the nematic or cholesteric phase by cooling. On further cooling, a 3 volt direct voltage is applied and the cell is transferred into the Sc* phase (chiral smectic C) range at a cooling rate of 2 K/min. During this process, a monostable monodomain is formed which is characterized by a certain temperature dependence of the tilt angle which is assessed by experiments in a polarizing microscope.

The results are expressed by the value DT (T1,1), which means that, starting from a lower temperature T1, the tilt angle changes by less than 1° in the whole range from T1 to (T1+DT). For example, DT (15,1)=22 means that the tilt angle changes by a maximum of 1° in the range from 15° C. to 37° C.

The DT values should generally be as high as possible to provide a broad operating temperature range without significant deviation of the director. DT values are always reported in degrees Celsius.

In the following inventive and comparative examples, the above-described alignment is carried out by applying the 3 volt direct voltage in the temperature range of ±2° C. at the N/Sc* phase transition point.

The mixture of Example 1 has the following values: DT (15,1)/DT (20,1)/DT (25,1)/DT (30,1): 25/21/18/16 and thus a broad operating temperature range, as likewise illustrated by the examples below.

EXAMPLE 2

A mixture consisting of 19.28% of compound 1, 19.28% of compound 2, 15.36% of compound 3, 23.12% of compound 4 and 3.04% of compound 5 from Example 1 and 20% of the compound

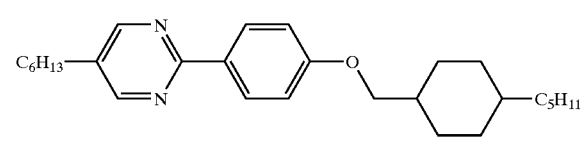

has the phase transition values I/N* 97.7–92.8 and N*/Sc* 58.9° C. and the values DT (15,1)/DT (20,1)/DT (25,1)/DT (30,1): 30/27/25/21.

EXAMPLE 3

A mixture of the composition given below has the phase transition values I/N* 78.9–74.4 and N*/Sc* 57.3° C. and the values DT (10,1)/DT (15,1)/DT (30,1): 22.5/20/17.5.

| Compound | Content | Structure |
|---|---|---|
| 1 | 19.2% | 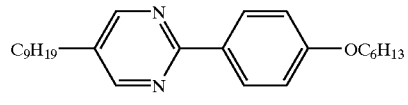 |
| 2 | 19.2% | 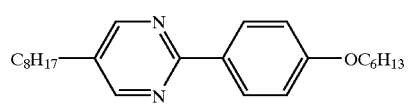 |

| Compound | Content | Structure |
|---|---|---|
| 3 | 15.4% | 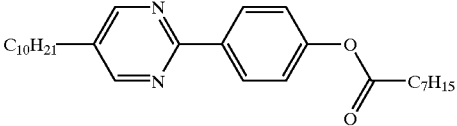 |
| 4 | 23.1% | 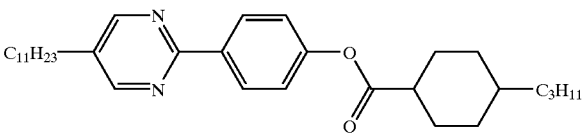 |
| 5 | 10.0% | 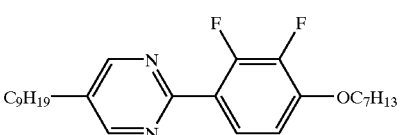 |
| 6 | 10.0% | 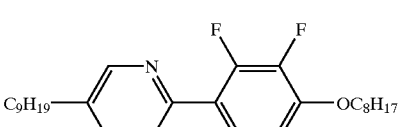 |
| 7 | 3.0% | 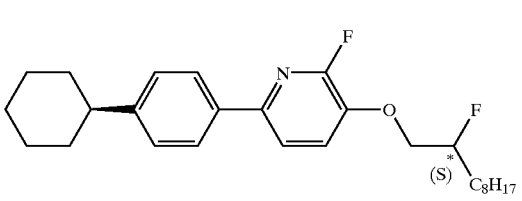 |
EXAMPLE 4
A mixture consisting of 16.23% of compound 1, 16.32% of compound 2, 18.1% of compound 3, 19.6% of compound 4, 8.5% of compound 5, 8.5% of compound 6, 2.55% of compound 7 from Example 3 and 15% of the compound
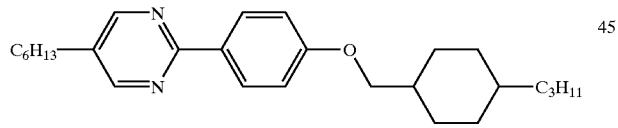
as the phase transition values I/N* 92.2–87.8 and N*/Sc* 57.7° C. and the values: DT (10,1)/DT (15,1)/DT (30,1): 27.5/23.8/18.
EXAMPLE 5
A mixture consisting of
| % by weight | Structure |
|---|---|
| 10.0% | 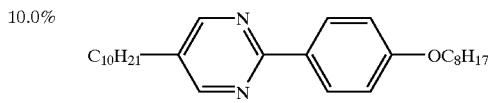 |
| 10.0% | 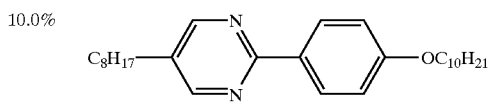 |

-continued

| % by weight | Structure |
|---|---|
| 8.0% | 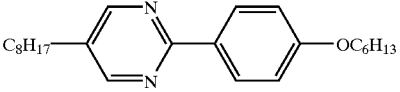 C₈H₁₇—pyrimidine—phenyl—OC₆H₁₃ |
| 8.0% | 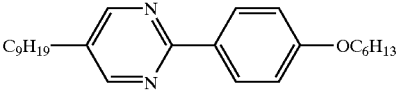 C₉H₁₉—pyrimidine—phenyl—OC₆H₁₃ |
| 10.0% | C₉H₁₉—pyrimidine—phenyl—OC₈H₁₇ |
| 10.0% | C₁₀H₂₁—pyrimidine—phenyl—O—C(=O)—C₇H₁₃ |
| 21.0% | C₁₁H₂₃—pyrimidine—phenyl—O—C(=O)—cyclohexyl—C₅H₁₁ |
| 10.0% | C₈H₁₇O—C(=O)—O—pyrimidine—phenyl—C₈H₁₇ |
| 10.0% | C₆H₁₃—pyrimidine—phenyl—O—CH₂—cyclohexyl—C₅H₁₁ |
| 3.0% | cyclohexyl—phenyl—(F)pyridine—O—CHF—(S)—C₈H₁₇ | has the phase transition values I/N* 90.0–87.2 and N*/Sc* 65.1° C. and the values DT (15,1)/DT (20,1)/DT (25,1)/DT (30,1): 30/27/25/25.

EXAMPLE 6

A mixture consisting of 85% of the mixture of Example 5 and 15% of the compound

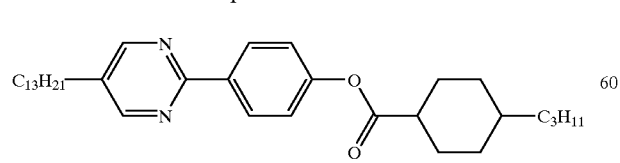

has the phase transitions I/N* 94.9–92.2 and N*/Sc* 65.7° C. and the values DT (15,1)/DT (20,1)/DT (25,1)/DT (30,1) 33.8/30/27.5/26.3.

EXAMPLE 7

A mixture consisting of 85% of the mixture of Example 5 and 15% of the compound

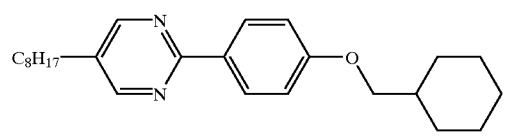

has the phase transitions I/N* 89.7–87.5 and N*/Sc* 66.3° C. and the values DT (15,1)/DT (20,1) DT (25,1)/DT (30,1) 27.5/25/22.5/20.

EXAMPLE 8

A mixture consisting of 85% of the mixture of Example 5 and 15% of the compound

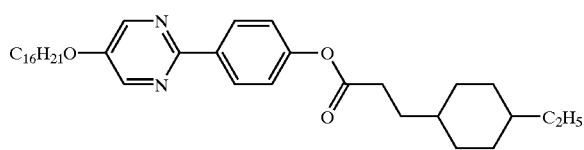

has the phase transitions I/N* 93.9–91.1 and N*/Sc* 67.6° C. and the values DT (15,1)/DT (20,1) DT (25,1)/DT (30,1) 27.5/25/25.

EXAMPLE 9

A mixture consisting of 85% of the mixture of Example 5 and 15% of the compound

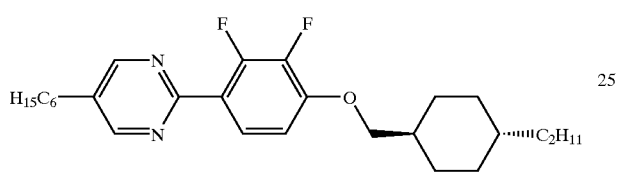

has the phase transitions I/N* 92.1–89.6 and N*/Sc* 63.1° C. and the values DT (15,1)/DT (20,1) DT (25,1)/DT (30,1) 26.3/23.8/22.5/20

EXAMPLE 11

A mixture consisting of 85% of the mixture of Example 5 and 15% of the compound

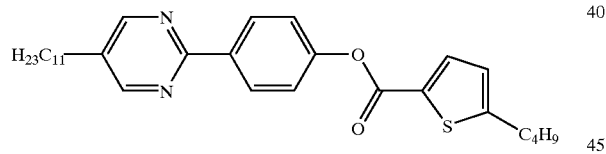

has the phase transitions I/N* 89.1–86.7 and N*/Sc* 61.4° C. and the values DT (15,1)/DT (20,1)/DT (25.1)/DT (30.1) 27.5/26.3/22.5/21.3.

EXAMPLE 12

A mixture consisting of 85% of the mixture of Example 5 and 15% of the compound

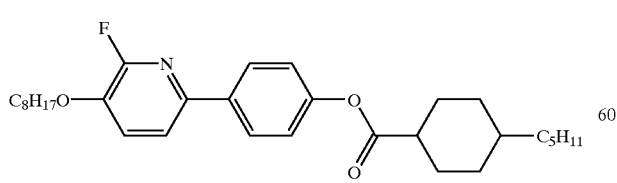

has the phase transitions I/N* 98.0–94.2 and N*/Sc* 71.7° C. and the values DT (15,1)/DT (20,1)/DT (25,1)/DT (30,1) 32.5/31.3/32.5/30.

EXAMPLE 13

A mixture consisting of 85% of the mixture of Example 5 and 15% of the compound

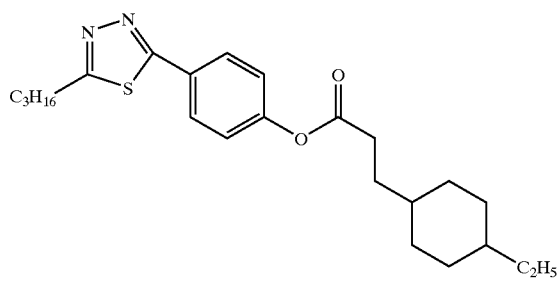

has the phase transitions I/N* 89.5–87.2 and N*/Sc* 69.7° C. and the values DT (15,1)/DT (20,1)/DT (25,1)/DT (30,1) 42.5/40./35.5/32.

EXAMPLE 14

A mixture consisting of 85% of the mixture of Example 5 and 15% of the compound

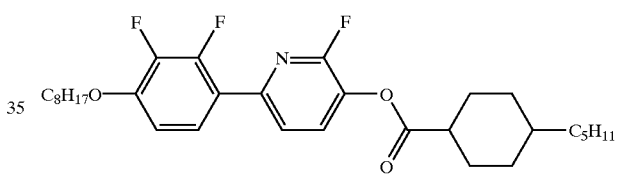

has the phase transitions I/N* 95.1–92.1 and N*/Sc* 64.6° C. and the values DT (15,1)/DT (20,1)/DT (25,1)/DT (30,1) 35/40/35.5/31.5.

EXAMPLE 15

A mixture consisting of 85% of the mixture of Example 5 and 15% of the compound

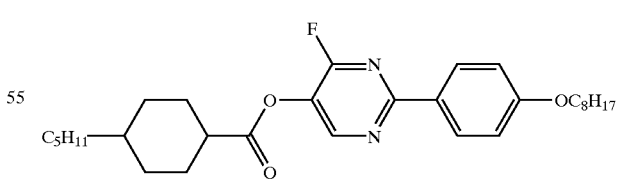

has the phase transitions I/N* 99.6–96.0 and N*/Sc* 63.2° C. and the values DT (15,1)/DT (20,1)/DT (25,1)/DT (30,1) 32.5/30/28.8/26.

The compounds according to the invention are further illustrated by Examples 16–25.

EXAMPLE 16

4-(2-Fluoro-3-hexyloxypryridine6-yl)phenyl 5-Octylthiophene-2-carboxylate

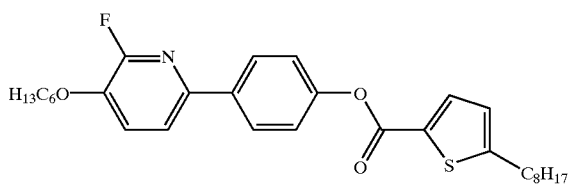

0.8 g of 4-(2-fluoro-3-hexyloxypyridin-6-yl)phenol and 0.7 g 5-octylthiophene-2-carboxylic acid are reacted in 100 ml of dichloromethane in the presence of 0.6 g of dicyclohexylcarbodiimide. Workup by filtration, column chromatography and recrystallization gives 1 g of colorless crystals having a melting point of 101° C. and a clearing point of 124° C.

The following compounds are obtained in a similar manner:

EXAMPLE 17

4-(2-Fluoro-3-hexyloxypyridin-6-yl)phenyl 5-Hexylthiophene-2-carboxylate Having a Melting Point of 95° C. and a Clearing Point of 126° C.

EXAMPLE 18

6-(4-Octyloxyphenyl)-2-fluoropyridin-3-yl 5-Butylthiophene-2-carboxylate

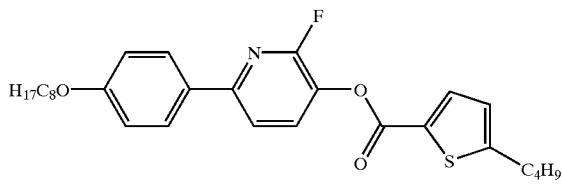

having a melting point of 86° C. and a clearing point of 114° C.

EXAMPLE 19

4-(5-Decyl-4-fluoropyrimidin-2-yl)phenyl 5-Butylthiophene-2-carboxylate

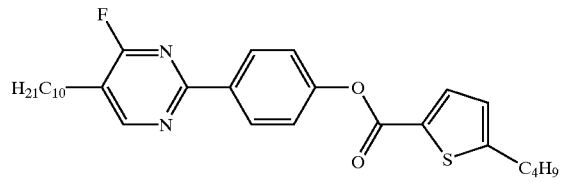

EXAMPLE 20

4-(6-Ethyl-1,2,3,4-tetrahydroquinazolin-2-yl)phenyl trans-4-Pentylcyclohexanecarboxylate

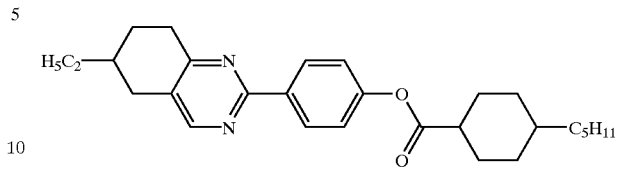

Phase Sequence X 114 N 216 I

EXAMPLE 21

4-(6-Nonyl-1,2,3,4-tetrahydroquinazolin-2-yl)phenyl trans-4-Pentylcyclohexanecarboxylate
Phase Sequence X 112 $S_C$ 124 $S_A$ 143 N 204 I

EXAMPLE 22

4-(6-Nonyl-1,2,3,4-tetrahydroquinazolin-2-yl)phenyl trans-4-Propylcyclohexanecarboxylate
Phase Sequence X 111 ($S_C$ 100) $S_A$ 124 N 202 I

EXAMPLE 23

4-(6-Propyloxy-1,2,3,4-tetrahydroquinazolin-2-yl) phenyl trans-4-Pentylcyclohexanecarboxylate
Phase Sequence X 99 N 175 I

EXAMPLE 24

4-(6-Hexyloxy-1,2,3,4-tetrahydroquinazolin-2-yl) phenyl trans-4-Pentylcyclohexanecarboxylate
Phase Sequence X 100 N 155

EXAMPLE 25

4-(6-Octyloxy-1,2,3,4-tetrahydroquinazolin-2-yl) phenyl trans-4-Pentylcyclohexanecarboxylate
Phase Sequence X 97 ($S_C$95) N 145 I

EXAMPLE 26

4-(5-Tetradecylpyrimidin-2-yl)phenyl trans-4-Pentylcyclohexane-carboxylate
Phase Sequence X 55 $S_2$ 96 $S_C$ 130 N 151 I

EXAMPLE 27

4-(5-Tetradecylpyrimidin-2-yl)phenyl trans-4-Hexylcyclohexanecarboxylate
Phase Sequence X 77 $S_2$ 105 $S_C$ 133 N 147 I

EXAMPLE 28

4-(5-Tetradecylpyrimidin-2-yl)phenyl trans-4-Heptylcyclohexanecarboxylate
Phase Sequence X 41 $S_2$ 108 $S_C$ 136 N 148 I

EXAMPLE 29

2-(4-Undecylphenyl)pyrimidin-5-yl trans-4-Propylcyclohexanecarboxylate
Phase Sequence X 77 $S_A$ 165 N 171 I

EXAMPLE 30

2-(4-Undecylphenyl)pyrimidin-2-yl 5-Pentylthiophene-2-carboxylate
Phase Sequence X 86 $S_A$ 91 N 111 I

EXAMPLE 31

4-(2-Fluoro-4-undecylphenyl)phenyl 5-Pentylthiophene-2-carboxylate
Phase Sequence X 41 N 791 I

EXAMPLE 32

4-(5-Undecylpyridin-2-yl)-2-fluorophenyl 5-Pentylthiophene-2-carboxylate
Phase Sequence X 74 N 89 I

EXAMPLE 33

4-(5-Undecylpyridin-2-yl)phenyl 5-Pentylthiophene-2-carboxylate
Phase Sequence X 61 $S_2$ 65 $S_C$ 89 N 112 I

What is claimed is:

1. An active-matrix display containing a ferroelectric (chiral smetic) liquid-crystal mixture in a liquid crystal layer in the form of a monodomain having an unambiguously defined direction of the layer normal z of the SmC* phase, where the layer normal z and the preferential direction n of the nematic or cholestreric phase (M* phase) form an angle of more than 5", wherein the liquid-crystal mixture comprises at least one compound of the formula (I)

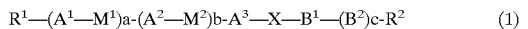

$$R^1-(A^1-M^1)a-(A^2-M^2)b-A^3-X-B^1-(B^2)c-R^2 \quad (1)$$

where the symbols are as defined below:

$R^1$, $R^2$ are, independently of one another, identical or different and are each
  a) hydrogen, fluorine or CN a straight-chain or branched alkenyl, alkenyloxy, alkyl or alkyloxy radical (with or without asymmetric carbon atoms) having 2 to 16 carbon atoms, where
    b1) one or two nonterminal —CH$_2$— groups may be replaced by —O—, —OC(=O)—, —(C=O), —C(=O)O—, —Si(CH$_3$)$_2$—, CH(Cl)— and/or one or two —CH$_2$— groups may be replaced by —CH=CH— or —C≡C—
    and one or more H atoms may be replaced by F and/or
    b2) one or more —CH$_2$— groups may be replaced by phenylene-1,4-diyl (unsubstituted, monosubstituted or disubstituted by F), phenylene-1,3-diyl (unsubstituted, monosubstituted or disubstituted by F), cyclohexane-1,4-diyl (unsubstituted or monosubstituted by F or CN) or cyclopropane-1,2-diyl
    and one or more H atoms may be replaced by F
with the provisos that only one of the radicals $R^1$, $R^2$ can be hydrogen, F or CN and that two adjacent —CH$_2$— groups cannot be replaced by —O—

$M^1$, $M^2$ are, independently of one another, identical or different and are each —C(=O))—, —OC(=O)—, CH$_2$O—, —OCH$_2$—, —CF$_2$O, —OCF$_2$—, —CH$_2$CH$_2$—, CF$_2$CF$_2$—, —CH=CH—, —CH=CF—, —CF=CF—, —C≡C—, —CH$_2$CH$_2$C(=O)O—, —OC(=O)CH$_2$CH$_2$—, —(CH$_2$)$_4$—, —OCH$_2$CH$_2$CH$_2$—, —CH$_2$CH$_2$CH$_2$O—, —OCH$_2$CF$_2$CH$_2$, —CH$_2$CF$_2$CH$_2$O— or a single bond $A^1$, $A^2$, $A^3$ are, independently of one another, identical or different and are each cyclohexane-1,4-diyl (unsubstituted or monosubstituted by F, CH$_3$, CN), cyclohex-1-ene-1,4-diyl, cyclohex-2-ene-1,4-diyl, 2-oxocyclohexane-1,4-diyl, 2-cyclohexen-1-one-3,6-diyl, 1-alkyl-1-silacyclohexane-1,4-diyl, bicyclo[2,2,2] octane-1,4-diyl, spiro[4,5]decane-2,8-diyl, spiro[5,5]undecane-3,9-diyl, phenylene-1,4-diyl (unsubstituted, monosubstituted or disubstituted by CN, CN$_3$, CF$_3$, OCH$_3$, unsubstituted, monosubstituted, disubstituted, trisubstituted or tetrasubstituted by F), phenylene-1,3-diyl (unsubstituted monosubstituted or disubstituted by CN, CH$_3$, CF$_3$, OCF$_3$, unsubstituted, monosubstituted, disubstituted, trisubstituted or tetrasubstituted by F), thiophene-2,5-diyl, thiophene-2,4-diyl, (1,3,4)-oxadiazole-2,5-diyl, (1,3,4)-thiadiazole-2,5-diyl, 1,3-thiazole-2,5-diyl, 1,3-thiazole-2,4-diyl, (1,3)-oxazole-2,5-diyl, isoxazole-2,5-diyl, indane-2,6-diyl, naphthalene-2,6-diyl (unsubstituted, monosubstituted or disubstituted by F or CN), 1,2,3,4-tetrahydronaphthalene-2,6-diyl, decaline-2,6-diyl, pyrimidine-2,5-diyl (unsubstituted or monosubstituted by F), pyridine-2,5-diyl (unsubstituted, monosubstituted or disubstituted by F), pyrazine-2,5-diyl (unsubstituted or monosubstituted by F), pyridazine-3,6-diyl, quinoline-2,6-diyl, quioline-3,7-diyl, isoquinoline-3,7-diyl, quinazoline-2,6-diyl, 5,6,7,8-tetrahydroquinazoline-2,6-diyl, quinoxaline-2,6-diyl, 1,3-dioxane-2,5-diyl (unsubstituted or monosubstituted by CN), benzothiazle-2,6-diyl, piperidine-2,4-diyl, piperazine-1,4-diyl $B^1$ is cyclohexane-1,4-diyl (unsubstituted, monosubstituted or disubstituted by F, CH$_3$, CN), perfluorocyclohexane-1,4-diyl, cyclohex-1-ene-1,4-diyl, cyclohex-2-ene-1,4-diyl, 1-alkyl-1-silacyclohexane-1,4-diyl, bicyclo[2,2,2]octane-1,4-diyl, cyclopentane-1,3-diyl, cycloheptane-1,4-diyl, tetrahydrofuran-2,5-diyl, tetrahydrofuran-2,4-diyl, phenylene-1,4-diyl (unsubstituted, monosubstituted or disubstituted by CN, CH$_3$, CF$_3$, OCF$_3$, unsubstituted, monosubstituted, disubstituted, trisubstituted or tetrasubstituted by F), phenylene-1,3-diyl (unsubstituted, monosubstituted or disubstituted by CN, CH$_3$, CF$_3$, OCF$_3$, unsubstituted, monosubstituted, disubstituted or trisubstituted by F), thiophene-2,5-diyl (unsubstituted or monosubstituted by F), thiophene-2,4-diyl (unsubstituted or monosubstituted by F), 1,3-thiazol-2,5-diyl (unsubstituted or monosubstituted by F), 1,3-thiazol-2,4-diyl (unsubstituted or monosubstituted by F) (1,3,4)-thiadiazol-2,5-diyl, 1,3-dioxane-2,5-diyl (unsubstituted or monosubstituted by CN), tetrahydropyran-2,5-diyl, 6,6-difluorotetrahydro pyran-2,5-diyl, 6,6-difluoro-2,3-dihydro-6H-pyran-2,5-diyl, 6-fluoro-3,4-dihydro-2H-pyran-2,5-diyl, piperidine-1,4-diyl, piperazine-1,4-diyl, pyrimidine-2,5-diyl (unsubstituted or monosubstituted by F), pyridine-2,5-diyl (unsubstituted or monosubstituted by F), 1,2,3,4-tetrahydronaphthalene-2,6-diyl, decaline-2,6-diyl $B^2$ is cyclohexane-1,4-diyl (unsubstituted, monosubstituted or disubstituted by F, CH$_3$, CN), cyclohex-1-ene-1,4-diyl (unsubstituted or monosubstituted by F), cyclohex-2-ene-1,4-diyl, 1-alkyl-1-silacyclohexane-1,4-diyl, bicyclo[2,2,2]octane-1,4-diyl, phenylene-1,4-diyl (unsubstituted, monosubstituted or disubstituted by CN, CH$_3$, CF$_3$, OCF$_3$, unsubstituted, monosubstituted, disubstituted, trisubstituted or tetrasubstituted by F), phenylene-1,3-diyl (unsubstituted, monosubstituted or disubstituted by CN, CH$_3$, CF$_3$, OCF$_3$, unsubstituted, monosubstituted, disubstituted or trisubstituted by F), thiophene-2,5-diyl, thiophene-2,4-diyl, 1,3-thiazole-2,5-diyl, 1,3-thiazole-2,4-diyl, (1,3,4)-thiadiazole-2,5-diyl, 1,3-dioxane-2,5-diyl (unsubstituted or monosubstituted by CN), tetrahydrofuran-2,5-diyl, tetrahydropyran-2,5-diyl, 6,6-difluorotetrahydropyran-2,5-diyl, 6,6-difluoro-2,3-dihydro-6H-pyran-2,5-diyl, 6-fluoro-3,4-dihyfro-2H-pyran-2,5-diyl, pyrimidine-2,5-diyl (unsubstituted or monosubstituted F), pyridine-2,5-diyl (unsubstituted or monosubstituted F), indane-2,6-diyl, piperidine-1,4-diyl, piperazine-1,4-diyl, pyrimidine-2,5-diyl (unsubstituted or monosubstituted by F)

X is —$(CH_2)_n$—, where
a) one or two —$CH_2$— groups may be replaced by —O— or —C(=O)— and/or
b) one —$CH_2CH_2$— group may be replaced by —CH=CH— and one or more H of the —$CH_2$— groups may be replaced by F
with the provisos that
1) n is 2, 3 or 4
2) two adjacent —$CH_2$— groups cannot be replaced by —O— a, b, c are each zero, 1 or 2, with the provisos that
1) a must be 1 when $R^1$ is hydrogen, F or CN
2) the sum of a+b+c is at least 1
3) the radicals A and M, respectively, in the brackets may be identical or different when the corresponding index is 2.

2. A display as claimed in claim 1, wherein the liquid-crystal mixture has a spontaneous polarization of <200 nC/cm2 and DT (15,1) is >20.

3. A display as claimed in claim 1, wherein, in (I),

X is —OC(=O)—, —$OCH_2$— or —OC(=O)$CH_2CH_2$—.

4. A display as claimed as claimed in claim 1, wherein, in (I)
$B^1$ is cyclohexane-1,4-diyl, cyclohex-1-ene-1,4-diyl, phenylene-1,4-diyl, unsubstituted, monosubstituted or disubstituted by F, or thiophene-2,5-diyl.

5. A display as claimed in claim 1, wherein, in (I),
$A^1$ is pyrimidine-2,5-diyl (unsubstituted or monosubstituted by F), pyridine-2,5-diyl (unsubstituted or monosubstituted by F), phenylene-1,4-diyl (unsubstituted, monosubstituted or disubstituted by F), or (1,3,4)-thiadiazol-2,5-diyl.

6. A display as claimed in claim 1, wherein the liquid-cyrstal mixture is composed of 3 to 30 compounds and comprises at least one compound of the formula (I) and at least one compound of the formula (II) below and, if desired, at least one compound of the formula (III) below

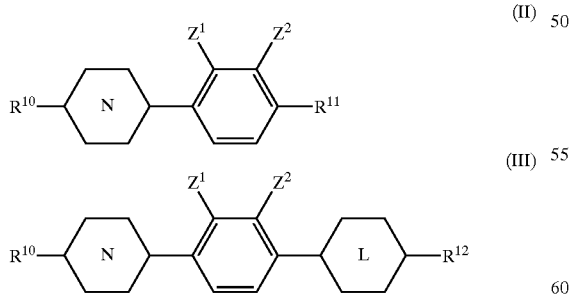

where:
$R^{10}$, $R^{11}$ are as defined for $R^1$, $R^2$, where additionally the terminal —$CH_3$— group may in each case be replaced by one of the chiral groups (optically active or racemic) below:

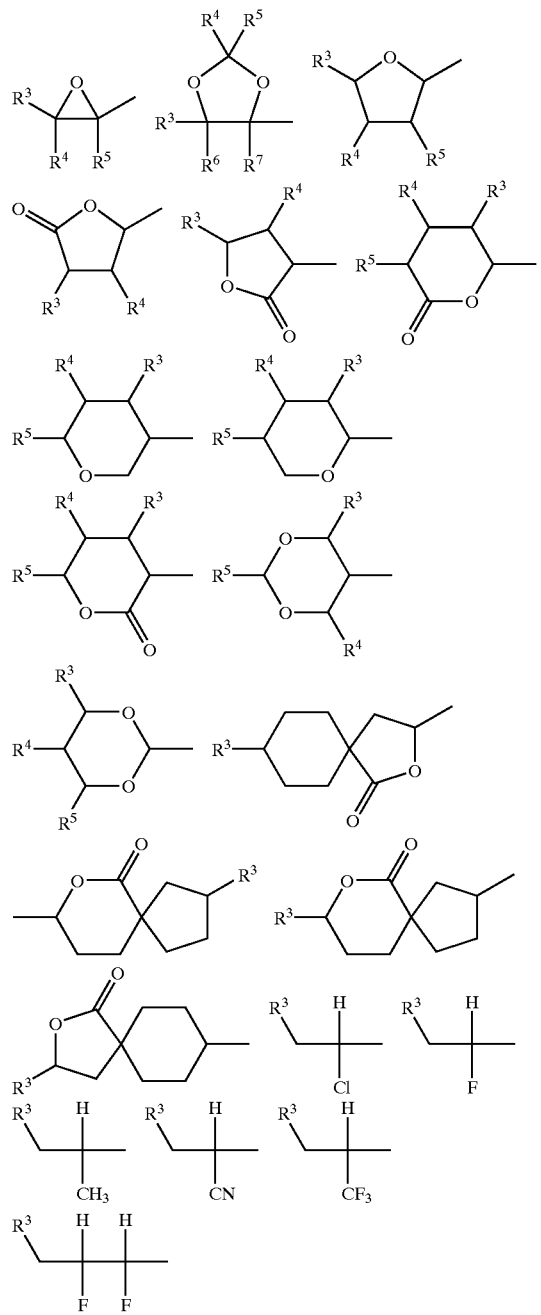

$R^3$, $R^4$, $R^5$, $R^6$, $R^7$ are identical or different are each
a) hydrogen
b) a straight-chain or branced alkyl radical (with or without asymmetric carbon atoms) having 1 to 16 carbon atoms, where
b1) one or more nonadjacent and nonterminal $CH_2$ groups may be replaced by —O— and/or
b2) one or two $CH_2$ groups may be replaced by —CH=CH—
c) $R^4$ and $R^5$ together may alternatively be —$(CH_2)_4$— or —$(CH_2)_5$— if they are attached to an oxirane, dioxolane, tetrahydrofuran tetrahydropyran, butyrolactone or valerolactone system:

$R^{12}$ is hydrogen or a straight-chain or branched alkyl radial (with or without asymmetric carbon atoms) having 1 to 6 carbon atoms, where one or more H may be replaced by F and one or two nonadjacent nonterminal —CH$_2$— groups may be replaced by —O—

Z$^1$, Z$^2$, Z$^3$, Z$^4$, Z$^5$, Z$^6$ are each, independently of one another, H or F

is a bivalent radical selected from the group consisting of pyridine-2,5-diyl unsubstituted or monosubstituted by F, pyrimidine-2,5-diyl, unsubstituted or monosubstituted by F, pyrazine-2,5-diyl, unsubstituted or monosubstituted by F,

is a bivalent radical selected from the group consisting of cyclohexane-1,4-diyl, unsubstituted or monosubstituted by CN, CH$_3$, or disubstituted by F, cyclohex-1-ene-1,4-diyl, perfluorocyclohexane-1,4-diyl, cyclohex-2-ene-1,4-diyl, 1-alkyl-1-silacyclohexane-1,4-diyl, bicyclo[2,2,2]octane-1,4-diyl.

7. A display as claimed in claim 6, wherein the liquid-crystal mixture is composed of 3 to 30 compounds and comprises at least one compound of the formula (I) and at least one compound of the formula (II) and at least one additional compound, selected from the group consisting of (III), (IV), (V), (VI), (VII), where the compounds of the formulae (II) and (III) are as defined in claim 6,

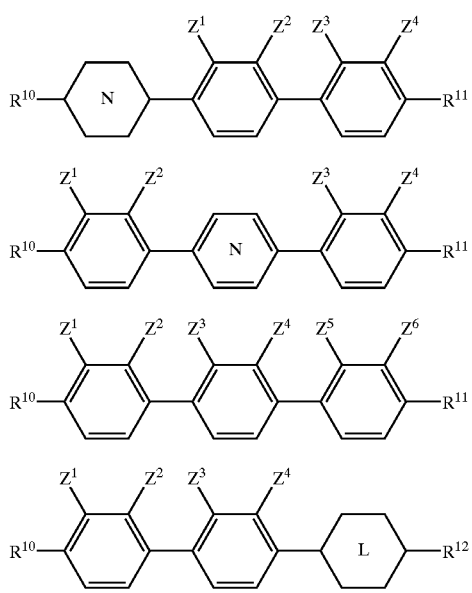

where the symbols and indices are as defined in claim 6.

8. A display as claimed in claim 1, wherein the liquid-crystal mixture is composed of 3 to 30 compounds and comprises at least one compound of the formula (I) and at least one compound of the formula (II) and at least one additional compound selected from the group consisting of (VIII), (IX), (X), (XI), (XII), (XIII), (XIV), (XV), (XVI), (XVII), where the compound of the formulae (II) and (III) are as defined in claim 6,

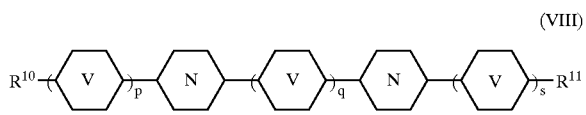

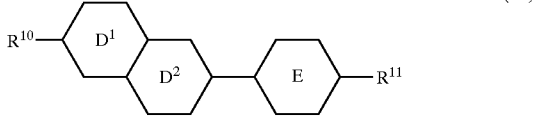

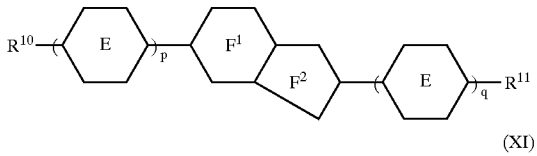

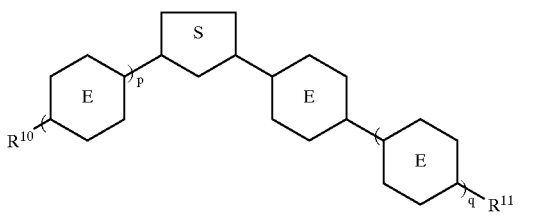

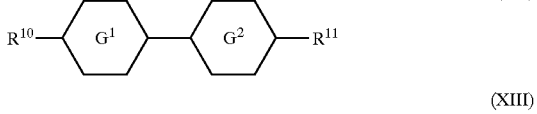

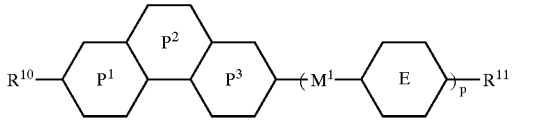

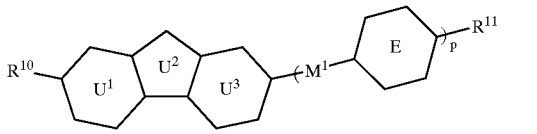

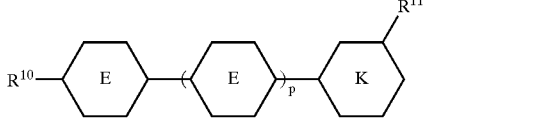

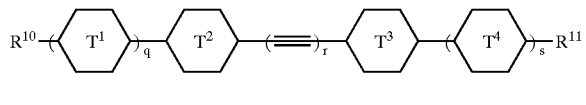

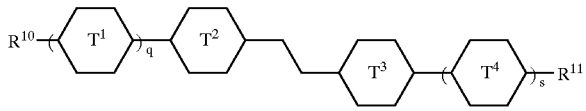

where the symbols and indices are as defined in claim 6 or as defined below:

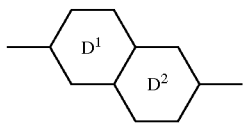

is a bivalent radical selected from the group consisting of naphthalene-2,6-diyl, in which one or two ring carbon atoms may be replaced by N and which can be monosubstituted or disubstituted by F or CN and in which $D^1$ or $D^2$ may also be a (saturated) alicycle

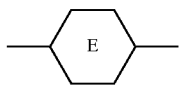

is a bivalent radical selected from the group consisting of phenylene-1,4-diyl, unsubstituted, monosubstituted or disubstituted by CN, or unsubstituted, monosubstituted, disubstituted, trisubstituted or tetra-substituted by F, pyridine-2,5-diyl, unsubstituted or monosubstituted by F, pyrimidine-2,5-diyl, unsubstituted or monosubstituted by F, cyclohexane-1,4-diyl

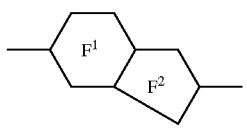

is a bivalent radical selected from the group consisting of indane-2,5-diyl, unsubstituted, monosubstituted or disubstituted by F in the aromatic ring, indan-1-one-2,6-diyl, unsubstituted, monosubstituted or disubstituted by F in the aromatic ring, benzothiazole-2,6-diyl, benzothiazole-2,5-diyl, benzo[b]thiophene-2,5-diyl, benzo[b]-thiophene-2,6-diyl

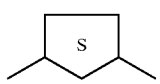

is a bivalent radical selected from the group consisting of (1,3,4)-thiadiazole-2,5-diyl, (1,3)-thiazole-2,5-diyl, thiophene-2,5-diyl, (1,3,4)-oxadiazole-2,5-diyl, (1,3)-oxazole-2,5-diyl, isoxazole-2,5-diyl

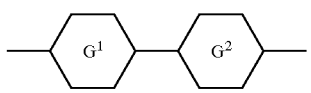

is a bivalent radical selected from the group consisting of 1,1'-biphenyl-4,4'-diyl, unsubstituted, monosubstituted or disubstituted by CN, or unsubstituted, monosubstituted, disubstituted, trisubstituted or tetra-substituted by F, 1,1'-phenylcyclohexyl-4,4'-diyl, 5,5'-pyridylpyrimidine-2,2'-diyl, unsubstituted or monosubstituted by F in one or both of the heterocycles, 5,2'-pyridylpyrimidine-2,5'-diyl, unsubstituted or monosubstituted by F in one or both of the heterocycles, 1,2'-phenyldioxane-4,5'-diyl, 1,2'-(2-dluorophenyl)dioxane-4,5'-diyl, 1,2'-(3-fluorophenyl)dioxane-4,5'-diyl, 1,2'-(2,3-difluorophenyl)dioxane-4,5'-diyl

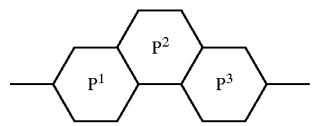

is a bivalent phenanthrene-2,7-diyl radical in which one or two ring carbon atoms may be replaced by N and which may be monosubstituted, disubstituted, trisubstituted or tetrasubstituted by F and in which $P^2$ and/or $P^3$ may be a (saturated) alicycle

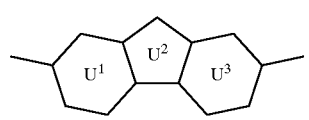

is a bivalent fluoroene-2,7-diyl radical in which the —$CH_2$— group is $U^2$ may be replaced by —C(=O)—, —CHF— or —$CF_2$—

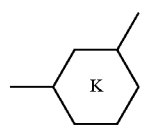

is a bivalent radical selected from the group consisting of phenylene-1,3-diyl, unsubstituted, monosubstituted or disubstituted by F, cyclohexane-1,3-diyl, unsubstituted or monosubstituted by F or CN, pyridine-2,6-diyl, pyridine-2,4-diyl, pyridine-3,5-diyl, pyridine-4,6-diyl, pyrimidine-4,6-diyl,

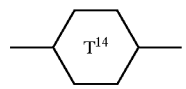

is a bivalent radical selected from the group of phenylene-1,4-diyl, unsubstituted, monosubstituted or disubstituted by CN or F, naphthalene-2,6-diyl, in which one or two ring carbon atoms may be replaced by N and which may be monosubstituted or disubstituted by CN or F, cyclohexane-1,4-diyl, cyclohex-1-ene-1,4-diyl, bicyclo[2,2,2]octane-1,4-diyl, (1,3)-dioxane-2,5-diyl, pyridine-2,5-diyl, unsubstituted or monosubstituted by F, pyrimidine-2,5-diyl, unsubstituted or monosubstituted by F, (1,3,4)-thiadiazole-2,5-diyl, indane-2,5-diyl, unsubstituted, monosubstituted or disubstitued by F in the aromatic ring, thiophene-2,5-diyl

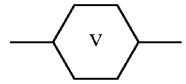

is a bivalent radical selected from the group consisting of phenylene-1,4-diyl, unsubstituted, monosubstituted or disubstituted by CN or F, naphthalene-2,6-diyl, in which one or two ring carbon atoms may be replaced by N and which may be monosubstituted or disubstituted by CN or F, cyclohexane-1,4-diyl, cyclohex-1-ene-1,4-diyl, bicyclo[2,2,2]octane-1,4-diyl, (1,3)-dioxane-2,5-diyl, indane-2,5-diyl, unsubstituted, monosubstituted or disubstituted by F in the aromatic ring, thiophene-2,5-diyl p, q, s are each zero or 1 r is 1 or 2.

9. The display as claimed in claim 1, wherein the smectic liquid-crystal mixture comprises from 10 to 60% of one or more compounds of the formula (I).

10. The display as claimed in claim 1 wherein the chiral smectic liquid-crystal mixture comprises from 10 to 60% of 1 to 15 compounds of the formula (I) and from 40 to 90% of 2 to 15 compounds of the formula (II).

11. A compound selected from compounds of the formula (XXIII), where:

compounds of the formula (XXV), where:

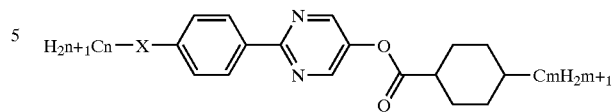

n is an integer from 2 to 13 m is an integer from 3 to 11

X is O or a single bond with the exception of n=2, m=11, X=O; n=5, m=5, X=O.

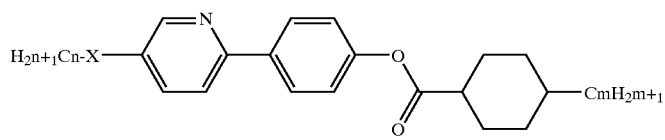

| n | 9 | 9 | 9 | 9 | 9 | 9 | 9 | 9 | 9 | 10 | 10 | 10 | 10 | 10 | 10 | 10 | 10 | 10 | 11 | 11 | 11 | 11 | 11 | 11 | 11 |
|---|---|---|---|---|---|---|---|---|---|----|----|----|----|----|----|----|----|----|----|----|----|----|----|----|----|
| m | 3 | 4 | 5 | 6 | 7 | 8 | 9 | 10 | 11 | 3 | 4 | 6 | 7 | 8 | 9 | 10 | 11 | 12 | 5 | 6 | 7 | 8 | 9 | 10 | 11 |
| X | — | — | — | — | — | — | — | — | — | — | — | — | — | — | — | — | — | — | — | — | — | — | — | — | — |

| n | 12 | 12 | 12 | 12 | 12 | 12 | 12 | 13 | 13 | 13 | 13 | 13 | 13 | 13 | 13 | 13 | 14 | 14 | 14 | 14 | 14 | 14 |
|---|----|----|----|----|----|----|----|----|----|----|----|----|----|----|----|----|----|----|----|----|----|----|
| m | 4 | 6 | 7 | 8 | 9 | 10 | 11 | 3 | 4 | 5 | 6 | 7 | 8 | 9 | 10 | 11 | 3 | 4 | 5 | 6 | 7 | 8 |
| X | — | — | — | — | — | — | — | — | — | — | — | — | — | — | — | — | — | — | — | — | — | — |

| n | 14 | 14 | 14 | 14 | 6 | 6 | 6 | 6 | 6 | 6 | 6 | 6 | 6 | 7 | 7 | 7 | 7 | 7 | 7 | 7 | 7 | 7 | 7 | 8 | 8 |
|---|----|----|----|----|---|---|---|---|---|---|---|---|---|---|---|---|---|---|---|---|---|---|---|---|---|
| m | 9 | 10 | 11 | 12 | 3 | 4 | 5 | 6 | 7 | 8 | 9 | 10 | 11 | 12 | 3 | 4 | 5 | 6 | 7 | 8 | 9 | 10 | 11 | 12 | 3 | 4 |
| X | — | — | — | — | O | O | O | O | O | O | O | O | O | O | O | O | O | O | O | O | O | O | O | O | O | O |

| n | 8 | 8 | 8 | 8 | 8 | 8 | 8 | 9 | 9 | 9 | 9 | 9 | 9 | 9 | 9 | 9 | 9 | 10 | 10 | 10 | 10 | 10 | 10 | 10 | 10 |
|---|---|---|---|---|---|---|---|---|---|---|---|---|---|---|---|---|---|---|----|----|----|----|----|----|----|
| m | 5 | 7 | 8 | 9 | 10 | 11 | 12 | 3 | 4 | 5 | 6 | 7 | 8 | 9 | 10 | 11 | 12 | 3 | 4 | 5 | 6 | 7 | 8 | 9 | 10 | 11 |
| X | O | O | O | O | O | O | O | O | O | O | O | O | O | O | O | O | O | O | O | O | O | O | O | O | O |

| n | 11 | 11 | 11 | 11 | 11 | 11 | 11 | 11 | 11 | 11 | 12 | 12 | 12 | 12 | 12 | 12 | 12 | 12 | 12 | 12 | 13 | 13 | 13 | 13 | 13 | 13 |
|---|----|----|----|----|----|----|----|----|----|----|----|----|----|----|----|----|----|----|----|----|----|----|----|----|----|----|
| m | 3 | 4 | 5 | 6 | 7 | 8 | 9 | 10 | 11 | 12 | 3 | 4 | 5 | 6 | 7 | 8 | 9 | 10 | 11 | 12 | 3 | 4 | 5 | 6 | 7 | 8 |
| X | O | O | O | O | O | O | O | O | O | O | O | O | O | O | O | O | O | O | O | O | O | O | O | O | O | O | compounds of the formula (XXIV), where:

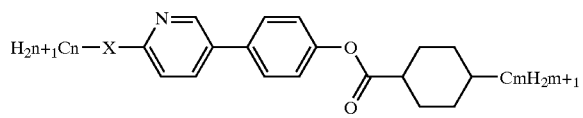

n is an integer from 8 to 14 m is an integer from 3 to 11

X is a single bond with the exception of n=11, m=3 or 5, X is a single bond.

compounds of the formula (XXVI), where:

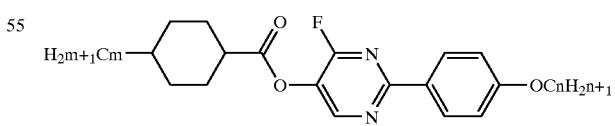

n is an integer from 5 to 13 m is an integer from 3 to 10 with the exception of n=8, m=5.

compounds of the formula (XXVII), where:

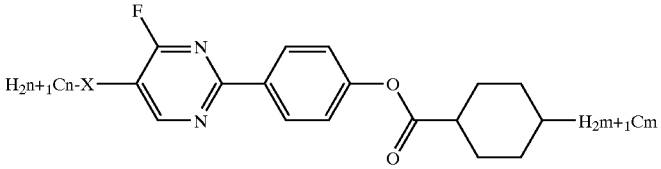

| n | 8 | 8 | 8 | 8 | 8 | 8 | 8 | 9 | 9 | 9 | 9 | 9 | 9 | 9 | 9 | 9 | 10 | 10 | 10 | 10 | 10 | 10 | 10 | 10 |
|---|---|---|---|---|---|---|---|---|---|---|---|---|---|---|---|---|----|----|----|----|----|----|----|----|
| m | 3 | 4 | 6 | 7 | 8 | 9 | 10 | 3 | 4 | 5 | 6 | 7 | 8 | 9 | 10 | 11 | 3 | 4 | 5 | 6 | 7 | 8 | 9 | 10 |
| X | — | — | — | — | — | — | — | — | — | — | — | — | — | — | — | — | — | — | — | — | — | — | — | — |

| n | 11 | 11 | 11 | 11 | 11 | 11 | 11 | 11 | 12 | 12 | 12 | 12 | 12 | 12 | 12 | 12 | 12 | 13 | 13 | 13 | 13 | 13 | 13 |
|---|----|----|----|----|----|----|----|----|----|----|----|----|----|----|----|----|----|----|----|----|----|----|----|
| m | 3 | 4 | 5 | 6 | 7 | 8 | 9 | 10 | 3 | 4 | 5 | 6 | 7 | 8 | 9 | 10 | 11 | 3 | 4 | 5 | 6 | 7 | 8 |
| X | — | — | — | — | — | — | — | — | — | — | — | — | — | — | — | — | — | — | — | — | — | — | — |

| n | 13 | 13 | 13 | 14 | 14 | 14 | 14 | 14 | 14 | 14 | 14 | 7 | 7 | 7 | 7 | 7 | 7 | 7 | 7 | 7 | 8 | 8 | 8 | 8 |
|---|----|----|----|----|----|----|----|----|----|----|----|---|---|---|---|---|---|---|---|---|---|---|---|---|
| m | 9 | 10 | 11 | 3 | 4 | 5 | 6 | 7 | 8 | 9 | 10 | 3 | 4 | 5 | 6 | 7 | 8 | 9 | 10 | 11 | 3 | 4 | 6 | 7 |
| X | — | — | — | — | — | — | — | — | — | — | — | O | O | O | O | O | O | O | O | O | O | O | O | O |

| n | 8 | 8 | 8 | 8 | 9 | 9 | 9 | 9 | 9 | 9 | 9 | 9 | 9 | 10 | 10 | 10 | 10 | 10 | 10 | 10 | 10 | 11 | 11 | 11 |
|---|---|---|---|---|---|---|---|---|---|---|---|---|---|----|----|----|----|----|----|----|----|----|----|----|
| m | 8 | 9 | 10 | 11 | 3 | 4 | 5 | 6 | 7 | 8 | 9 | 10 | 11 | 3 | 4 | 5 | 6 | 7 | 8 | 9 | 10 | 3 | 4 | 5 |
| X | O | O | O | O | O | O | O | O | O | O | O | O | O | O | O | O | O | O | O | O | O | O | O | O |

| n | 11 | 11 | 11 | 11 | 11 | 11 | 11 | 12 | 12 | 12 | 12 | 12 | 12 | 12 | 12 | 13 | 13 | 13 | 13 | 13 | 13 | 13 | 13 |
|---|----|----|----|----|----|----|----|----|----|----|----|----|----|----|----|----|----|----|----|----|----|----|----|
| m | 6 | 7 | 8 | 9 | 10 | 11 | 12 | 3 | 4 | 5 | 6 | 7 | 8 | 9 | 10 | 3 | 4 | 5 | 6 | 7 | 8 | 9 | 10 | 11 |
| X | O | O | O | O | O | O | O | O | O | O | O | O | O | O | O | O | O | O | O | O | O | O | O | compounds of the formula (XXIX), where:

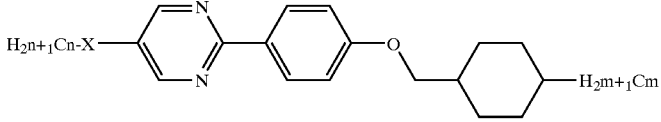

| n | 6 | 6 | 6 | 7 | 7 | 7 | 7 | 7 |
|---|---|---|---|---|---|---|---|---|
| m | 7 | 8 | 9 | 4 | 6 | 8 | 9 | 10 |
| X | — | — | — | — | — | — | — | — |

| n | 8 | 8 | 9 | 9 | 9 | 9 | 9 | 9 | 9 | 10 | 10 | 10 |
|---|---|---|---|---|---|---|---|---|---|----|----|----|
| m | 8 | 10 | 3 | 4 | 6 | 7 | 8 | 9 | 10 | 8 | 9 | 19 |
| X | — | — | — | — | — | — | — | — | — | — | — | — |

| n | 6 | 6 | 6 | 6 | 6 | 6 | 6 | 7 | 7 | 7 | 7 | 7 | 7 | 7 | 7 |
|---|---|---|---|---|---|---|---|---|---|---|---|---|---|---|---|
| m | 3 | 4 | 6 | 7 | 8 | 9 | 10 | 3 | 4 | 5 | 6 | 7 | 8 | 9 | 10 |
| X | O | O | O | O | O | O | O | O | O | O | O | O | O | O | O |

| n | 8 | 8 | 8 | 8 | 8 | 8 | 8 | 8 | 9 | 9 | 9 | 9 | 9 | 9 | 10 | 10 | 10 | 10 | 10 | 10 | 10 |
|---|---|---|---|---|---|---|---|---|---|---|---|---|---|---|----|----|----|----|----|----|----|
| m | 3 | 4 | 5 | 6 | 7 | 8 | 9 | 10 | 5 | 6 | 7 | 8 | 9 | 10 | 4 | 5 | 6 | 7 | 8 | 9 | 10 |
| X | O | O | O | O | O | O | O | O | O | O | O | O | O | O | O | O | O | O | O | O | O | compounds of the formula (XXX), where:

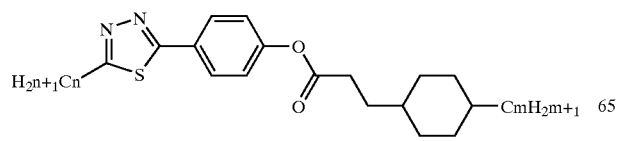

n is an integer from 5 to 13 m is an integer from 3 to 10 with the exception of n=8, m=4; n=9, m=3.

12. A compound selected from compounds of the formula (XXXI), where:

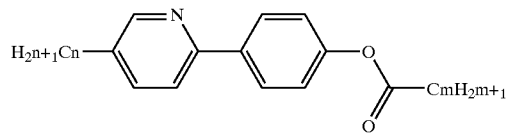
| n | 10 | 10 | 10 | 10 | 10 | 10 | 10 | 10 | 10 | 10 | 11 | 11 | 11 | 11 | 11 | 11 | 11 | 11 | 11 | 11 | 12 | 12 | 12 | 12 |
|---|----|----|----|----|----|----|----|----|----|----|----|----|----|----|----|----|----|----|----|----|----|----|----|----|
| m | 3 | 4 | 5 | 6 | 7 | 8 | 9 | 10 | 11 | 12 | 3 | 4 | 5 | 6 | 7 | 8 | 9 | 10 | 11 | 12 | 3 | 4 | 5 | 6 |
| X | — | — | — | — | — | — | — | — | — | — | — | — | — | — | — | — | — | — | — | — | — | — | — | — |
| n | 12 | 12 | 12 | 12 | 12 | 12 | 13 | 14 | 14 | 14 | 14 | 14 | 14 | 14 | 14 | 14 | 6 | 6 | 6 | 6 | 6 | 6 | 6 | 6 |
|---|----|----|----|----|----|----|----|----|----|----|----|----|----|----|----|----|----|----|----|----|----|----|----|----|
| m | 7 | 8 | 9 | 10 | 11 | 12 | 3 | 4 | 5 | 6 | 7 | 8 | 9 | 10 | 11 | 12 | 3 | 4 | 5 | 6 | 7 | 8 | 9 | 10 |
| X | — | — | — | — | — | — | — | — | — | — | — | — | — | — | — | — | O | O | O | O | O | O | O | O |
| n | 6 | 6 | 7 | 7 | 7 | 7 | 7 | 7 | 7 | 7 | 7 | 7 | 8 | 8 | 8 | 8 | 8 | 8 | 8 | 8 | 8 | 9 | 9 | 9 |
|---|---|---|---|---|---|---|---|---|---|---|---|---|---|---|---|---|---|---|---|---|---|---|---|---|
| m | 11 | 12 | 3 | 4 | 5 | 6 | 7 | 8 | 9 | 10 | 11 | 12 | 3 | 4 | 5 | 6 | 8 | 9 | 10 | 11 | 12 | 3 | 4 | 5 |
| X | O | O | O | O | O | O | O | O | O | O | O | O | O | O | O | O | O | O | O | O | O | O | O | O |
| n | 9 | 9 | 9 | 9 | 9 | 9 | 9 | 10 | 10 | 10 | 10 | 10 | 10 | 10 | 10 | 10 | 10 | 11 | 11 | 11 | 11 | 11 | 11 | 11 |
|---|---|---|---|---|---|---|---|----|----|----|----|----|----|----|----|----|----|----|----|----|----|----|----|----|
| m | 6 | 7 | 8 | 9 | 10 | 11 | 12 | 3 | 4 | 5 | 6 | 7 | 8 | 9 | 10 | 11 | 12 | 3 | 4 | 5 | 6 | 7 | 8 | 9 |
| X | O | O | O | O | O | O | O | O | O | O | O | O | O | O | O | O | O | O | O | O | O | O | O | O |
| n | 11 | 11 | 11 | 12 | 12 | 12 | 12 | 12 | 12 | 12 | 12 | 12 | 12 | 13 | 13 | 13 | 13 | 13 | 13 | 13 | 13 | 13 | 13 | 14 |
|---|----|----|----|----|----|----|----|----|----|----|----|----|----|----|----|----|----|----|----|----|----|----|----|----|
| m | 10 | 11 | 12 | 3 | 4 | 5 | 6 | 7 | 8 | 9 | 10 | 11 | 12 | 3 | 4 | 5 | 6 | 7 | 8 | 9 | 10 | 11 | 12 | 3 |
| X | O | O | O | O | O | O | O | O | O | O | O | O | O | O | O | O | O | O | O | O | O | O | O | O |
| n | 14 | 14 | 14 | 14 | 14 | 14 | 14 | 14 | 14 |
|---|----|----|----|----|----|----|----|----|----|
| m | 4 | 5 | 6 | 7 | 8 | 9 | 10 | 11 | 12 |
| X | O | O | O | O | O | O | O | O | O |
compounds of the formula (XXVIII), where:
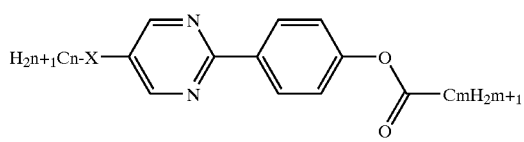
| n | 11 | 12 | 13 | 14 | 13 | 14 | 12 | 13 | 14 | 13 | 14 | 10 | 11 | 12 | 13 | 14 | 13 | 14 | 9 | 10 | 11 | 12 | 13 | 10 |
|---|----|----|----|----|----|----|----|----|----|----|----|----|----|----|----|----|----|----|----|----|----|----|----|----|
| m | 5 | 5 | 5 | 5 | 6 | 6 | 7 | 7 | 7 | 8 | 8 | 9 | 9 | 9 | 9 | 9 | 10 | 10 | 11 | 11 | 11 | 11 | 11 | 12 |
| X | — | — | — | — | — | — | — | — | — | — | — | — | — | — | — | — | — | — | — | — | — | — | — | — |
| n | 11 | 12 | 13 | 14 | 6 | 6 | 6 | 6 | 6 | 6 | 6 | 6 | 6 | 7 | 7 | 7 | 7 | 7 | 7 | 7 | 7 | 7 | 8 | 8 |
|---|----|----|----|----|---|---|---|---|---|---|---|---|---|---|---|---|---|---|---|---|---|---|---|---|
| m | 12 | 12 | 12 | 12 | 4 | 5 | 6 | 7 | 8 | 9 | 10 | 11 | 12 | 4 | 5 | 6 | 7 | 8 | 9 | 10 | 11 | 12 | 4 | 6 |
| X | — | — | — | — | O | O | O | O | O | O | O | O | O | O | O | O | O | O | O | O | O | O | O | O |
| n | 8 | 8 | 8 | 8 | 9 | 9 | 9 | 9 | 9 | 9 | 9 | 10 | 10 | 10 | 10 | 10 | 10 | 10 | 10 | 10 | 11 | 11 | 11 | 11 |
|---|---|---|---|---|---|---|---|---|---|---|---|----|----|----|----|----|----|----|----|----|----|----|----|----|
| m | 8 | 10 | 11 | 12 | 4 | 5 | 6 | 8 | 9 | 10 | 11 | 12 | 4 | 5 | 7 | 8 | 9 | 10 | 11 | 12 | 4 | 5 | 6 | 7 |
| X | O | O | O | O | O | O | O | O | O | O | O | O | O | O | O | O | O | O | O | O | O | O | O | O |
| n | 11 | 11 | 11 | 11 | 11 | 12 | 12 | 12 | 12 | 12 | 12 | 12 | 12 |
|---|----|----|----|----|----|----|----|----|----|----|----|----|----|
| m | 8 | 9 | 10 | 11 | 12 | 5 | 6 | 7 | 8 | 9 | 10 | 11 | 12 |
| X | O | O | O | O | O | O | O | O | O | O | O | O | O | compounds of the formula (XXXII), where:

[Structure: H$_{2n+1}$C$_n$-(phenyl with Z substituent)-pyrimidine-O-C(=O)-thiophene-C$_m$H$_{2m+1}$]

| n | 5 | 5 | 5 | 5 | 5 | 5 | 5 | 5 | 6 | 6 | 6 | 6 | 6 | 6 | 6 | 6 | 7 | 7 | 7 | 7 |
|---|---|---|---|---|---|---|---|---|---|---|---|---|---|---|---|---|---|---|---|---|
| m | 2 | 3 | 4 | 5 | 6 | 7 | 8 | 9 | 2 | 3 | 4 | 5 | 6 | 7 | 8 | 9 | 2 | 3 | 4 | 5 |

| n | 7 | 7 | 7 | 7 | 8 | 8 | 8 | 8 | 8 | 8 | 8 | 8 | 9 | 9 | 9 | 9 | 9 | 9 | 9 | 9 | 10 | 10 | 10 | 10 | 10 |
|---|---|---|---|---|---|---|---|---|---|---|---|---|---|---|---|---|---|---|---|---|---|---|---|---|---|
| m | 6 | 7 | 8 | 9 | 2 | 3 | 4 | 5 | 6 | 7 | 8 | 9 | 2 | 3 | 4 | 5 | 6 | 7 | 8 | 9 | 2 | 3 | 4 | 5 | 6 |

| n | 10 | 10 | 10 | 11 | 11 | 11 | 11 | 11 | 11 | 11 | 11 | 12 | 12 | 12 | 12 | 12 | 12 | 12 | 12 | 13 | 13 | 13 |
|---|----|----|----|----|----|----|----|----|----|----|----|----|----|----|----|----|----|----|----|----|----|----|
| m | 7 | 8 | 9 | 2 | 3 | 4 | 5 | 6 | 7 | 8 | 9 | 2 | 3 | 4 | 5 | 6 | 7 | 8 | 9 | 2 | 3 | 4 |

| n | 13 | 13 | 13 | 13 | 13 | 14 | 14 | 14 | 14 | 14 | 14 | 14 | 14 |
|---|----|----|----|----|----|----|----|----|----|----|----|----|----|
| m | 5 | 6 | 7 | 8 | 9 | 2 | 3 | 4 | 5 | 6 | 7 | 8 | 9 | and where Z is H or F in all cases.

* * * * *